(12) United States Patent
Firminger et al.

(10) Patent No.: US 8,095,384 B2
(45) Date of Patent: Jan. 10, 2012

(54) COMPUTATIONAL SYSTEMS AND METHODS FOR HEALTH SERVICES PLANNING AND MATCHING

(75) Inventors: Shawn P. Firminger, Redmond, WA (US); Jason Garms, Redmond, WA (US); Roderick A. Hyde, Redmond, WA (US); Edward K.Y. Jung, Bellevue, WA (US); Chris Demetrios Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, Bellevue, WA (US)

( * ) Notice: Subject to any disclaimer, the term of this patent is extended or adjusted under 35 U.S.C. 154(b) by 69 days.

(21) Appl. No.: 12/592,768

(22) Filed: Dec. 2, 2009

(65) Prior Publication Data

US 2010/0241454 A1    Sep. 23, 2010

Related U.S. Application Data

(63) Continuation-in-part of application No. 12/590,335, filed on Nov. 5, 2009, and a continuation-in-part of application No. 12/590,250, filed on Nov. 4, 2009, and a continuation-in-part of application No. 12/590,163, filed on Nov. 3, 2009, and a continuation-in-part of application No. 12/590,104, filed on Nov. 2, 2009, and a continuation-in-part of application No. 12/589,728, filed on Oct. 27, 2009, and a continuation-in-part of application No. 12/589,639, filed on Oct. 26, 2009, and a continuation-in-part of application No. 12/589,171, filed on Oct. 19, 2009, and a continuation-in-part of application No. 12/589,124, filed on Oct. 16, 2009, and a continuation-in-part of application No. 12/587,313, filed on Oct. 5, 2009, and a continuation-in-part of application No. 12/587,239, filed on Oct. 2, 2009, and a continuation-in-part of application No. 12/381,680, filed on Mar. 12, 2009, and a continuation-in-part of application No. 12/381,377, filed on Mar. 10, 2009.

(51) Int. Cl.
*G06Q 10/00* (2006.01)
*G06F 19/00* (2006.01)

(52) U.S. Cl. .............................. 705/2; 705/3

(58) Field of Classification Search ................... 705/2–3
See application file for complete search history.

(56) References Cited

U.S. PATENT DOCUMENTS 5,911,132 A    6/1999 Sloane
(Continued)

OTHER PUBLICATIONS

MediBid; "MediBid is The Marketplace for Medicine®"; printed on Apr. 25, 2011; pp. 1-2; located at http://www.medibid.com.

(Continued)

*Primary Examiner* — Luke Gilligan
*Assistant Examiner* — Joseph Burgess
(74) *Attorney, Agent, or Firm* — Keller LaPuma Woodard PC IV; Gerald M. Keller

(57) ABSTRACT

Systems and methods are described relating to accepting user input relating to a plurality of health service option selection factors; presenting a plurality of choices for at least one of the health service option selection factors; and presenting at least one outcome output based on a selection of at least one of the plurality of choices for at least one of the health service option selection factors.

49 Claims, 46 Drawing Sheets

U.S. PATENT DOCUMENTS

| | | | |
|---|---|---|---|
| 5,926,794 | A | 7/1999 | Fethe |
| 6,014,654 | A | 1/2000 | Ariyoshi |
| 6,807,531 | B1 | 10/2004 | Kanai |
| 6,915,297 | B2 | 7/2005 | Chou |
| 7,079,977 | B2 | 7/2006 | Osorio et al. |
| 7,406,453 | B2 | 7/2008 | Mundie et al. |
| 7,711,580 | B1 | 5/2010 | Hudson |
| 7,901,368 | B2 | 3/2011 | Flaherty et al. |
| 2002/0065758 | A1 | 5/2002 | Henley |
| 2003/0046113 | A1 | 3/2003 | Johnson et al. |
| 2004/0015337 | A1 | 1/2004 | Thomas et al. |
| 2005/0125289 | A1 | 6/2005 | Beyda et al. |
| 2006/0136264 | A1 | 6/2006 | Eaton et al. |
| 2006/0230033 | A1 | 10/2006 | Halevy et al. |
| 2007/0087901 | A1 | 4/2007 | Brassil et al. |
| 2007/0150024 | A1 | 6/2007 | Leyde et al. |
| 2007/0250343 | A1 | 10/2007 | Sohal |
| 2007/0271119 | A1 | 11/2007 | Boerger et al. |
| 2008/0091086 | A1 | 4/2008 | Legere et al. |
| 2008/0154912 | A1 | 6/2008 | Weber et al. |
| 2008/0172214 | A1* | 7/2008 | Col et al. .................. 703/11 |
| 2008/0215570 | A1 | 9/2008 | Maloney et al. |
| 2008/0215627 | A1 | 9/2008 | Higgins et al. |
| 2009/0240527 | A1 | 9/2009 | Bluth |

OTHER PUBLICATIONS

Medicine Online; printed on Apr. 25, 2011; pp. 1-2; located at http://www.medicineonline.com.

Rustad, Mitch; "Bid-For-Surgery Web Site to Launch"; Medical Tribune; bearing a date of 1999; printed on Apr. 25, 2011; pp. 1-3; 40(21):3; located at http://www.mol.net/media/medscape-trib-/Bid-For-Surgery_Web_Site_To_Launch.htm.

U.S. Appl. No. 12/592,439, Firminger et al.
U.S. Appl. No. 12/590,335, Firminger et al.
U.S. Appl. No. 12/590,250, Firminger et al.
U.S. Appl. No. 12/590,163, Firminger et al.
U.S. Appl. No. 12/590,104, Firminger et al.
U.S. Appl. No. 12/589,728, Firminger et al.
U.S. Appl. No. 12/589,639, Firminger et al.
U.S. Appl. No. 12/589,171, Firminger et al.
U.S. Appl. No. 12/589,124, Firminger et al.

"Cancer in Scotland: Radiotherapy Activity Planning for Scotland 2011-2015," available at http://www.scotland.gov.uk/Publications/2006/01/24131719/28, (2006).

Frenkel et al., "An approach for integrating complementary-alternative medicine into primary care," Fam. Pract., 20(3), pp. 324-332 (2003).

Goodman, Clifford S., "Introduction to Health Care Technology Assessment," available at http://www.nlm.nih.gov/nichsr/hta101/ta101_c1.html, (Jan. 2004).

Martinez-Serra et al., "Symptom Priority Ranking in the Care of Gastroesophageal Reflux: A Review of 1,850 Cases," Dig Dis, 17:219-224 (1999).

Tarricone et al., "Economic evaluation of nimesulide versus diclofenac in the treatment of osteoarthritis in France, Italy and Spain," Clin. Drug Invest. 21(7) pp. 453-464 (2001).

U.S. Appl. No. 12/587,313, Firminger et al.
U.S. Appl. No. 12/587,239, Firminger et al.
U.S. Appl. No. 12/381,680, Firminger et al.
U.S. Appl. No. 12/381,377, Firminger et al.

* cited by examiner

FIG. 16

| 160 Service Provider | Specialty | Years in Practice | Medical Education | Board Certification | Insurance Accepted | Location |
|---|---|---|---|---|---|---|
| 1310 Doctor A | Plastic surgery | 5 | Harvard Med. | ABS, ABPS | Major medical | Miami FL |
| 1312 Doctor B | Gastro-enterology | 25 | Cornell Med. | ABS | Major medical | Miami Beach FL |
| 1314 Doctor C | Gastro-enterology | 7 | UCLA Med. | ABS | Major medical | Bal Harbour FL |
| 1316 Doctor D | Gastro-enterology | 19 | Pitt Med. | ABS | Major medical | Miami FL |
| 1318 Doctor E | Gastro-enterology | 12 | Columbia Med. | ABS | Major medical | Miami FL |

FIG. 25

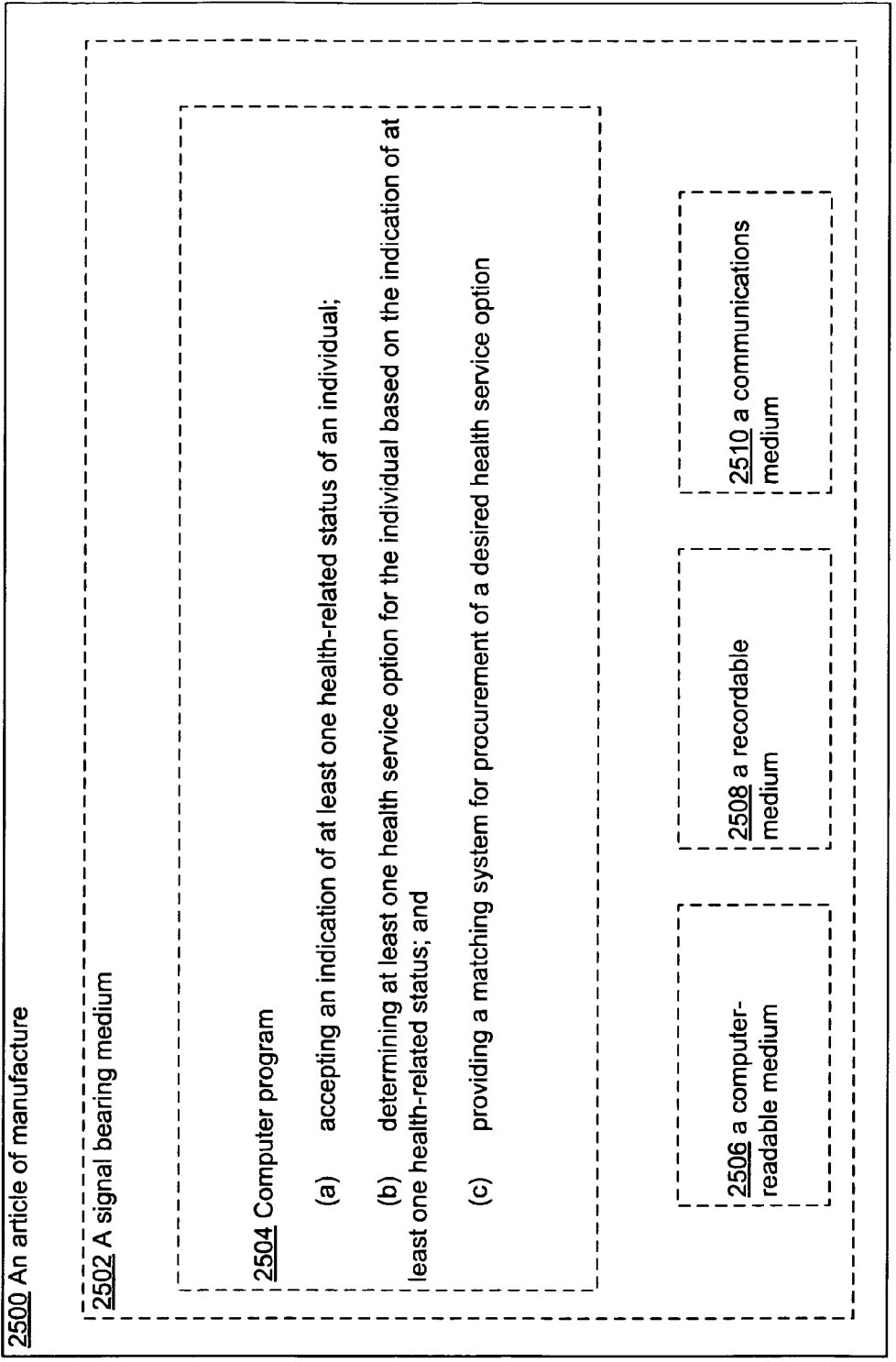
100 System

2500 An article of manufacture

2502 A signal bearing medium

2504 Computer program (a) accepting an indication of at least one health-related status of an individual;

(b) determining at least one health service option for the individual based on the indication of at least one health-related status; and (c) providing a matching system for procurement of a desired health service option 2506 a computer-readable medium 2508 a recordable medium 2510 a communications medium

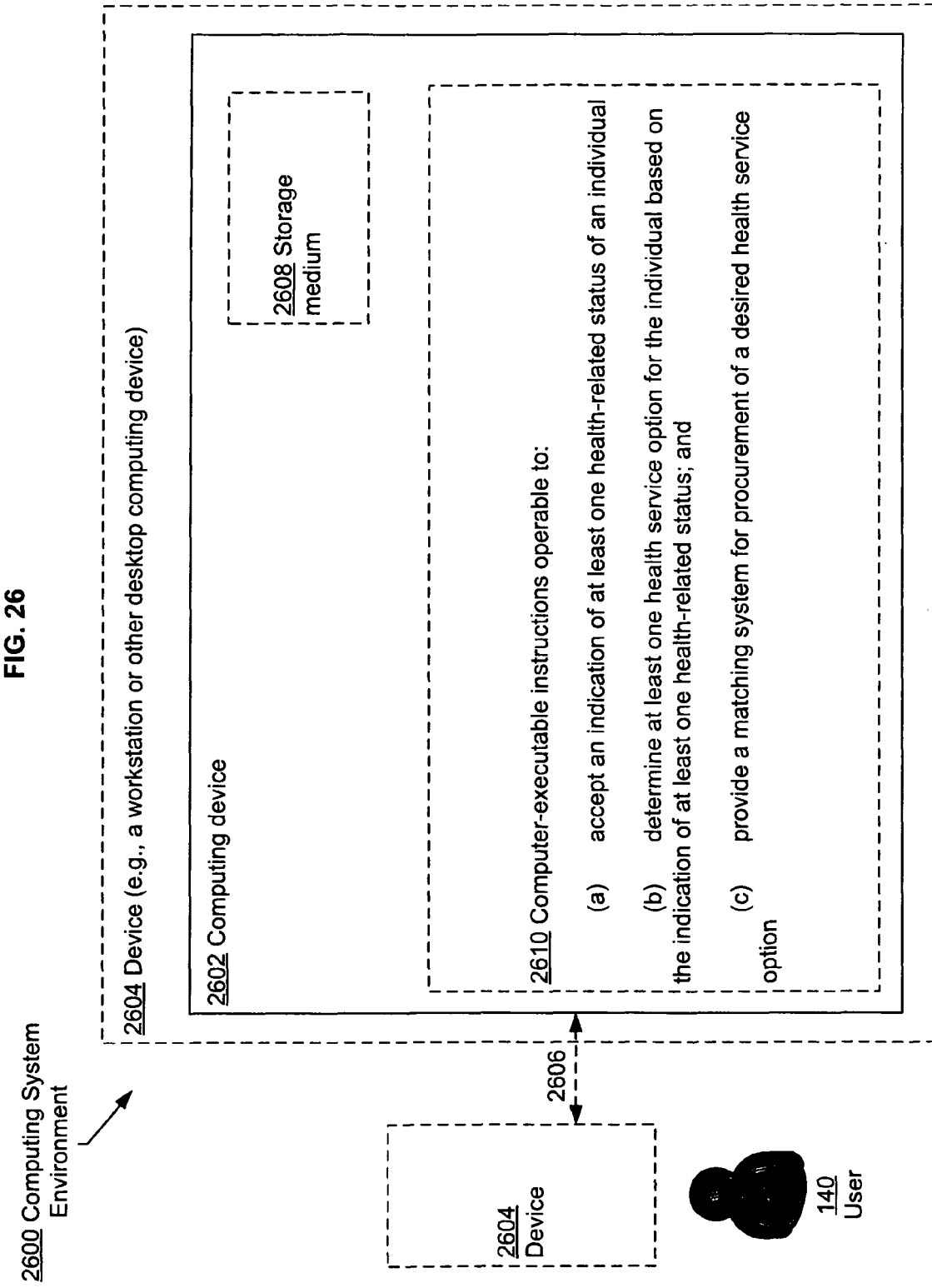

COMPUTATIONAL SYSTEMS AND METHODS FOR HEALTH SERVICES PLANNING AND MATCHING

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/381,377, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 10 Mar. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,680, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 12 Mar. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,239, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,313, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,124, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 16 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,171, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 19 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,639, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 26 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,728, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 27 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,104, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,163, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,250, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 4 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,335, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,439, entitled COMPUTATIONAL SYSTEMS AND METHODS FOR HEALTH SERVICES PLANNING AND MATCHING, naming Shawn P. Firminger, Jason Garms, Roderick A. Hyde; Edward K.Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 24 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,541, entitled COMPUTATIONAL SYSTEMS AND METHODS FOR HEALTH SERVICES PLANNING AND MATCHING, naming Shawn P. Firminger, Jason Garms, Roderick A. Hyde; Edward K.Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 25 Nov. 2009 which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to data capture and data handling techniques.

SUMMARY

In one aspect, a method includes but is not limited to accepting user input relating to a plurality of health service option selection factors, presenting a plurality of choices for at least one of the health service option selection factors, and presenting at least one outcome output based on a selection of at least one of the plurality of choices for at least one of the health service option selection factors. In addition to the foregoing, other apparatus aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to means for accepting user input relating to a plurality of health service option selection factors, means for presenting a plurality of choices for at least one of the health service option selection factors, and means for presenting at least one outcome output based on a selection of at least one of the plurality of choices for at least one of the health service option selection factors. In addition to the foregoing, other apparatus aspects are described in the claims, drawings, and text forming a part of the present disclosure.

In one aspect, a system includes but is not limited to circuitry for accepting user input relating to a plurality of health service option selection factors, circuitry for presenting a plurality of choices for at least one of the health service option selection factors, and circuitry for presenting at least one outcome output based on a selection of at least one of the plurality of choices for at least one of the health service option selection factors. In addition to the foregoing, other apparatus aspects are described in the claims, drawings, and text forming a part of the present disclosure.

In one aspect, a system includes but is not limited to one or more instructions for accepting user input relating to a plurality of health service option selection factors, one or more instructions for presenting a plurality of choices for at least one of the health service option selection factors, and one or more instructions for presenting at least one outcome output based on a selection of at least one of the plurality of choices for at least one of the health service option selection factors. In addition to the foregoing, other apparatus aspects are described in the claims, drawings, and text forming a part of the present disclosure.

In one aspect, a computer program product includes but is not limited to a signal-bearing medium bearing accept user input relating to a plurality of health service option selection factors, present a plurality of choices for at least one of the health service option selection factors, and present at least one outcome output based on a selection of at least one of the plurality of choices for at least one of the health service option selection factors. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 16 illustrates an example of a set of determined health service options.

FIG. 25 illustrates a partial view of an example article of manufacture including a computer program product that includes a computer program for executing a computer process on a computing device related to health services planning and matching, which may serve as a context for introducing one or more processes and/or devices described herein.

FIG. 26 illustrates an example device in which embodiments may be implemented related to health services planning and matching, which may serve as a context for introducing one or more processes and/or devices described herein.

DETAILED DESCRIPTION

Figure 1:
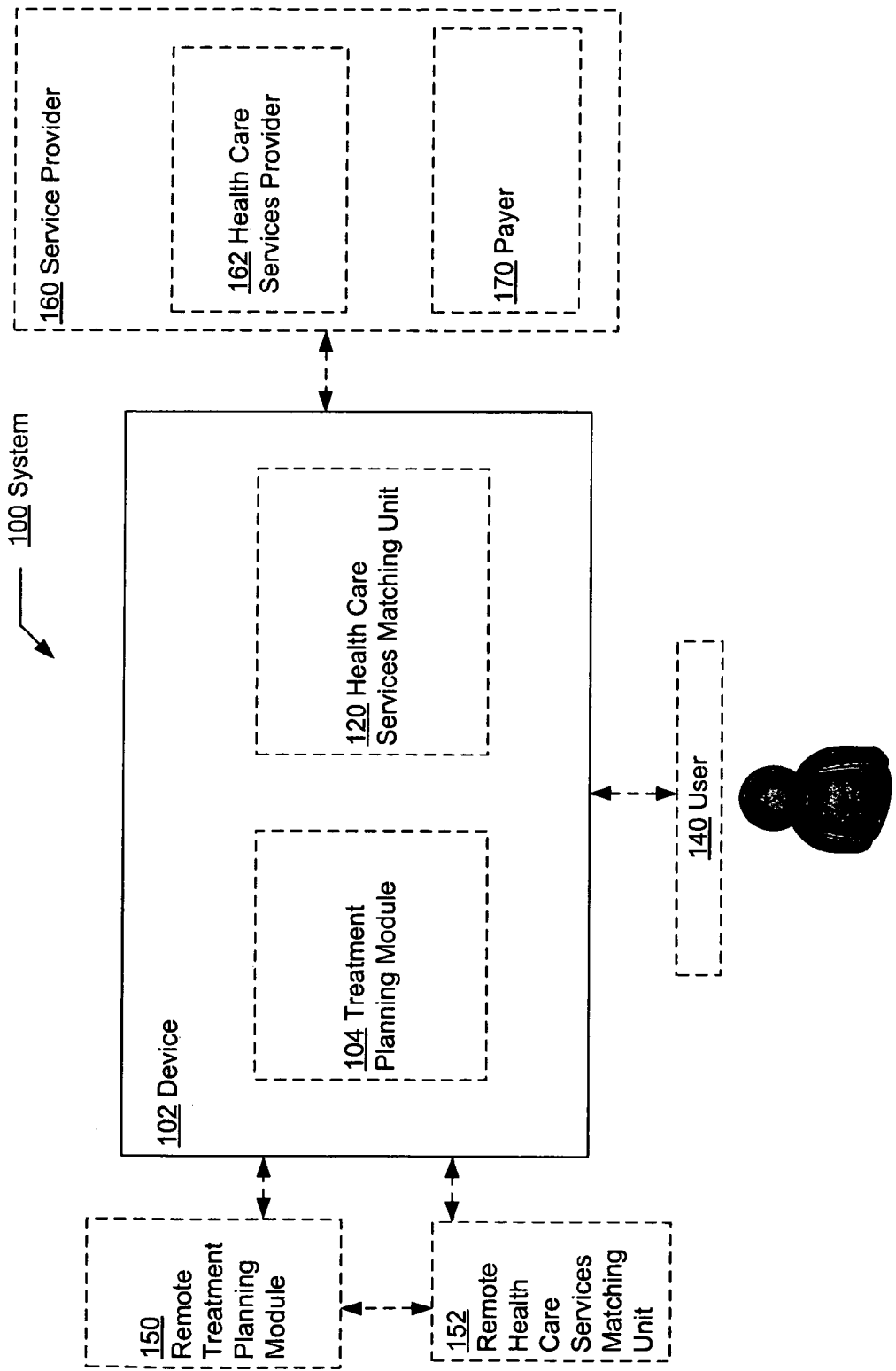
FIG. 1 illustrates an example of a health services planning and matching system in which embodiments may be implemented, perhaps in a device and/or through a network, which may serve as a context for introducing one or more processes and/or devices described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example system 100 in which embodiments may be implemented. The system 100 includes a device 102. The device 102 may contain, for example, treatment planning module 104 and health care services matching unit 120. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept user input to provide one or more health services options, for example via treatment planning module 104. Device 102 may accept a selected health service option and match it with an appropriate service provider via, for example health care services matching unit 120. Service provider 160 may include, for example, health care services provider 162 and/or payer 170.

In FIG. 1, health care services matching unit 120 may solicit a health care services option from a service provider 160. Such a solicitation may include an invitation to bid in an auction, a reverse auction, or the like. Results of such a solicitation may include matching a doctor capable of providing a chosen health care services option with the user 140 in need of the chosen health care services option, perhaps according to one or more preferences provided by the user 140.

In FIG. 1, the device 102 is illustrated as possibly being included within a system 100. Of course, virtually any kind of computing device may be used to implement the special purpose treatment planning module 104 and/or special purpose health care services matching unit 120, such as, for example, a workstation, a desktop computer, a networked computer, a server, a collection of servers and/or databases, a virtual machine running inside a computing device, a mobile computing device, or a tablet PC.

Additionally, not all of the treatment planning module 104 and/or health care services matching unit 120 need be implemented on a single computing device. For example, the treatment planning module 104 and/or health care services matching unit 120 may be implemented and/or operable on a remote computer, while a user interface and/or local instance of the treatment planning module 104 and/or health care services matching unit 120 are implemented and/or occur on a local computer. Further, aspects of the treatment planning module 104 and/or health care services matching unit 120 may be implemented in different combinations and implementations than that shown in FIG. 1. For example, functionality of a user interface may be incorporated into the treatment planning module 104 and/or health care services matching unit 120. The treatment planning module 104 and/or health care services matching unit 120 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, the treatment planning module 104 and/or health care services matching unit 120 may process user input data according to health care options and/or service provider information available as updates through a network.

Treatment planning module 104 and/or health care services matching unit 120 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
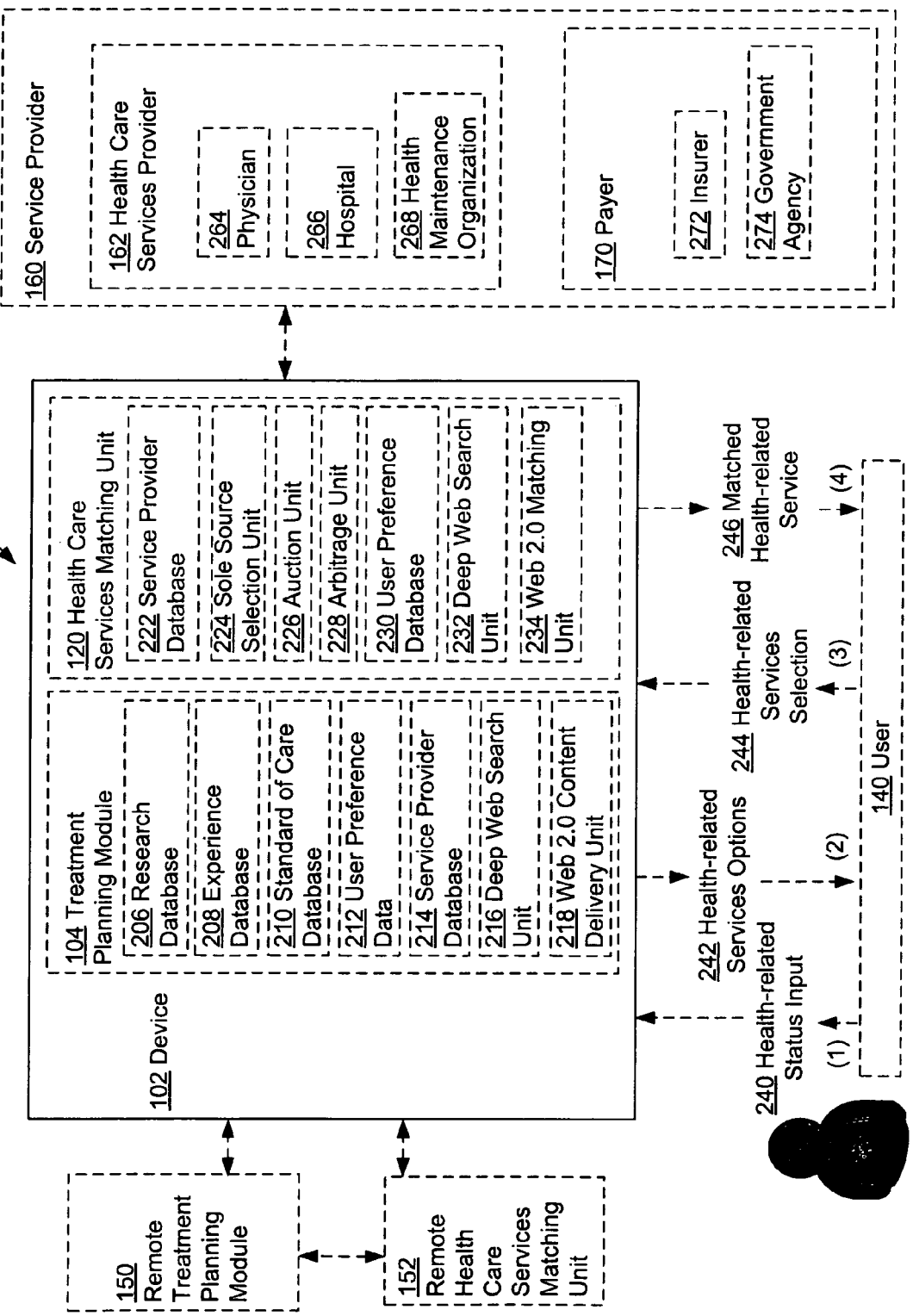
FIG. 2 illustrates certain alternative embodiments of the health services planning and matching system of FIG. 1.

FIG. 2 illustrates certain alternative embodiments of the system 100 of FIG. 1. In FIG. 2, the user 140 may interact with treatment planning module 104 and/or health care services matching unit 120 operable on the device 102. Health-related status input 240 may be input to treatment planning module 104 implemented on the device 102. The device 102 can communicate over a network with remote treatment planning module 150 and/or remote health care services matching unit 152. Treatment planning module 104 may include, for example, research database 206, experience database 208, standard of care database 210, user preference data 212, service provider database 214, Deep Web search unit 216, and/or Web 2.0 content delivery unit 218. The treatment planning module 104 may access and send health-related services options 242 to user 140. User 140 may subsequently choose and send health-related services selection 244 including a desired health service option to device 102 including health care services matching unit 120. Health care services matching unit 120 may include, for example, service provider database 222, sole source selection unit 224, auction unit 226, 228 arbitrage unit 228, user preference database 230, Deep Web search unit 232, and/or Web 2.0 matching unit 234. Health care services matching unit 120 may communicate directly or over a network with service provider 160 to obtain a suitable health-related service according to health-related services selection 244 and any user preference contained, for example, in user preference database 230. Service provider 160 may include health care services provider 162 and/or payer 170. Health care services provider 162 may include, for example, physician 264, hospital 266, and/or health maintenance organization 268. Payer 170 may include, for example, insurer 272, and/or government agency 274. Health care services matching unit 120 may then present matched health-related service 246 to user 140.

In this way, the user 140, who may be using a mobile device that is connected through a network with the system 100 and/or device 102 (e.g., in an office, outdoors and/or in a public environment), may generate a matched health-related service 246 as if the user 140 were interacting locally with the device 102 and/or system 100.

As referenced herein, the treatment planning module 104 and/or health care services matching unit 120 may be used to perform various data querying and/or recall techniques with respect to the health-related status input 240 and/or health-related services selection 244, in order to obtain and/or present health-related services options 242 and/or matched health-related service 246. For example, where the health-related status input 240 is organized, keyed to, and/or otherwise accessible using one or more reference health-related status indicators such as symptom, disease, diagnosis, or the like, treatment planning module 104 and/or health care services matching unit 120 may employ various Boolean, statistical, and/or semi-boolean searching techniques to match health-related status input 240 and/or health-related services selection 244 with one or more appropriate health-related services options 242 and/or matched health-related service 246. Similarly, for example, where user preference data is organized, keyed to, and/or otherwise accessible using one or more service provider 160 interest profiles, various Boolean, statistical, and/or semi-boolean searching techniques may be performed by health care services matching unit 120 to match a given health-related services selection 244 with a service provider 160 to present, for example, a matched health-related service 246.

Many examples of databases and database structures may be used in connection with the treatment planning module 104 and/or health care services matching unit 120. Such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more reference health attribute and/or reference service provider may be performed, or Boolean operations using a reference health attribute and/or reference service provider may be performed. For example, weighted Boolean operations may be performed in which different weights or priorities are assigned to one or more of the reference health-related status attributes and/or reference service providers, including reference health conditions and/or reference service providers associated with various reference health-related status attributes, perhaps relative to one another. For example, a number-weighted, exclusive-OR operation may be performed to request specific weightings of desired (or undesired) health reference data or service providers to be included or excluded. Reference health-related status attributes may include normal physiological values for such health-related things as pain, reaction time, body or eye movement, memory, alertness, blood pressure, or the like. Such normal physiological values may be "normal" relative to the user 140, to a subpopulation to which the user 140 belongs, or to a general population. Similarly, reference service providers may be associated with, for example, the general medical community, a medical specialty, a local geographical area or the like.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 3:
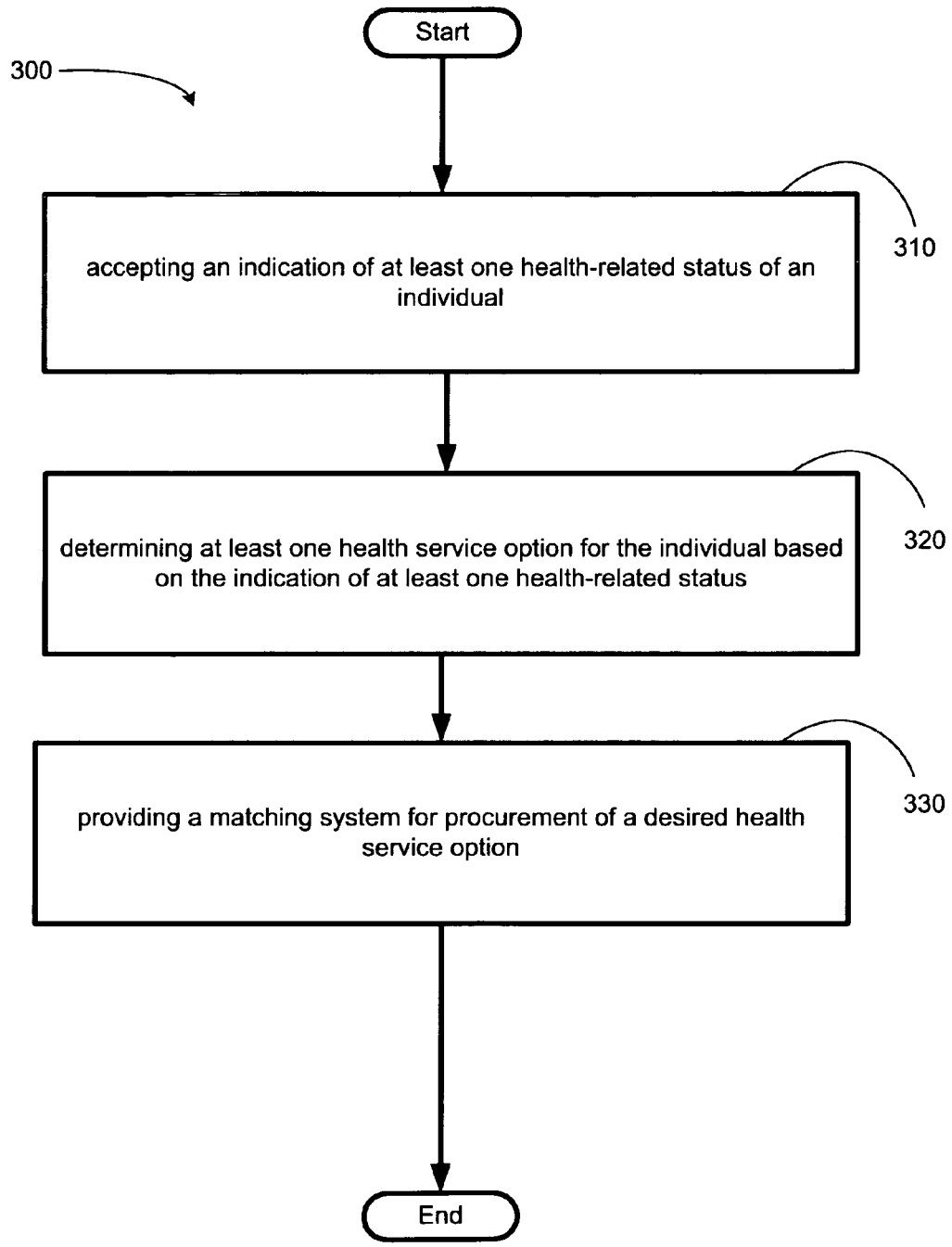
FIG. 3 illustrates an example of an operational flow representing example operations related to health services planning and matching, which may serve as a context for introducing one or more processes and/or devices described herein.

FIG. 3 illustrates an operational flow 300 representing example operations related to health services planning and matching. In FIG. 3 and in following figures that include various examples of operational flows, discussion and explanation may be provided with respect to the above-described system environments of FIGS. 1-2, and/or with respect to other examples and contexts. However, it should be understood that the operational flows may be executed in a number of other environments and contexts including that of FIG. 20, and/or in modified versions of FIGS. 1-2. Also, although the various operational flows are presented in the sequence(s) illustrated, it should be understood that the various operations may be performed in other orders than those which are illustrated, or may be performed concurrently.

After a start operation, operation 310 depicts accepting an indication of at least one health-related status of an individual. For example, a user 140 can enter into device 102 a symptom or disease. The user 140 may be a patient newly informed of a medical condition, an individual experiencing one or more symptoms, a health care practitioner investigating health care services options for a patient in their care, a health care maintenance organization planning for the care of a patient, or the like. An indication of at least one health-related status of an individual may also include a desire for cosmetic enhancement, pregnancy, or improvement in athletic performance.

Operation 320 depicts determining at least one health service option for the individual based on the indication of at least one health-related status. For example, device 102 and/or treatment planning module 104, upon accepting a symptom or disease from a user 140, for example, may access a standard of care database 210 so as to generate a set of health care services options. For example, if a user 140 entered "pancreatic cancer," the treatment planning module may determine testing and treatment options recommended for pancreatic cancer by the American Medical Association. Such standard of care options may include biopsy, curative surgery including the Whipple procedure, palliative surgery, radiation therapy, chemotherapy, drug therapy including erlotinib and/or gemcitabine, changes to the diet, and/or pain medication. In one embodiment, treatment planning module 104 may present the options in the form of a decision tree, with testing and treatment steps presented in a branching, sequential format showing the timing of treatment steps, required treatments conditioned upon various testing results, and the like. Duration of treatment may also be determined, for example, a course of weeks or months for chemotherapy and/or radiation therapy. In other embodiments, cost estimates may be determined for various health care services options. In still other embodiments, statistics may be determined various health care services options, such as, for example, 5-year survival rates for various cancer interventions, morbidity and/or mortality rates for a given disease therapy, or side effect frequency and/or severity for a given cosmetic procedure.

One example of such a decision tree can be found in Tarricone et al., "Economic evaluation of nimesulide versus diclofenac in the treatment of osteoarthritis in France, Italy and Spain," Clin. Drug Invest. 21(7) pp. 453-464 (2001) (incorporated herein by reference in its entirety), in which a decision tree is presented that contains all the possible chance nodes for each treatment branch as well as adverse events with probabilities for each. An optional component that can be presented for each treatment option is a financial cost and/or an estimate of time required for a given treatment option.

For example, treatment planning module 102 may access data from research database 206, experience database 208, and/or standard of care database 210. For example, research database 206 may include information published in scientific journals, for example, published results of clinical testing. Other sources of research data include government data found at, for example, clinicaltrials.gov, a central repository for clinical trial planning and results. At clinicaltrials.gov, the data may be searched by word or phrase, for example, condition, drug intervention, sponsor, and/or location. Studies may also be searched by age group. Similar databases exist for alternative medicine trials, for example, as found at the National Cancer Institute's web page http://www.cancer.gov/CAM/clinicaltrials_list.html.

For example, the Health Services Technology/Assessment Texts (HSTAT) is a free, Web-based resource of full-text documents that provide health information and support health care decision making. HSTAT's audience includes health care providers, health service researchers, policy makers, payers, consumers and the information professionals who serve these groups. The web address is http://www.ncbi.nlm.nih.gov/books/by.fcgi?rid=hstat and the site allows searching by key word, such as "cancer pain." Such a search brings results from the NCBI Bookshelf database, including excerpts from books that discuss the topic. Examples of available information includes, for cancer pain, discussions of, inter alia, NSAIDS, opioids, bisphosphonates for bone cancer pain, reflexology, and acupuncture.

An experience database 208 may include information provided by individual(s) who have undergone testing and or treatment and who have provided results and/or subjective conclusions based on their own experience. Such a database may take the form of a information compiled by online patient communities, peer-to-peer sharing of experiential data, and other bodies of user-generated data. For example, patientslikeme.com includes data from individuals with various ailments who post information about themselves including, for example, disease, diagnosis date, symptoms, medications taken (including dosage and length of time), outcome data, geographical location, and the like. Disease-specific patient experience registries also exist online. For example, ALSconnection.com or ALSconnection is a patient-driven ALS registry serving to collect data from ALS patients in North America.

A standard of care database 210 may include patient care standards from health care organizations such as the American Medical Association, American College of Physicians, and the National Library of Medicine. Patient care guidelines may suggest a treatment for a given condition, for example, according to the New England Journal of Medicine (2004), adjuvant chemotherapy for lung cancer is a new standard of care. One online source of standard of care guidelines can be found at guideline.gov, which is the site of the United States government's National Guideline Clearinghouse. Searches can be conducted at this site to find, for example, standard of care guidelines for cancer prevention, nutrition, screening, and treatment.

It should be recognized that treatment planning module 104 is not limited to treatment planning; treatment planning module 104 may also plan prevention, testing, or other steps in addressing a health-related status of an individual.

Operation 330 depicts providing a matching system for procurement of a desired health service option. For example, device 102 and/or health care services matching unit 120, upon accepting a selected health-related services option from user 140, may solicit bids from potential service providers 160. In the pancreatic cancer example above, a user 140 may select laparoscopy with biopsy as the health care services option from among those determined by treatment planning module 104, for example. Based on this selection, health care services matching unit 120 may contact service provider(s) 160 to find capable and/or available service providers. In some embodiments, health care services matching unit 120 may limit contacts to those service providers 160 that satisfy a given user preference, such as geographic location, cost level, quality ranking, or the like. Health care services matching unit 120 may include a service provider database 222, a sole source selection unit 224, an auction unit, an arbitrage unit 228, and/or a user preference database 230. In some embodiments, service providers 160 may be invited to bid for a contract to provide a health care service, resulting in a low cost health care service for user 140.

For example, in the case where a user 140 selects laparoscopy with biopsy as a desired screening procedure for suspected pancreatic cancer, health care services matching unit 120 may conduct an auction among local oncologists, resulting in a match with a local oncologist that is convenient and affordable to the user 140 and/or affordable to the insurer of user 140. In an alternative embodiment, health care services matching unit 120 may restrict service providers 160 to those having national recognized oncology screening and/or treatment services, based on an expressed preference of user 140.

In yet another embodiment, treatment planning module 104 may accept "Huntingdon's chorea" an indication of at least one health-related status of an individual, and "doctors within 50 miles of Abilene, Tex." as a user preference datum. Treatment planning module 104 may accordingly determine that there is only one doctor specializing in Huntingdon's chorea testing and/or treatment within 50 miles of Abilene, Tex. In one embodiment, a default setting may direct the device 102, health care services matching unit, and/or sole source selection unit 224 to match the one doctor able to provide the health service option with the user 140 as a way of providing a matching system for procurement of a desired health service option. In one embodiment, a default setting may allow for matching with no input from user 140 other than the initial indication of at least one health-related status of an individual.

Figure 4:
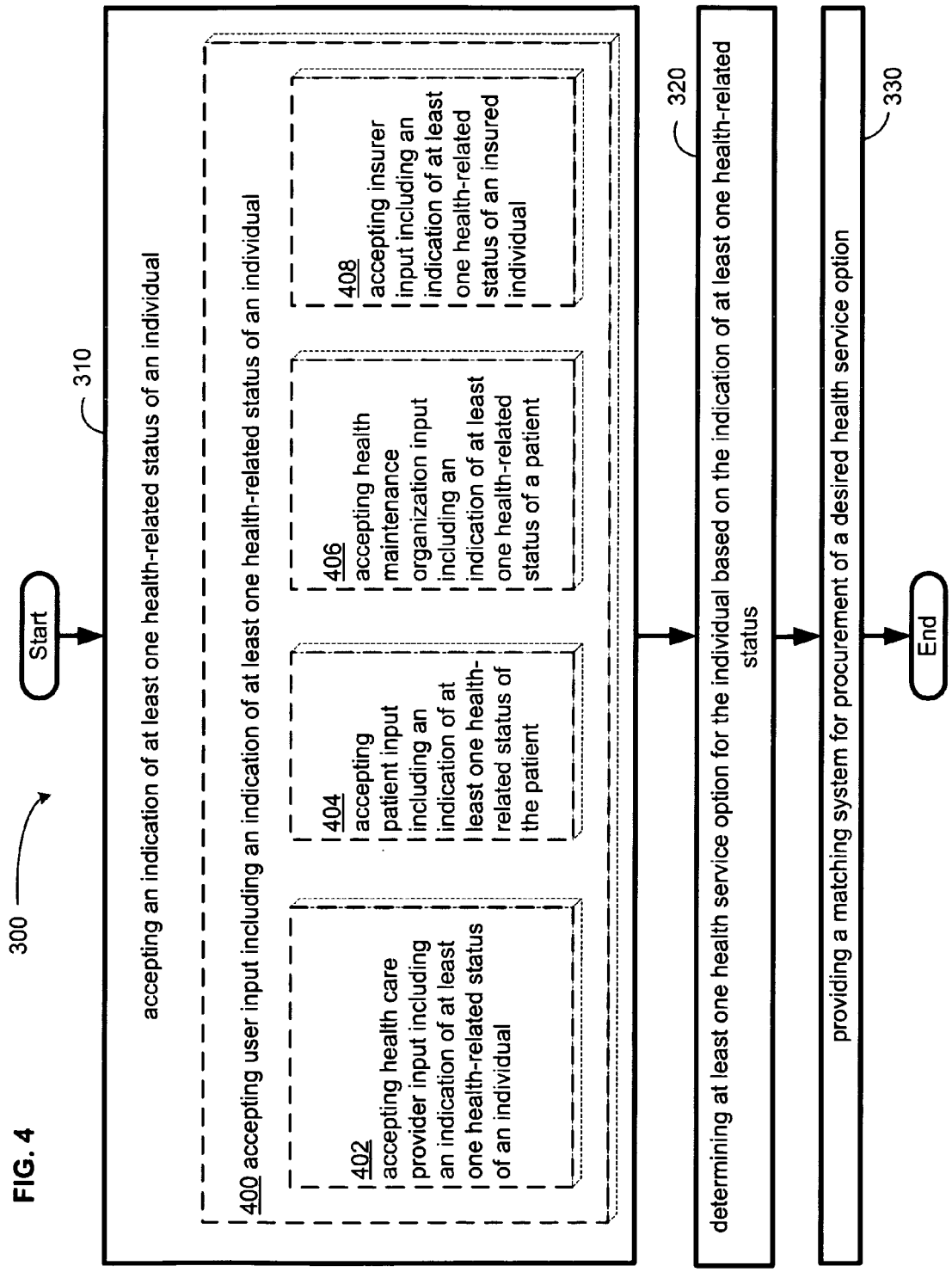
FIG. 4 illustrates an alternative embodiment of the operational flow of FIG. 3.

FIG. 4 illustrates alternative embodiments of the example operational flow 300 of FIG. 3. FIG. 4 illustrates example embodiments where the accepting operation 310 may include at least one additional operation. Additional operations may include operation 400, 402, 404, 406, and/or operation 408.

Operation 400 depicts accepting user input including an indication of at least one health-related status of an individual. For example, device 102 and/or treatment planning module 104 may accept user input including an indication of at least one health-related status of an individual. For example, treatment planning module 104 may accept from user 140 a symptom, a disease name, a diagnosis name, a health service procedure name, or the like. Virtually any health-related term may be accepted; each health-related term will serve as an indication of at least one health-related status of the individual. For example, accepting user input in the form of "facelift" may be an indication of a desire for cosmetic surgery. This may be used to determine health care services options for facelift services including treatment centers. Specific options for service providers including plastic surgeons, hospitals, plastic surgery resorts, or the like may also be determined. Options other than plastic surgery may also be determined based on this user input, such as peels, dermabrasion, or the like.

As used herein, the term "user" may include anyone using the system 100 to determine health services options and to obtain an appropriate service provider. For example, user 140 may include an individual experiencing discomfort that may be a symptom of a disease. Alternatively, the user 140 may be a patient looking for next steps in her treatment and/or in need of a new doctor and/or a second opinion. In another embodiment, the user 140 may be a health care provider, such as a general practice doctor or a primary care provider, who may be a doctor, a nurse practitioner, a physician assistant, an alternative medicine practitioner or the like, who wants to find a referral for a patient in need of a specialist. In yet another embodiment, the user 140 may include an insurer wanting to find a low-cost health services provider in a certain geographic region for an insured individual or group of individuals.

Operation 402 depicts accepting health care provider input including an indication of at least one health-related status of an individual. For example, device 102 and/or treatment planning module 104 may accept health care provider input including an indication of at least one health-related status of an individual. For example, an internist may input "type II diabetes" for a specialist to refer a patient newly diagnosed with diabetes. In cases of difficult diagnoses, a set of symptoms may be entered by a physician and an optional medical expert system function in the treatment planning module 104 may be accessed to generate a list of possible diagnoses for the symptom set. In one embodiment, a set of specialists with whom to consult may be determined by the device 102 and/or treatment planning module 104.

Operation 404 depicts accepting patient input including an indication of at least one health-related status of the patient. For example, device 102 and/or treatment planning module 104 may accept patient input including an indication of at least one health-related status of the patient. For example, a diabetes patient may input "type II diabetes" when looking for an endocrinologist to provide care for her condition. In some embodiments, a set of symptoms may be entered by a patient, and an optional medical expert system function in the treatment planning module 104 may be accessed to generate a list of possible diagnoses for the symptom set, and/or health care providers capable of providing an appropriate service. For example, if a patient enters skin rash, fever, and neck stiffness, device 102 and/or treatment planning module 104 may list meningitis as one possible diagnosis for the patient. Such a patient may be merely experiencing symptoms and not yet under the care of a health care provider.

Operation 406 depicts accepting health maintenance organization input including an indication of at least one health-related status of a patient. For example, device 102 and/or treatment planning module 104 may accept health maintenance organization input including an indication of at least one health-related status of a patient. For example, a health maintenance organization may input "carpal tunnel syndrome" to find physical therapists providing services for patients with this condition. If the health care maintenance organization then chooses a particular determined health service option, such as stretching exercises and application of a wrist brace, a geographical preference may be entered such that the device 102 and/or health care services matching unit 120 can find one or more appropriate health care providers of carpal tunnel therapy in the desired geographic area.

Operation 408 depicts accepting insurer input including an indication of at least one health-related status of an insured individual. For example, device 102 and/or treatment planning module 104 may accept insurer input including an indication of at least one health-related status of an insured individual. For example, an insurer may input "congestive heart failure" to identify risk factors for congestive heart failure among individuals in a general population or a subpopulation. In one embodiment, treatment planning module 104 may determine that coronary artery disease, smoking, diabetes, hypertension, and high cholesterol are significant risk factors for congestive heart failure among individuals aged 55 to 85 in the United States. Stress-test monitoring of coronary artery disease may be identified as one of the options for congestive heart failure prevention, and upon selection of this option by insurer 272, local cardiologists may be invited to provide competitive rates for providing stress tests to insured individuals.

Figure 5:
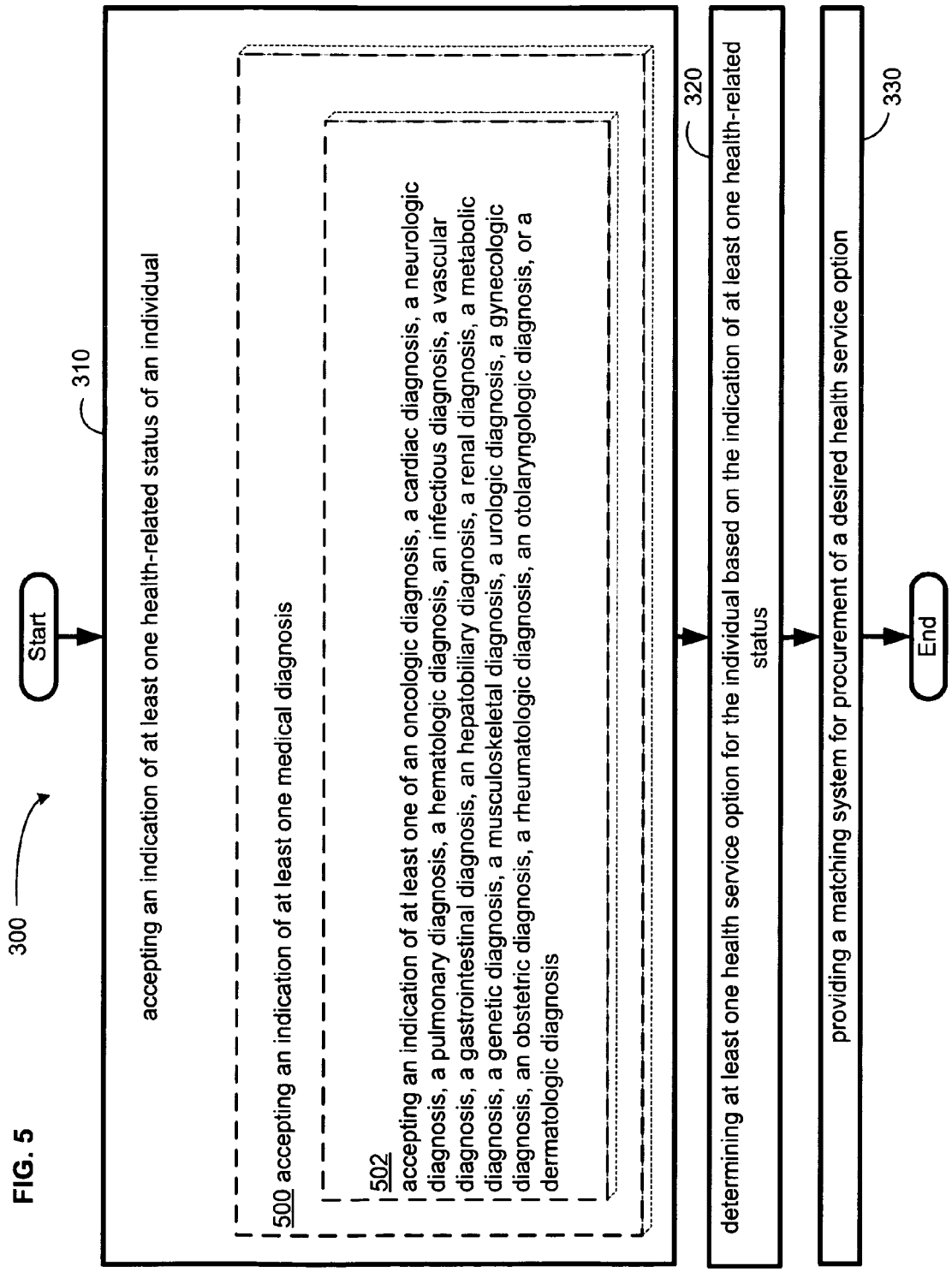
FIG. 5 illustrates an alternative embodiment of the operational flow of FIG. 3.

FIG. 5 illustrates alternative embodiments of the example operational flow 300 of FIG. 3. FIG. 5 illustrates example embodiments where the accepting operation 310 may include at least one additional operation. Additional operations may include operation 500 and/or operation 502.

Operation 500 depicts accepting an indication of at least one medical diagnosis. For example, device 102 and/or treatment planning module 104 may accept an indication of at least one medical diagnosis. For example, an individual may input "glaucoma" to determine treatment steps to take once a diagnosis is received. Often a physician will recommend a course of treatment upon making a diagnosis, but a patient may also want to know about alternative treatments, including alternatives to Western medical treatment. In this example of a glaucoma diagnosis, treatment planning module 104 may determine medical treatment options including beta blockers, prostaglandin analogs, alpha-adrenergic agonists, carbonic anhydrase inhibitors, as well as alternative treatment options including aerobic exercise, marijuana therapy and/or acupuncture therapy.

Operation 502 depicts accepting an indication of at least one of an oncologic diagnosis, a cardiac diagnosis, a neurologic diagnosis, a pulmonary diagnosis, a hematologic diagnosis, an infectious diagnosis, a vascular diagnosis, a gastrointestinal diagnosis, an hepatobiliary diagnosis, a renal diagnosis, a metabolic diagnosis, a genetic diagnosis, a musculoskeletal diagnosis, a urologic diagnosis, a gynecologic diagnosis, an obstetric diagnosis, a rheumatologic diagnosis, an otolaryngologic diagnosis, or a dermatologic diagnosis. For example, device 102 and/or treatment planning module 104 may accept an indication of at least one of an oncologic diagnosis, a cardiac diagnosis, a neurologic diagnosis, a pulmonary diagnosis, a hematologic diagnosis, an infectious diagnosis, a vascular diagnosis, a gastrointestinal diagnosis, an hepatobiliary diagnosis, a renal diagnosis, a metabolic diagnosis, a genetic diagnosis, a musculoskeletal diagnosis, a urologic diagnosis, a gynecologic diagnosis, an obstetric diagnosis, a rheumatologic diagnosis, an otolaryngologic diagnosis, or a dermatologic diagnosis. For example, an caretaker may input "Alzheimer's disease" as a neurologic diagnosis to determine treatment steps to take once an Alzheimer's diagnosis is received. Often a person caring for an individual with Alzheimer's will not know what to do or where to turn for help in caring for the affected individual. Inputting "Alzheimer's disease" into the treatment planning module 104, for example, may result in a determination of treatment options including drug therapy, e.g., including memantine, glantamine, rivastigmine, doenpezil, and/or tacrine; and/or non-pharmacological behavioral-management approaches such as playing music of the person's choosing, one-on-one interaction, playing videotapes of family members, walking and light exercise, and pet therapy.

Figure 6:
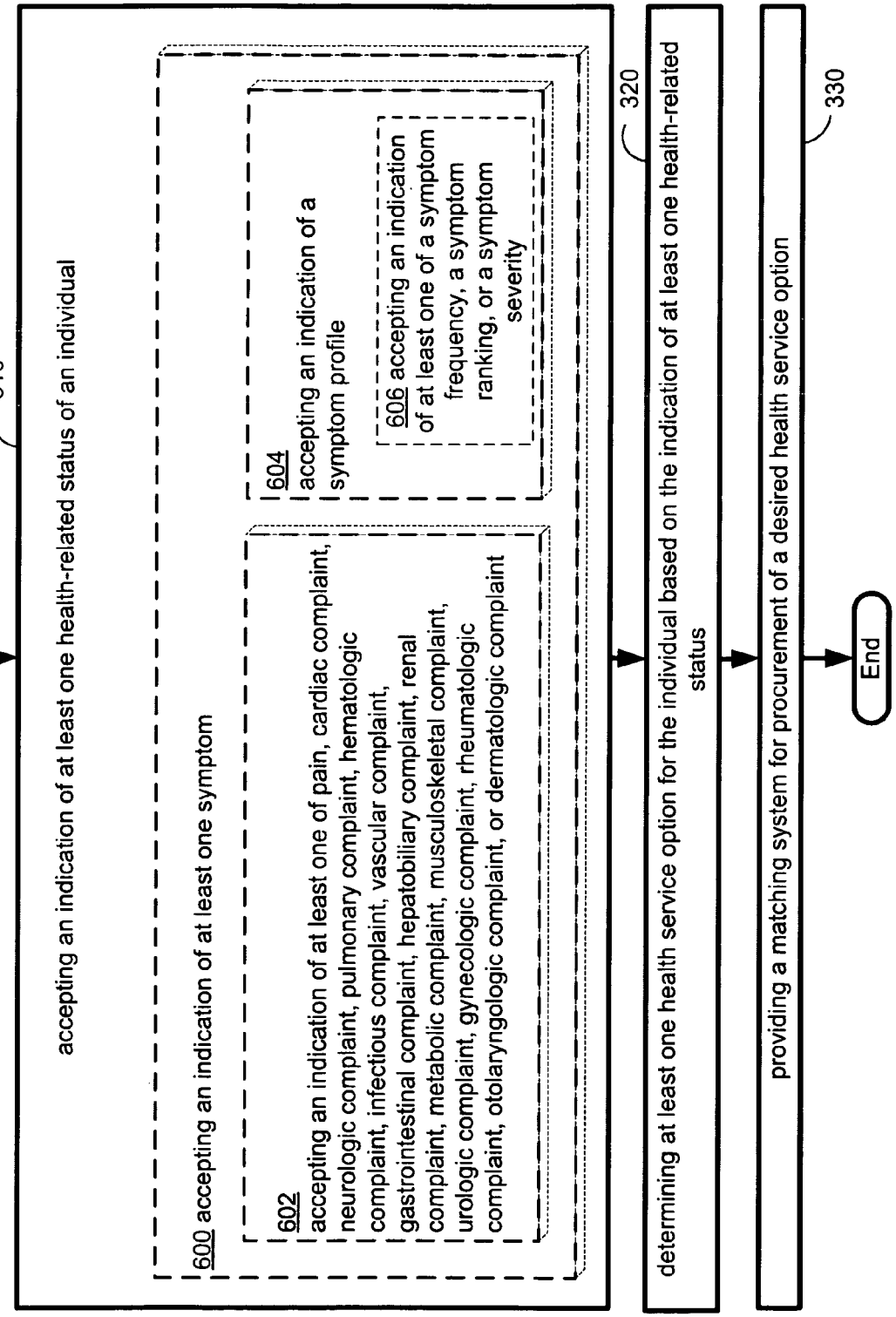
FIG. 6 illustrates an alternative embodiment of the operational flow of FIG. 3.

FIG. 6 illustrates alternative embodiments of the example operational flow 300 of FIG. 3. FIG. 6 illustrates example embodiments where the accepting operation 310 may include at least one additional operation. Additional operations may include operation 600, 602, 604, and/or operation 606.

Operation 600 depicts accepting an indication of at least one symptom. For example, device 102 and/or treatment planning module 104 may accept an indication of at least one symptom. In one embodiment, treatment planning module 104 may accept a symptom such as "decreased night vision." Treatment planning module 104 may then determine a set of testing and treatment steps including, for example, one testing step may be to look at decreased night vision as a side effect of various medicines. Another testing step may include cataract testing, such as a refraction test, a slitlamp exam, a contrast sensitivity test, a glare disability test, a potential acuity test, a dilated fundus exam, or the like. Treatment options for cataracts may also be determined at this time. Alternatively, user 140 may opt to defer listing of treatment options until a diagnosis is obtained based on the testing options presented. In this scenario, if the user 140 discovers that she has cataracts, treatment options including surgery may be determined and presented to user 140.

Operation 602 depicts accepting an indication of at least one of pain, cardiac complaint, neurologic complaint, pulmonary complaint, hematologic complaint, infectious complaint, vascular complaint, gastrointestinal complaint, hepatobiliary complaint, renal complaint, metabolic complaint, musculoskeletal complaint, urologic complaint, gynecologic complaint, rheumatologic complaint, otolaryngologic complaint, or dermatologic complaint. For example, device 102 and/or treatment planning module 104 may accept an indication of at least one of pain, cardiac complaint, neurologic complaint, pulmonary complaint, hematologic complaint, infectious complaint, vascular complaint, gastrointestinal complaint, hepatobiliary complaint, renal complaint, metabolic complaint, musculoskeletal complaint, urologic complaint, gynecologic complaint, rheumatologic complaint, otolaryngologic complaint, or dermatologic complaint. In one embodiment, treatment planning module 104 may accept "earache" as an otolaryngologic complaint. In this example, treatment planning module may determine an otoscope examination to diagnose infection of the outer or middle ear (e.g., otitis externa or otitis media), and treatment steps including antibiotic ear drops in the case of otitis externa, and/or oral antibiotics in the case of otitis media. Upon selection of a desired determined examination and/or treatment, health care services matching unit may search a health care services provider database for a list of those providers with expertise in the ear/nose/throat specialty and with offices in the geographic area near the user 140. The resulting subset of local ear/nose/throat specialists may then be invited to bid on the cost of services for examination and/or treatment of user 140, thereby providing a matching system for procurement of the desired health service option.

Operation 604 depicts accepting an indication of a symptom profile. For example, device 102 and/or treatment planning module 104 may accept an indication of a symptom profile. In one embodiment, treatment planning module 104 may accept a constellation of symptoms that suggests a diagnosis, such as a set of typical symptoms of a known disease. See, e.g., U.S. patent publication 2008/0091086. For example, treatment planning module 104 may accept a set of one or more of the following symptoms: bull's-eye rash, fever, stiff neck, headache, body aches, fatigue, or redness and swelling in the joints. Based on such a constellation of symptoms, testing and/or treatment for Lyme disease may be determined.

Operation 606 depicts accepting an indication of at least one of a symptom frequency, a symptom ranking, or a symptom severity. For example, device 102 and/or treatment planning module 104 may accept an indication of at least one of a symptom frequency, a symptom ranking, or a symptom frequency and severity. In one embodiment, treatment planning module 104 may accept an indication of asthma symptom severity. The National Asthma Education Program, which produces the U.S.-based asthma treatment guidelines, classifies asthma by its severity, a scheme commonly used by most health professionals. This approach also guides asthma treatment.

Classification of asthma by severity is based on frequency and severity of asthma symptoms, along with peak flow readings. Levels are referred to as steps, as follows: Step 1: Mild Intermittent; at this level, asthma symptoms occur less than 2 times a week during waking hours and less than twice a month during the night. In between asthma attacks, no symptoms occur at all, and the attacks themselves are generally brief, though their intensity can vary. Peak flow variability is less than 20 percent. Step 2: Mild Persistent; at this level, asthma symptoms occur more than twice a week, but not as often as daily. They may occasionally wake one up at night, but that happens less than 2 times a month. Asthma attacks may interfere with activity temporarily. Peak flow tends to be between 20 and 30 percent. Step 3: Moderate Persistent; at this level, asthma begins to interfere more with daily living. Symptoms are seen every single day, and use of a quick-relief inhaler daily may be required. Asthma attacks occur at least twice a week and often interfere with activity. They may last for days at a time. Individuals may wake up 1 or more times a week with symptoms. Peak flow rate varies by more than 30 percent. Step 4: Severe Persistent; this is the most severe form of asthma and at this level, symptoms are basically continuous. Activity is severely limited and asthma attacks and night symptoms are frequent. Peak flow varies by more than 30 percent.

The National Asthma Education Program advocates a stepwise approach to treating asthma in adults and children older than age 5, based on the types of asthma severity described above. For instance, mild intermittent asthma is usually treated only with quick-relief medicines, while severe persistent asthma is treated with one or more daily controller medicines and frequent use of quick-relief medicines. Accordingly, treatment planning module 104 may present appropriate treatment options for each type of asthma.

Symptom ranking may include priority rankings of symptoms, such as those experienced with gastrointestinal reflux disease (GERD). Heartburn, regurgitation, and dysphagia are considered typical symptoms of GERD. For example, it has been shown that high priority ranking of the symptom dysphagia is predictive of the presence of an esophageal stricture, but has a negative association with abnormal manometric and pH studies. In contrast, high priority ranking of the symptom heartburn and regurgitation are positively associated with abnormal manometric and pH results. See Martinez-Serna et al., "Symptom Priority Ranking in the Care of Gastroesophageal Reflux: A Review of 1,850 Cases," Dig Dis, 17:219-224 (1999).

Figure 7:
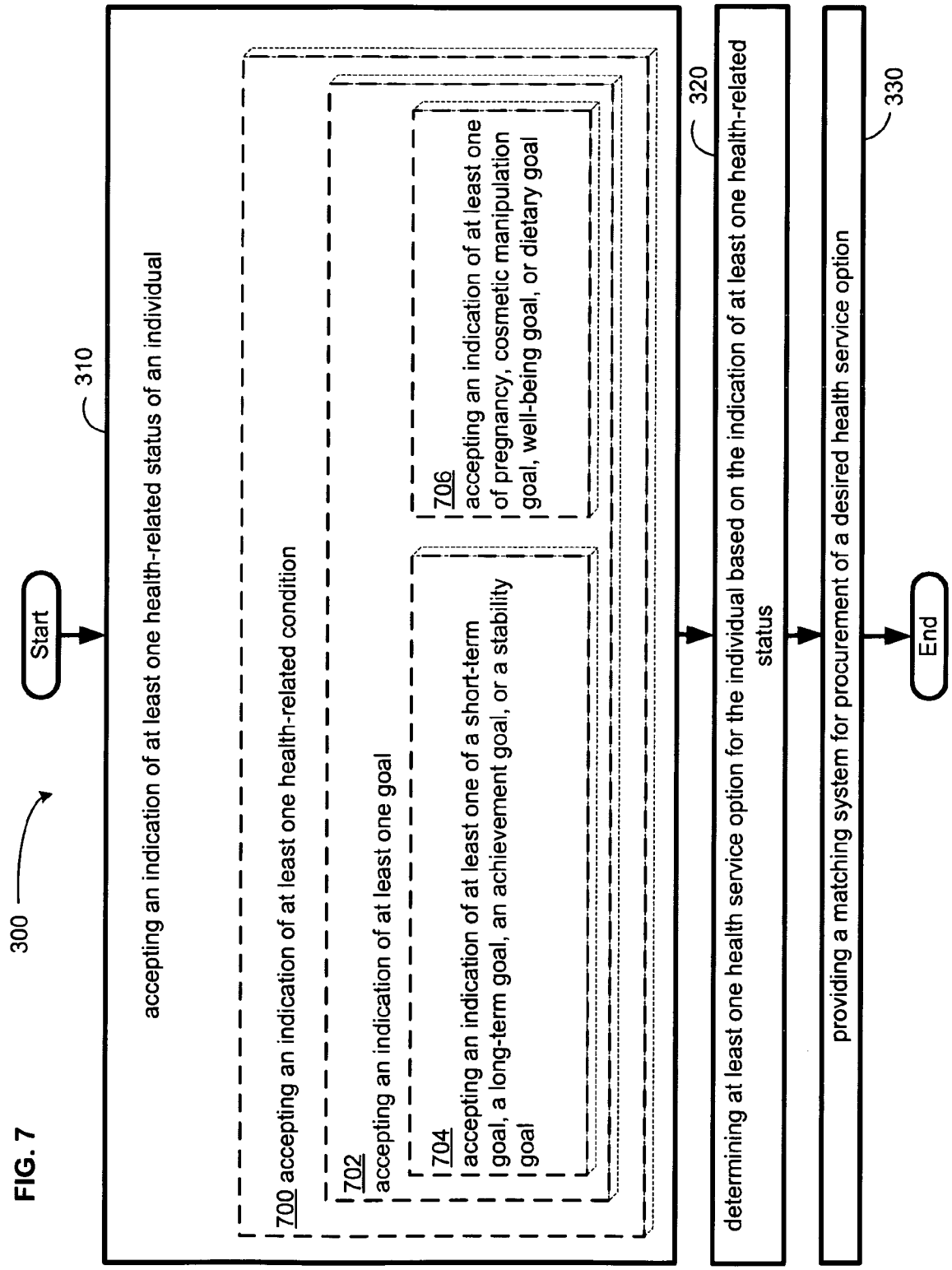
FIG. 7 illustrates an alternative embodiment of the operational flow of FIG. 3.

FIG. 7 illustrates alternative embodiments of the example operational flow 300 of FIG. 3. FIG. 7 illustrates example embodiments where the accepting operation 310 may include at least one additional operation. Additional operations may include operation 700, 702, 704, and/or operation 706.

Operation 700 depicts accepting an indication of at least one health-related condition. For example, device 102 and/or treatment planning module 104 may accept an indication of at least one health-related condition. In one embodiment, treatment planning module 104 may accept an indication of a health-related condition such as "weight-loss." In such a case, treatment planning module 104 may determine evaluative and treatment services such as nutritionist services or dietetics services. Nutraceutical options may also be determined.

Operation 702 depicts accepting an indication of at least one goal. For example, device 102 and/or treatment planning module 104 may accept an indication of at least one goal. In one embodiment, treatment planning module 104 may accept an indication of an athletic performance goal, such as increased aerobic conditioning. Determined health service options for this goal may include exercise training services, nutrition services, sports psychology services, or the like.

Operation 704 depicts accepting an indication of at least one of a short-term goal, a long-term goal, an achievement goal, or a stability goal. For example, device 102 and/or treatment planning module 104 may accept an indication of at least one of a short-term goal, a long-term goal, an achievement goal, or a stability goal. In one embodiment, treatment planning module 104 may accept an achievement goal, such as stopping smoking cigarettes. In this example, treatment planning module 104 may determine nicotine replacement therapy, such as over-the-counter anti-smoking aids such as nicotine gum. Another nicotine replacement therapy is the nicotine patch. Other alternatives to combat the urge to smoke include support and counseling services, hypnosis, acupuncture, or the like.

A stability goal may include maintenance programs whereby an individual is able to achieve a goal with a degree of consistency over time. For example, a stability goal for a diabetic may include maintaining her blood sugar within a recommended range for a given period of months or years. Another example of a stability goal is maintaining one's LDL cholesterol at a low level over a certain period of time.

Operation 706 depicts accepting an indication of at least one of pregnancy, cosmetic manipulation goal, well-being goal, or dietary goal. For example, device 102 and/or treatment planning module 104 may accept an indication of at least one of pregnancy, cosmetic manipulation goal, well-being goal, or dietary goal. In one embodiment, treatment planning module 104 may accept an indication of "rhinoplasty" as the cosmetic manipulation goal. In this embodiment, treatment planning module 104 may determine various rhinoplasty options, including, for example, open rhinoplasty, closed rhinoplasty, or non-surgical rhinoplasty. In some situations, a patient/health care provider/user 140 may not be aware of the range of options available for addressing a given health-related status or health-related condition. Accordingly, the system 100, device 102, and/or treatment planning module 104 may be useful to the user 140 in terms of discovering a range of options available to pursue.

Examples of a pregnancy goal include a goal for becoming pregnant within a certain time frame, a goal for overcoming male or female infertility, a goal for ending a pregnancy, or the like. Examples of a well-being goal include a goal for stress management, a goal for depression management, a goal for sleeplessness management, a goal for anxiety management, or the like. Examples of a dietary goal include a goal for weight loss, a goal for a lower body mass index, a goal for increased muscle mass, a goal for lower dietary cholesterol intake, a goal for a diabetes-compatible diet, or the like.

Figure 8:
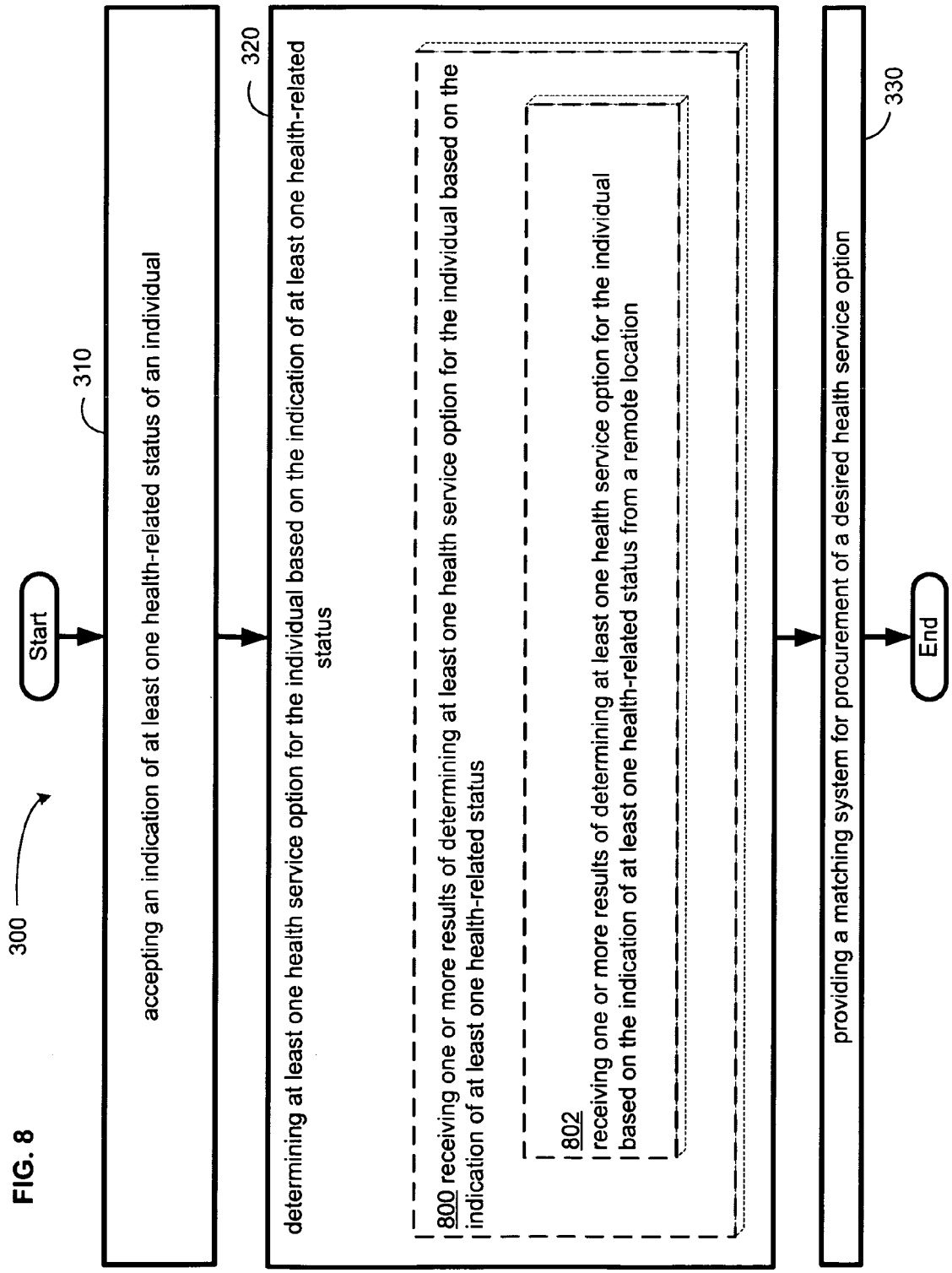
FIG. 8 illustrates an alternative embodiment of the operational flow of FIG. 3.

FIG. 8 illustrates alternative embodiments of the example operational flow 300 of FIG. 3. FIG. 8 illustrates example embodiments where the determining operation 320 may include at least one additional operation. Additional operations may include operation 800 and/or operation 802.

Operation 800 depicts receiving one or more results of determining at least one health service option for the individual based on the indication of at least one health-related status. For example, device 102 and/or treatment planning module 104 may receive one or more results of determining at least one health service option for the individual based on the indication of at least one health-related status. In one embodiment, treatment planning module 104 may receive a set of treatment options for multiple sclerosis, the treatment options having been determined outside of the United States. In such an embodiment, treatment options are received by device 102 for subsequent processing, including, for example, matching a multiple sclerosis specialist with a user 140.

Operation 802 depicts receiving one or more results of determining at least one health service option for the individual based on the indication of at least one health-related status from a remote location. For example, device 102 and/or treatment planning module 104 may receive one or more results of determining at least one health service option for the individual based on the indication of at least one health-related status from a remote location. In one embodiment, treatment planning module 104 may receive one or more treatment options from a remote location, such as from a search of a database located in China (e.g., search results from a Chinese medicine database located in China).

Figure 9:
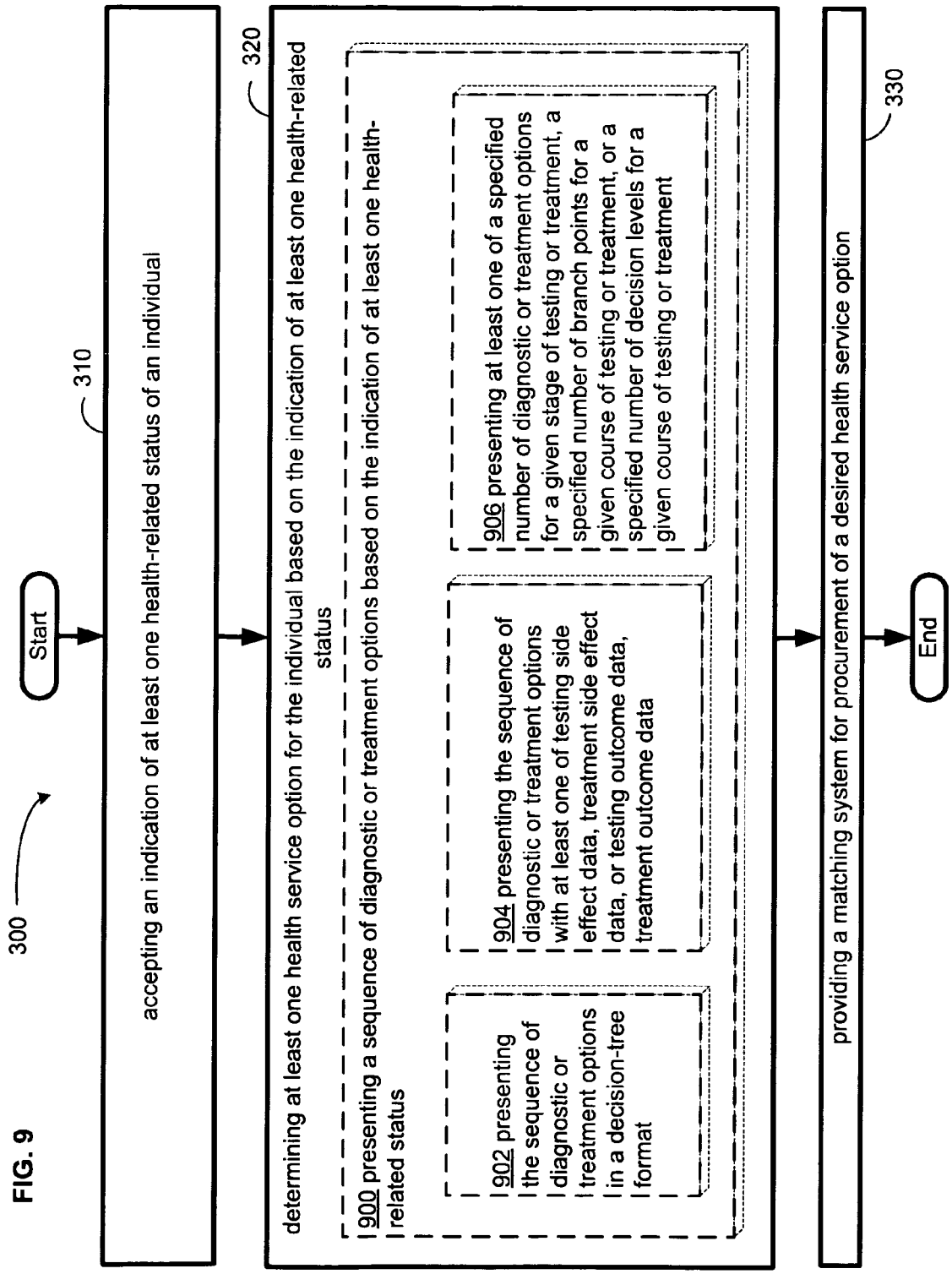
FIG. 9 illustrates an alternative embodiment of the operational flow of FIG. 3.

FIG. 9 illustrates alternative embodiments of the example operational flow 300 of FIG. 3. FIG. 9 illustrates example embodiments where the determining operation 320 may include at least one additional operation. Additional operations may include operation 900, 902, 904, and/or operation 906.

Figure 10:
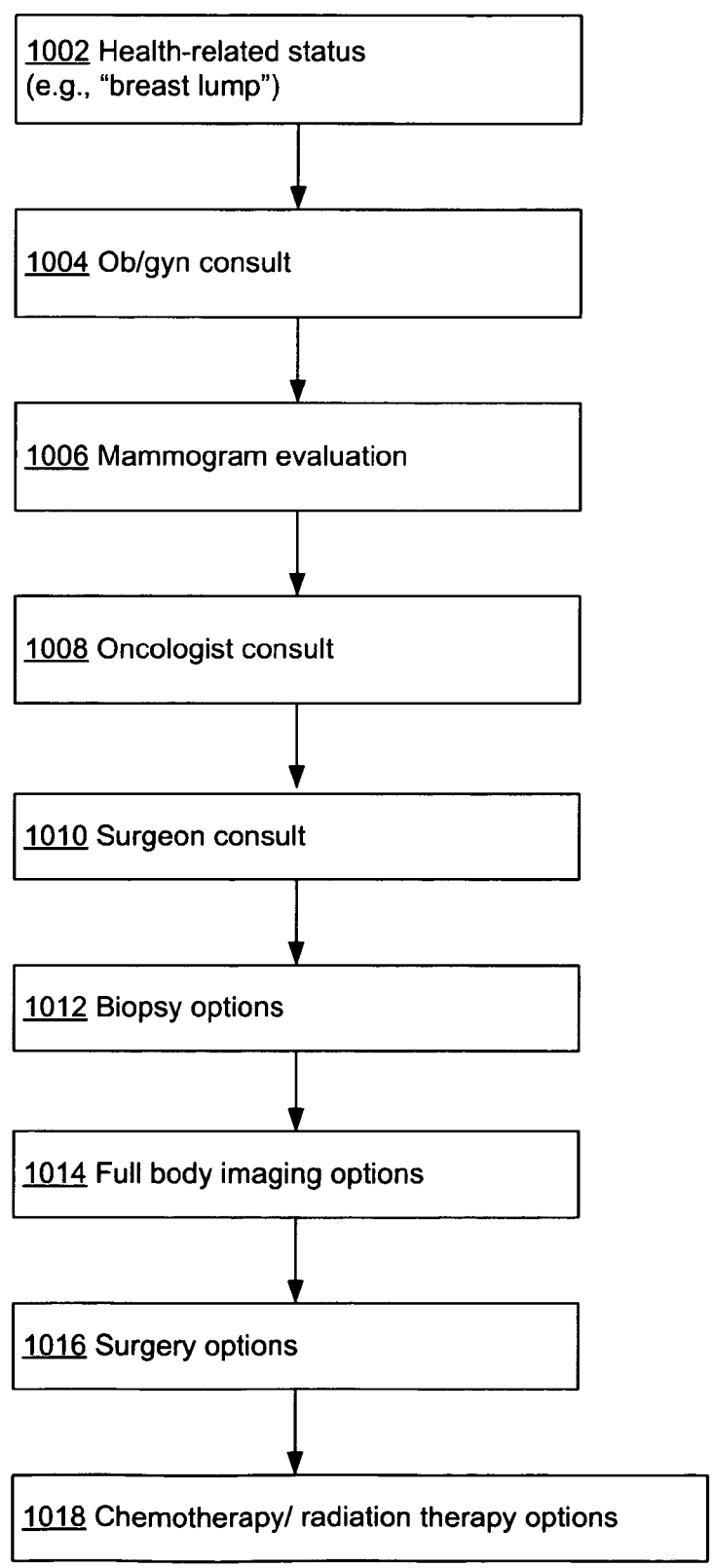
FIG. 10 illustrates an example of a sequence of determined health service options.

Operation 900 depicts presenting a sequence of diagnostic or treatment options based on the indication of at least one health-related status. For example, device 102 and/or treatment planning module 104 may present a sequence of diagnostic or treatment options based on the indication of at least one health-related status. In one embodiment, treatment planning module 104 can accept a sequence of treatment options for obesity, as shown in FIG. 10. FIG. 10 depicts a visualization of testing and treatment steps for system 100 accepting "breast lump" as an example of a health-related status 1002. A flow diagram may be determined and presented based on the accepted health-related status 1002, including a sequence of examinations and eventual treatment options. The list of sequential options may include service providers where appropriate, such as ob/gyn consult 1004, oncologist consult 1008, and surgeon consult 1010. This serves to identify for the user 140 potential service providers who may be required for providing care. Other sequential options include, for this example, mammogram evaluation 1006, biopsy options 1012, full body imaging options 1014 to investigate metastasis, surgery options 1016 perhaps including lumpectomy, partial mastectomy and full mastectomy, and chemotherapy/radiation therapy options 1018.

Figure 11:
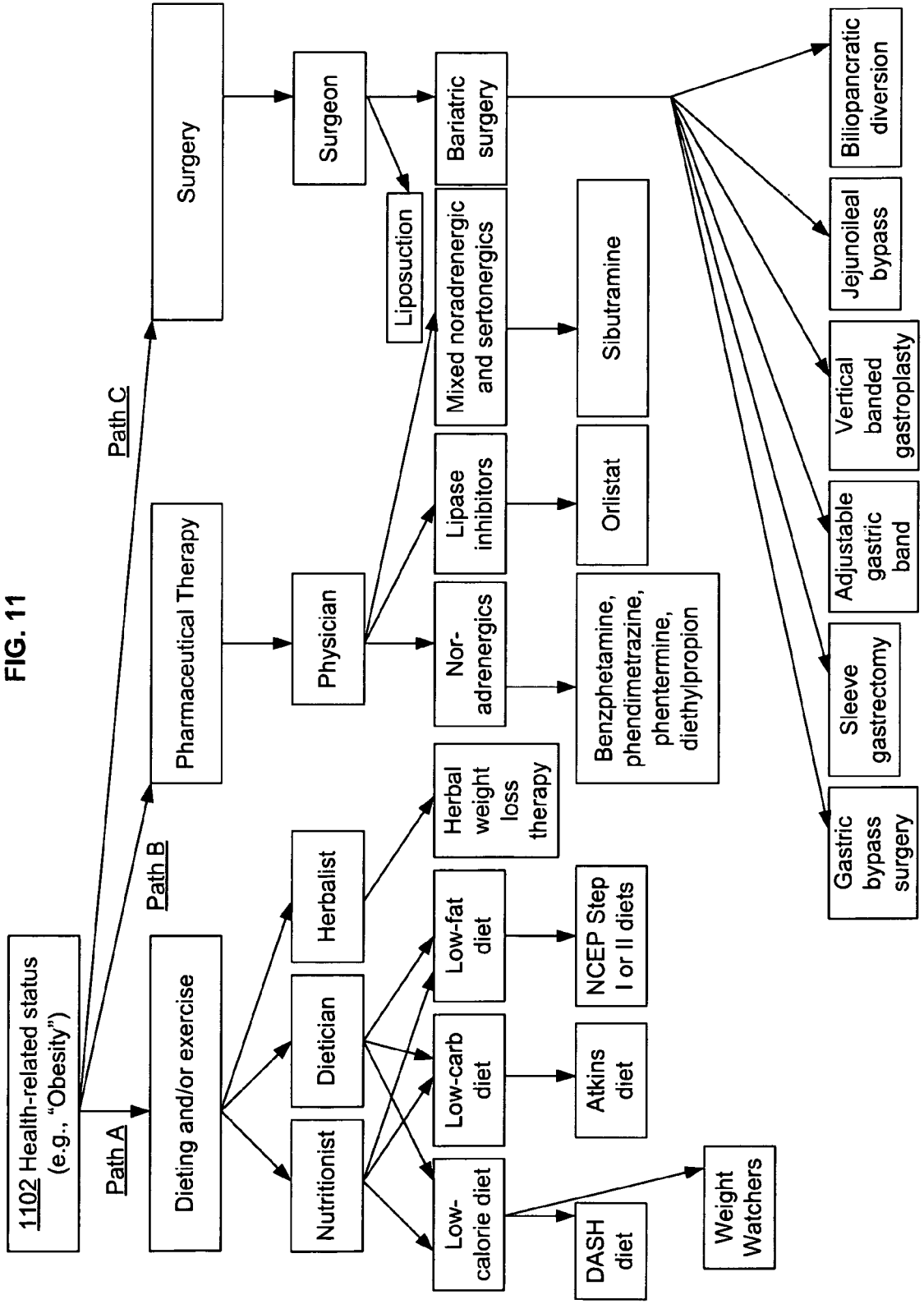
FIG. 11 illustrates an example of a decision tree of determined health service options.
Figure 12:
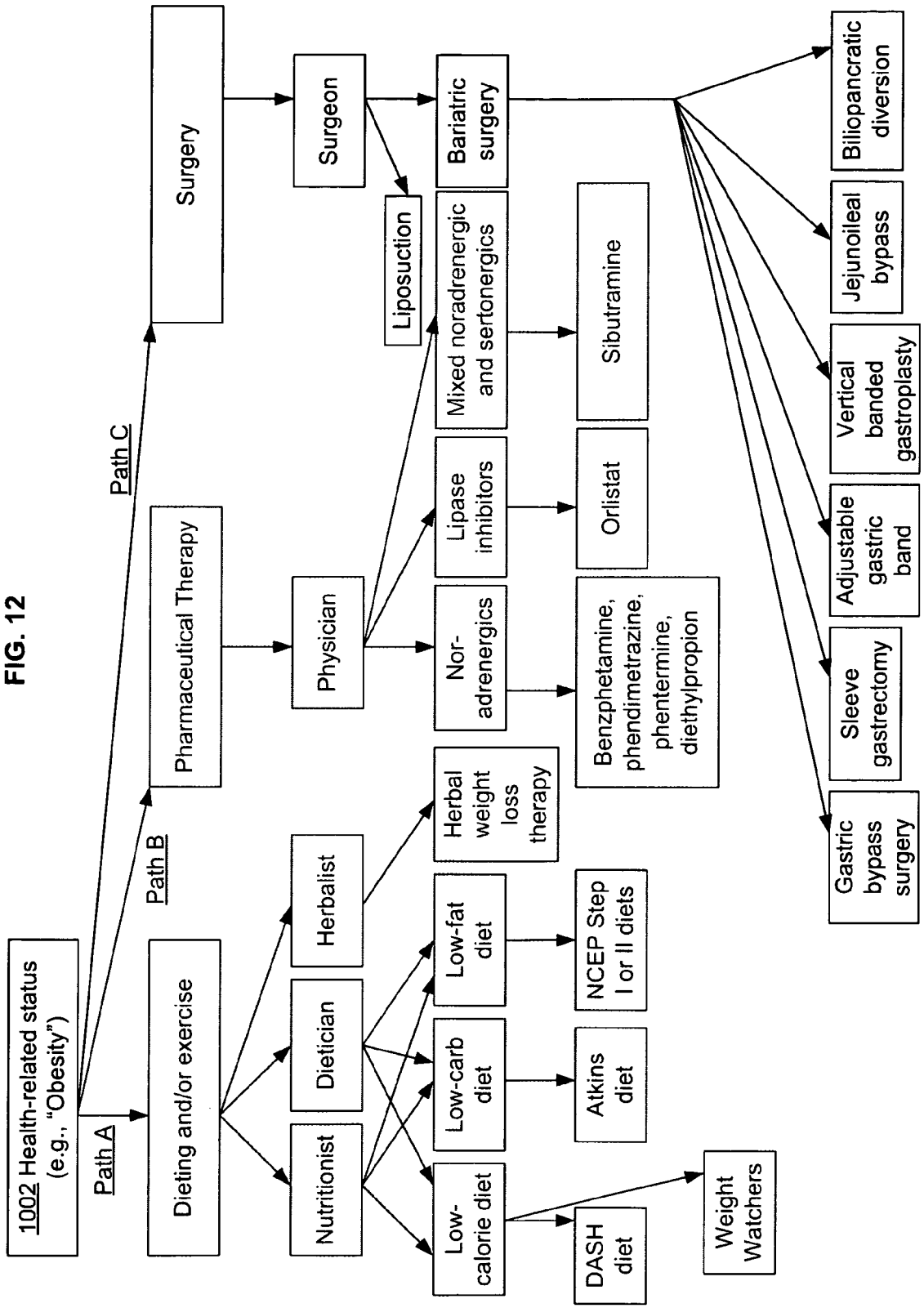
FIG. 12 illustrates an alternative visualization of the decision tree of determined health service options of FIG. 11.
Figure 13:
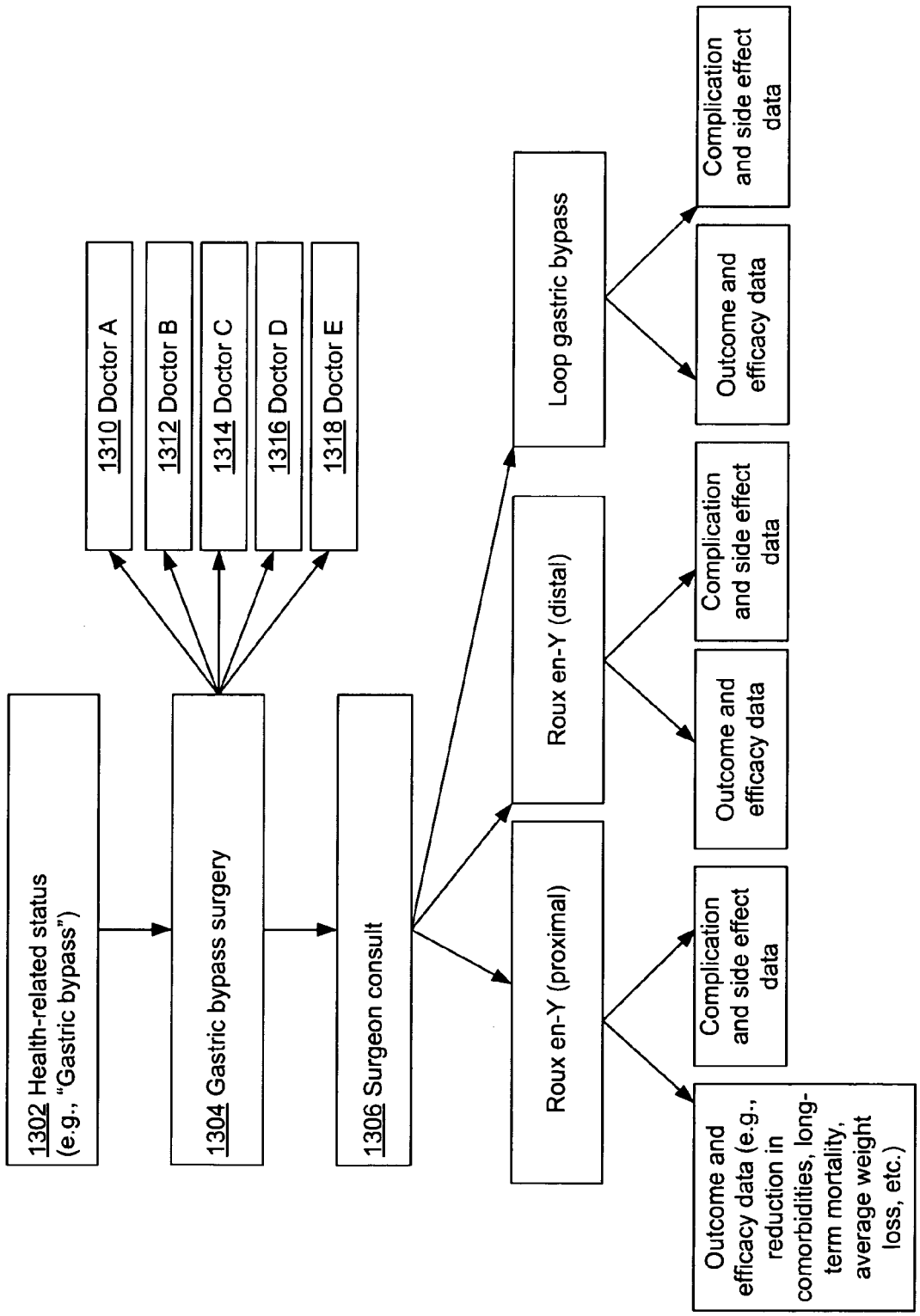
FIG. 13 illustrates an example of a decision tree of determined health service options.

Operation 902 depicts presenting the sequence of diagnostic or treatment options in a decision-tree format. For example, device 102 and/or treatment planning module 104 may present the sequence of diagnostic or treatment options in a decision-tree format. In one embodiment, treatment planning module 104 may present options to address "obesity" as a health-related status 1102. FIG. 11 depicts a decision-tree visualization of treatment options for the health-related status 1102, "obesity." Three treatment paths are depicted, dieting and/or exercise (Path A), pharmaceutical therapy (Path B), and surgery (Path C). Such a visualization shows the treatment paths from the general to the specific, including the kinds of service provider available for each path, specific interventions typically offered by the service providers, such as types and specific drugs available by prescription in the case of Path B. In the example of Path B, the information provided by treatment planning module 104 can inform a user 140 considering pharmaceutical therapy for obesity. That user 140 may use the information to contact a physician with questions about the various drugs listed/approved for treating obesity. In some embodiments, further information may be provided, for example, costs associated with various treatments, side effects associated with various treatments, success rates, or the like. In one embodiment, treatment planning module 104 can determine a decision tree showing medical treatments, for example as shown in FIGS. 11-13. Other examples of medical treatment decision trees can be found in U.S. Pat. No. 6,807,531, which is incorporated herein in its entirety.

Evaluation of health services options is discussed in depth in Goodman, Clifford S., "Introduction to Health Care Technology Assessment," available at http://www.nlm.nih.gov/nichsr/hta101/ta101_c1.html, (January 2004), which is incorporated by reference herein in its entirety. An example of evaluation of health services options including a specific decision tree can be found in "Cancer in Scotland: Radiotherapy Activity Planning for Scotland 2011-2015," available at http://www.scotland.gov.uk/Publications/2006/01/24131719/28, (2006), which is incorporated by reference herein in its entirety. An example of a decision tree in the alternative medicine context can be found at http://cam.utmb.edu/curriculum/cam-decision-tree.asp and in Frenkel et al., "An approach for integrating complementary-alternative medicine into primary care," Fam. Pract., 20(3), pp. 324-332 (2003).

FIG. 12 depicts a user interface embodiment wherein user 140 can highlight one path of options. In one embodiment, system 100 can accept feedback about a selected path such that additional information about that path can be provided. For example, if user 140 indicates interest in Path C in FIGS. 11 and 12, additional information about that Path can be provided by treatment planning module 104, for example, in the form of the flow shown in FIG. 13. FIG. 13 depicts treatment options determined by the health-related status 1302 "gastric bypass." This flow shows a required surgeon consult and several kinds of surgery that can be chosen.

Operation 904 depicts presenting the sequence of diagnostic or treatment options with at least one of testing side effect data, treatment side effect data, or testing outcome data, treatment outcome data. For example, device 102 and/or treatment planning module 104 may present the sequence of diagnostic or treatment options with at least one of testing side effect data, treatment side effect data, or testing outcome data, treatment outcome data. In one embodiment, treatment planning module 104 can show efficacy and/or side effect data for a given treatment option. In the example shown in FIG. 13, for each gastric surgery option shown, outcome and efficacy data is provided, as well as complication and side effect data. In this example, efficacy data may include improvement in long-term mortality rates, reduction in comorbidities, average weight loss, or the like. Complication and side effect data may include incidence of infection, nausea, pain, or the like.

Operation 906 depicts presenting at least one of a specified number of diagnostic or treatment options for a given stage of testing or treatment, a specified number of branch points for a given course of testing or treatment, or a specified number of decision levels for a given course of testing or treatment. For example, device 102 and/or treatment planning module 104 may present at least one of a specified number of diagnostic or treatment options for a given stage of testing or treatment, a specified number of branch points for a given course of testing or treatment, or a specified number of decision levels for a given course of testing or treatment. In one embodiment, treatment planning module 104 may present a maximum of three treatment options for a given stage of treatment, as shown in FIG. 11, Paths A and B (Path C goes beyond the limit of three treatment options at the bottom of the decision tree, showing six options). In another embodiment, shown in FIG. 10, one testing/treatment option is shown at each stage of testing/treatment. In this embodiment, several options are collapsed into one option box. For example, surgery options 1016 includes several options such as lumpectomy, partial mastectomy, and full mastectomy. These additional options can be shown if the user 140 so chooses. Benefits of limiting the number of options at each stage include making the decision tree more manageable to digest and understand in terms of presenting a big picture of a prospective course of testing and/or treatment. Conversely, expanding the number of options provides more information about the options available at each stage.

In yet another embodiment, treatment planning module 104 may present a specified number of decision levels for a given course of testing or treatment. For example, with respect to the testing and treatment program depicted in FIG. 10, a user 140 may choose to limit the decision levels presented to treatment options only, such that treatment planning module 104 may present decision level oncologist consult 1008 through chemotherapy/radiation therapy options 1018 only.

Figure 14:
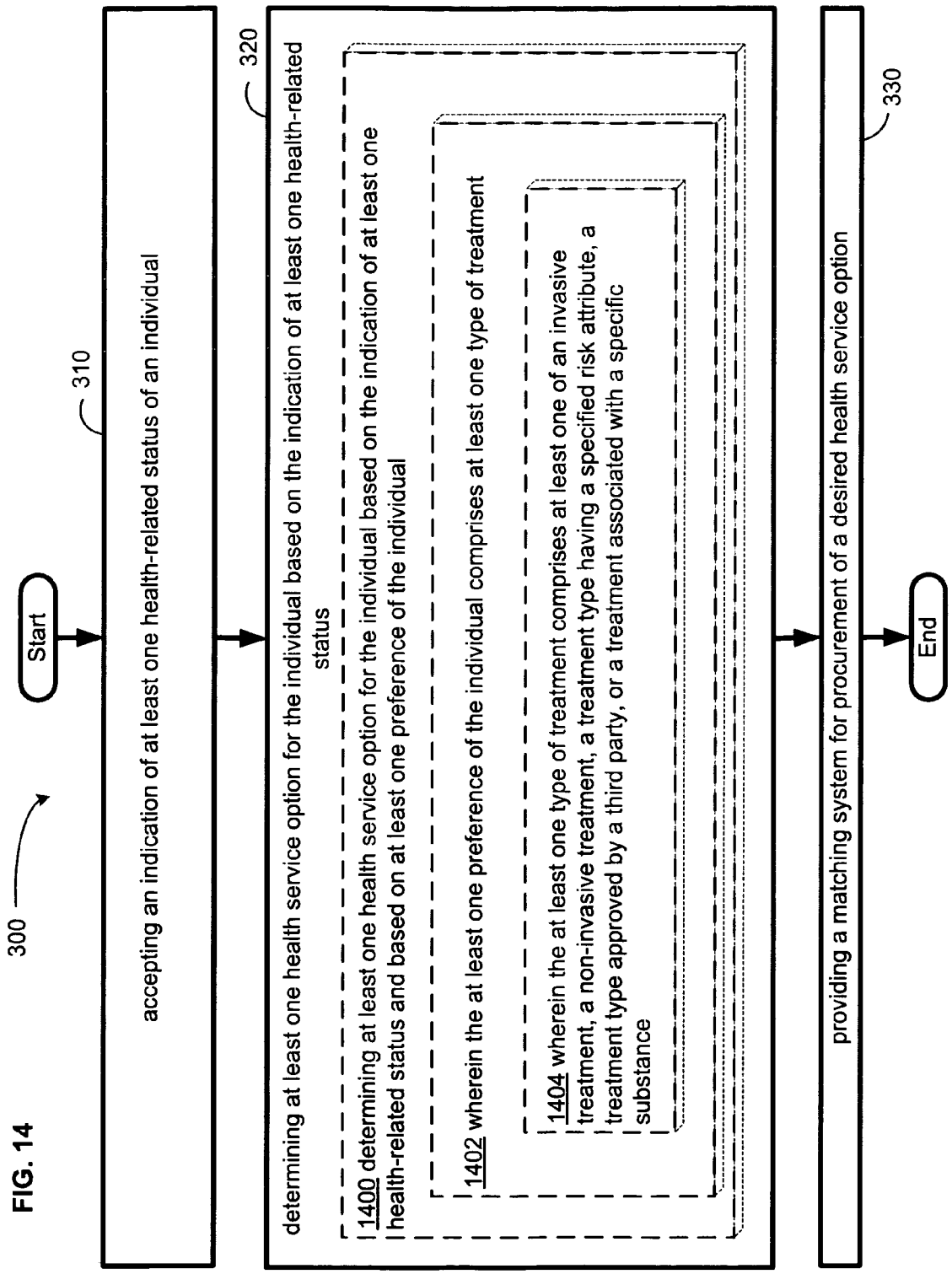
FIG. 14 illustrates an alternative embodiment of the operational flow of FIG. 3.

FIG. 14 illustrates alternative embodiments of the example operational flow 300 of FIG. 3. FIG. 14 illustrates example embodiments where the determining operation 320 may include at least one additional operation. Additional operations may include operation 1400, 1402, and/or operation 1404.

Operation 1400 depicts determining at least one health service option for the individual based on the indication of at least one health-related status and based on at least one preference of the individual. For example, device 102 and/or treatment planning module 104 may determine at least one health service option for the individual based on the indication of at least one health-related status and based on at least one preference of the individual. In one embodiment, treatment planning module 104 may determine, for example, a course of testing and/or treatment that takes into account one or more preferences or sensitivities of the individual, such as "treatments other than surgery," "local treatment options," "non-narcotic treatment options," or the like.

Operation 1402 depicts determining at least one health service option for the individual based on the indication of at least one health-related status and based on at least one type of treatment as the preference of the individual. For example, device 102 and/or treatment planning module 104 may determine at least one health service option for the individual based on the indication of at least one health-related status and based on at least one type of treatment as the preference of the individual. In one embodiment, treatment planning module 104 may determine a set of health service options for an individual based on a key word and an individual's preference of treatment type. In this example, consistent with the determined options of FIG. 10, a user 140 may specify a preference that excludes alternative medicine options, and/or that includes surgery options.

Operation 1404 depicts determining at least one health service option for the individual based on the indication of at least one health-related status and based on at least one of an invasive treatment, a non-invasive treatment, a treatment type having a specified risk attribute, a treatment type approved by a third party, or a treatment associated with a specific substance as the preference of the individual. For example, device 102 and/or treatment planning module 104 may determine at least one health service option for the individual based on the indication of at least one health-related status and based on at least one of an invasive treatment, a non-invasive treatment, a treatment type having a specified risk attribute, a treatment type approved by a third party, or a treatment associated with a specific substance as the preference of the individual. In one embodiment, treatment planning module 104 may access user preference data 212 in order to guide a determination of a health service option for the individual. For example, a user preference against surgery as an option for obesity may lead to a determination of Paths A and B in FIG. 11. In another example, treatment planning module 104 may access standard of care database 210 in order to determine health care options for treating obesity that are approved by, for example, the American Medical Association as a third party.

Figure 15:
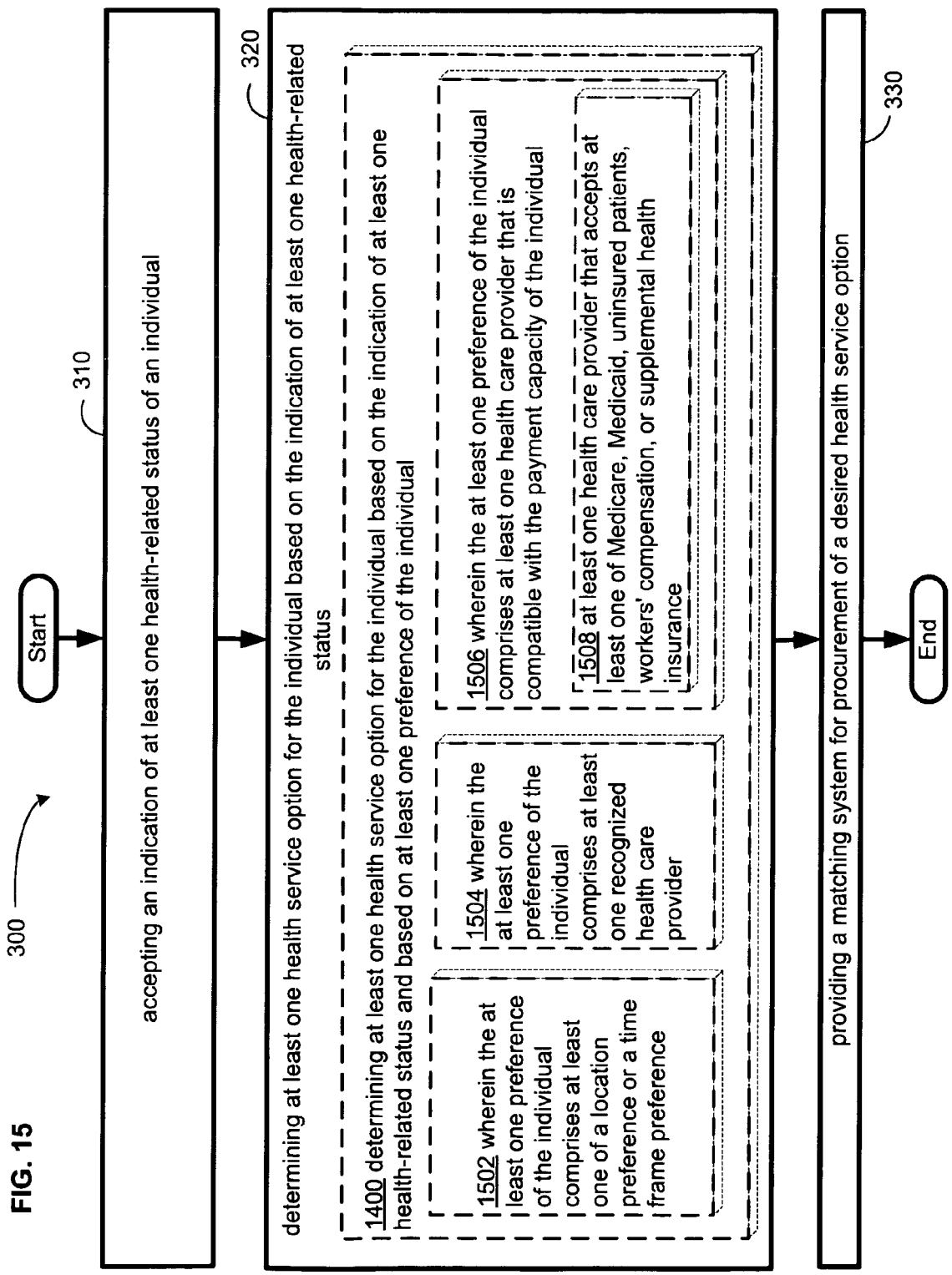
FIG. 15 illustrates an alternative embodiment of the operational flow of FIG. 3.

FIG. 15 illustrates alternative embodiments of the example operational flow 300 of FIG. 3. FIG. 15 illustrates example embodiments where the determining operation 320 may include at least one additional operation. Additional operations may include operation 1502, 1504, 1506, and/or operation 1508.

Operation 1502 depicts determining at least one health service option for the individual based on the indication of at least one health-related status and based on at least one of a location preference or a time frame preference. For example, device 102 and/or treatment planning module 104 may determine at least one health service option for the individual based on the indication of at least one health-related status and based on at least one of a location preference or a time frame preference. In one embodiment, treatment planning module 104 may determine at least one health service option based on a medical procedure such as "gastric bypass surgery" and a location such as "Miami-Dade County, Fla." As shown in FIG. 16, a database of relevant service providers 160 (e.g., the five doctors shown in FIG. 13) may contain, inter alia, location information, allowing treatment planning module 104 to present or determine, in this example, only relevant surgeons located in Miami-Dade County, Fla. In another embodiment, treatment planning module 104 may determine at least one health service option based on a key word such as "bariatric surgery" and "minimum of five years in practice" for the surgeon as the service provider, as shown in FIG. 16. In FIG. 16, Doctor A 1310, Doctor B 1312, Doctor C 1314, Doctor D 1316, and Doctor E 1318 each meet the minimum preference requirements of five years or more in practice and located in Miami-Dade County, Fla. These five options for service providers may then be selected for in this way, the treatment planning module 104 may filter out database results that include surgeons with less than five years of experience in practice and/or located outside of a specified geographic area, in some cases resulting in zero options being listed for a given therapy. In such a case, where a user 140 is returned no options, other treatment options may be selected and a new search carried out.

Operation 1504 depicts determining at least one health service option for the individual based on the indication of at least one health-related status and based on at least one recognized health care provider. For example, device 102 and/or treatment planning module 104 may determine at least one health service option for the individual based on the indication of at least one health-related status and based on at least one recognized health care provider. In one embodiment, treatment planning module 104 may determine a surgeon as a health service option based on the key phrase "gastric surgery" and certified by the "American Board of Surgery" as the recognized health care provider. Other examples of recognized health care providers include ranked doctors, ranked hospitals, health care providers having an award for quality of care, or the like.

Operation 1506 depicts determining at least one health service option for the individual based on the indication of at least one health-related status and based on at least one health care provider that is compatible with the payment capacity of the individual. For example, device 102 and/or treatment planning module 104 may determine at least one health service option for the individual based on the indication of at least one health-related status and based on at least one health care provider that is compatible with the payment capacity of the individual. In one embodiment, treatment planning module 104 may determine treatment options based on the key phrase "Glioblastoma multiforme" and "Medicaid" as the payment capacity of the individual. In this example, treatment options available for payment with Medicaid may be determined and presented to the user 140. These treatment options will be limited to those approved by the United States Food and Drug Administration, while others, such as Avastin®, may be omitted as incompatible with Medicaid coverage. Conversely, if the payment capacity for the individual is high, off-label treatments and those with experimental status may be included as treatment options. Examples of other payment capacities include specific private insurance plans such as Premera, Blue Cross/Blue Shield, or the like. Other examples include Medicare, fee-for-service, point-of-service, preferred provider organizations, or health maintenance organizations.

Operation 1508 depicts determining at least one health service option for the individual based on the indication of at least one health-related status and based on at least one health care provider that accepts at least one of Medicare, Medicaid, uninsured patients, workers' compensation, or supplemental health insurance. For example, device 102 and/or treatment planning module 104 may determine at least one health service option for the individual based on the indication of at least one health-related status and based on at least one health care provider that accepts at least one of Medicare, Medicaid, uninsured patients, workers' compensation, or supplemental health insurance. In one embodiment, treatment planning module 104 may determine at least one health service option based on an accepted key phrase such as "pregnancy" and "no insurance" as indications of at least one health-related status of an individual. In this example, treatment planning module 104 may determine prenatal care options that are available to an uninsured individual, such as services provided by Denver Health, Denver's public health system, or the Seton System in Central Texas.

Figure 17:
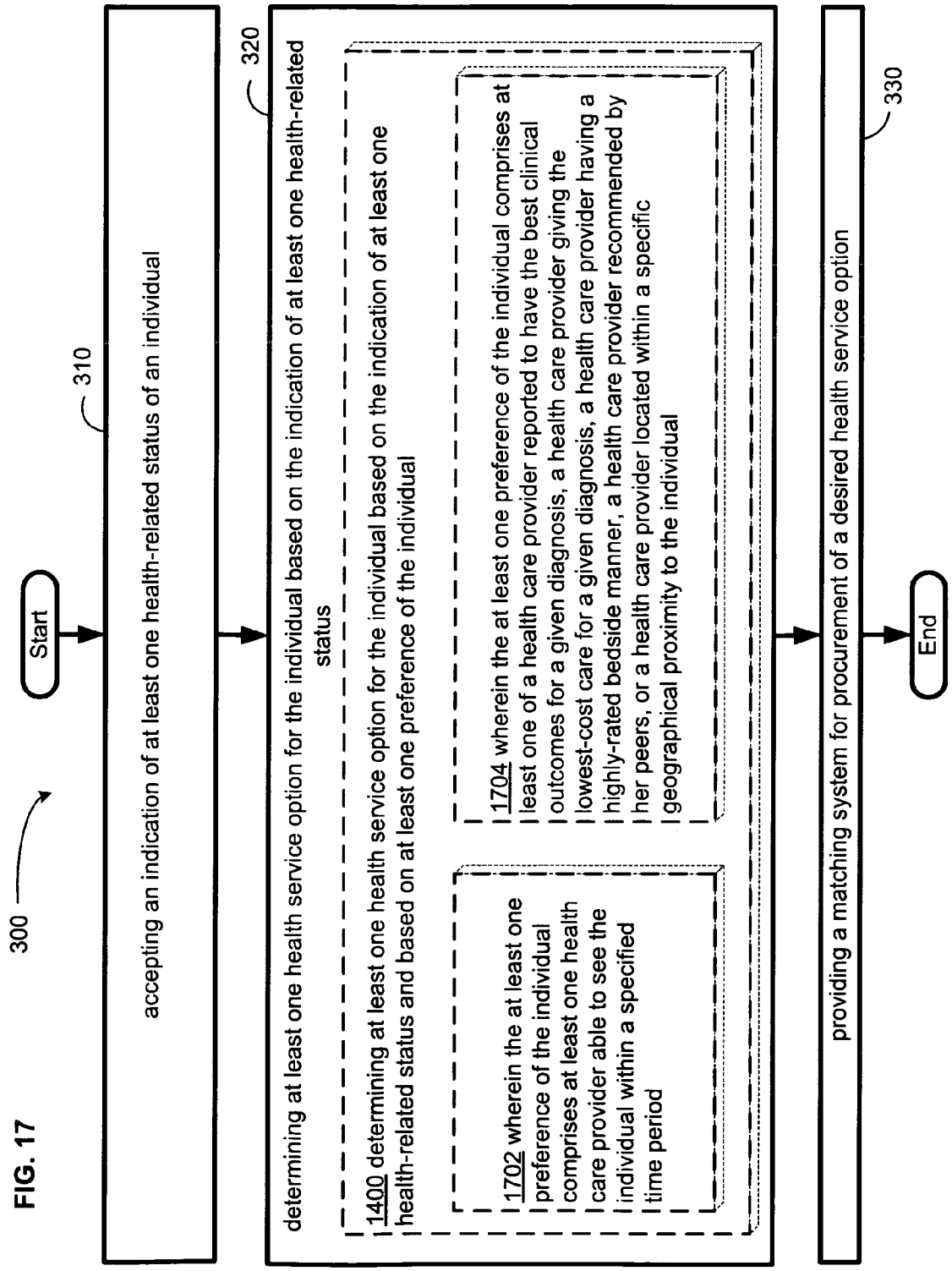
FIG. 17 illustrates an alternative embodiment of the operational flow of FIG. 3.

FIG. 17 illustrates alternative embodiments of the example operational flow 300 of FIG. 3. FIG. 17 illustrates example embodiments where the determining operation 320 may include at least one additional operation. Additional operations may include operation 1702 and/or operation 1704.

Operation 1702 depicts determining at least one health service option for the individual based on the indication of at least one health-related status and based on at least one health care provider able to see the individual within a specified time period. For example, device 102 and/or treatment planning module 104 may determine at least one health service option for the individual based on the indication of at least one health-related status and based on at least one health care provider able to see the individual within a specified time period. In one embodiment, treatment planning module 104 may access information about home care nurses who have immediate availability according to the individual's needs, determining a set of available home care nurses in response to accepting "hospice care" and "immediate availability" as accepted indications of health-related status of an individual.

Operation 1704 depicts determining at least one health service option for the individual based on the indication of at least one health-related status and based on at least one of a health care provider reported to have the best clinical outcomes for a given diagnosis, a health care provider giving the lowest-cost care for a given diagnosis, a health care provider having a highly-rated bedside manner, a health care provider recommended by her peers, or a health care provider located within a specific geographical proximity to the individual. For example, device 102 and/or treatment planning module 104 may determine at least one health service option for the individual based on the indication of at least one health-related status and based on at least one of a health care provider reported to have the best clinical outcomes for a given diagnosis, a health care provider giving the lowest-cost care for a given diagnosis, a health care provider having a highly-rated bedside manner, a health care provider recommended by her peers, or a health care provider located within a specific geographical proximity to the individual. In one embodiment, treatment planning module 104 may accept "type II diabetes" as an indication of health-related status and "top-ranked hospital" as a preference of the individual. Accordingly, treatment planning module 104 may access data relating to hospital rankings for endocrinology, for example the U.S. News and World Report Hospital rankings, which ranks hospitals for the endocrinology specialty. In this example, online rankings show the Mayo Clinic in Rochester, Minn., Mass. General Hospital in Boston, Mass., and Johns Hopkins Hospital in Baltimore, Md. as the top three endocrinology hospitals in the United States.

Figure 18:
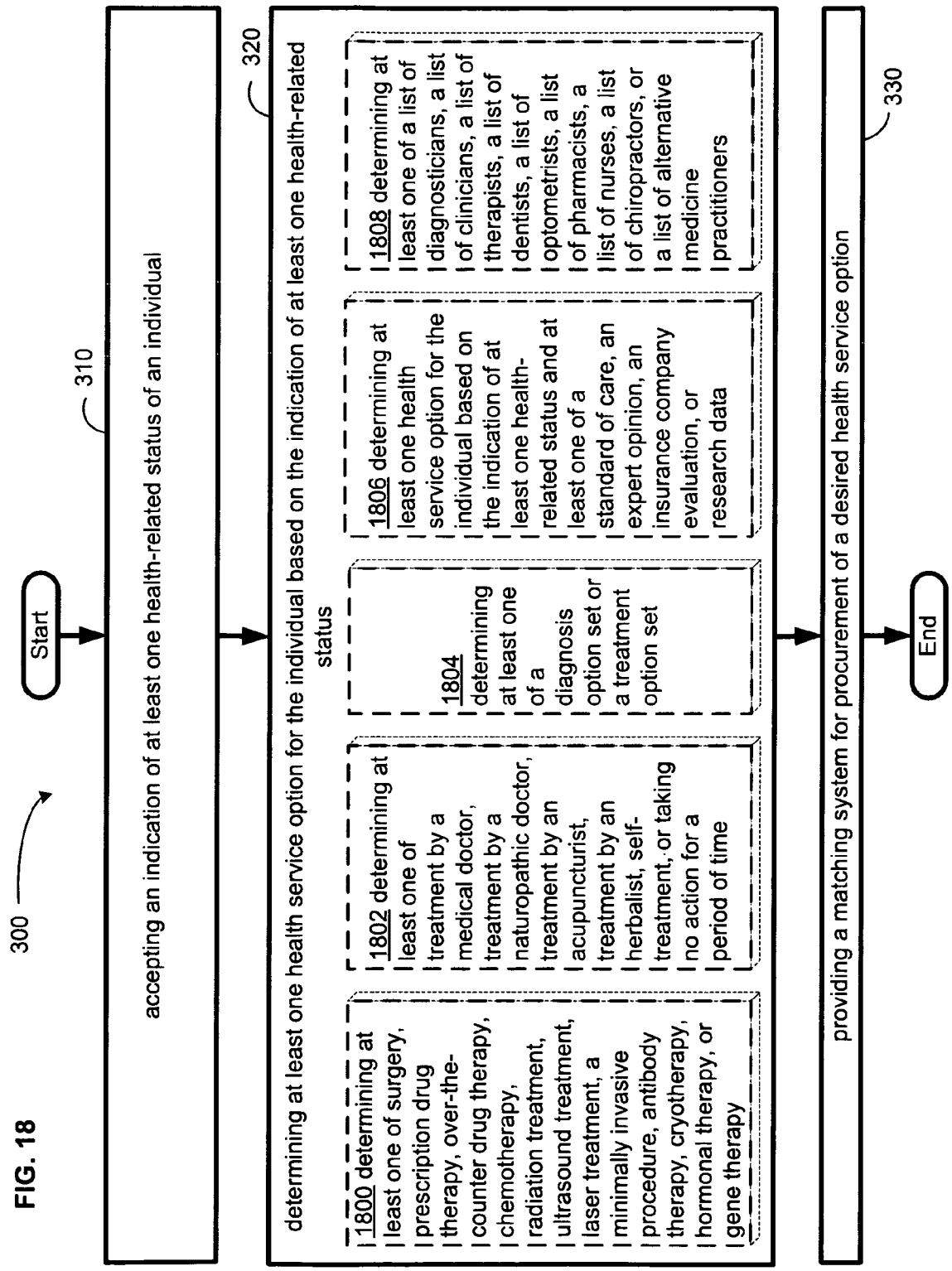
FIG. 18 illustrates an alternative embodiment of the operational flow of FIG. 3.

FIG. 18 illustrates alternative embodiments of the example operational flow 300 of FIG. 3. FIG. 18 illustrates example embodiments where the determining operation 320 may include at least one additional operation. Additional operations may include operation 1800, 1802, 1804, 1806, and/or operation 1808.

Operation 1800 depicts determining at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. For example, device 102 and/or treatment planning module 104 may determine at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. In one embodiment, as shown in FIG. 11, treatment planning module 104, accepting "obesity" as a health-related status 1102, can determine health services options including, for example, Path B including prescription drug therapy, and Path C including surgery.

Operation 1802 depicts determining at least one of treatment by a medical doctor, treatment by a naturopathic doctor, treatment by an acupuncturist, treatment by an herbalist, self-treatment, or taking no action for a period of time. For example, device 102 and/or treatment planning module 104 may determine at least one of treatment by a medical doctor, treatment by a naturopathic doctor, treatment by an acupuncturist, treatment by an herbalist, self-treatment, or taking no action for a period of time. In one embodiment, treatment planning module 104 may accept "obesity" as an indication of health-related status and determine various health service options. As shown in FIG. 11, Path A includes self-treatment in the form of diet and exercise, while Paths B and C include treatment mediated by a physician. Virtually any combination of available testing/treatment options may be presented. Testing/treatment options may be narrowed by user preference.

Operation 1804 depicts determining at least one of a diagnosis option set or a treatment option set. For example, device 102 and/or treatment planning module 104 may determine at least one of a diagnosis option set or a treatment option set. In one embodiment, as shown in FIG. 10, diagnosis or testing options may be determined and presented as initial steps in a decision flow diagram, followed by treatment options. The example of FIG. 10, showing breast cancer testing and treatment options, in some cases may also determine additional testing options post-treatment as follow-up testing options.

Operation 1806 depicts determining at least one health service option for the individual based on the indication of at least one health-related status and at least one of a standard of care, an expert opinion, an insurance company evaluation, or research data. For example, device 102 and/or treatment planning module 104 may determine at least one health service option for the individual based on the indication of at least one health-related status and at least one of a standard of care, an expert opinion, an insurance company evaluation, or research data. In one embodiment, treatment planning module 104 may access standard of care database 210 to determine obesity treatment options that are currently recommended by the medical community and/or approved by one or more insurance companies.

Operation 1808 depicts determining at least one of a list of diagnosticians, a list of clinicians, a list of therapists, a list of dentists, a list of optometrists, a list of pharmacists, a list of nurses, a list of chiropractors, or a list of alternative medicine practitioners. For example, device 102 and/or treatment planning module 104 may determine at least one of a list of diagnosticians, a list of clinicians, a list of therapists, a list of dentists, a list of optometrists, a list of pharmacists, a list of nurses, a list of chiropractors, or a list of alternative medicine practitioners. In one embodiment, treatment planning module 104 can, based on an accepted indication of health-related status for an individual, access service provider database 214 to determine a list of clinicians (e.g., surgeons), as depicted in FIGS. 13 and 16 (i.e., Doctor A 1310 through Doctor E 1318). In another example, treatment planning module 104 can determine a list of optometrists and/or ophthalmologists in response to receiving "blurred vision" as an indication of health-related status. In yet another example, treatment planning module 104 can access service provider database 214 to provide a list of physicians who are pain specialists and a list of acupuncturists in response to receiving "neck pain" as an indication of health-related status.

Figure 19:
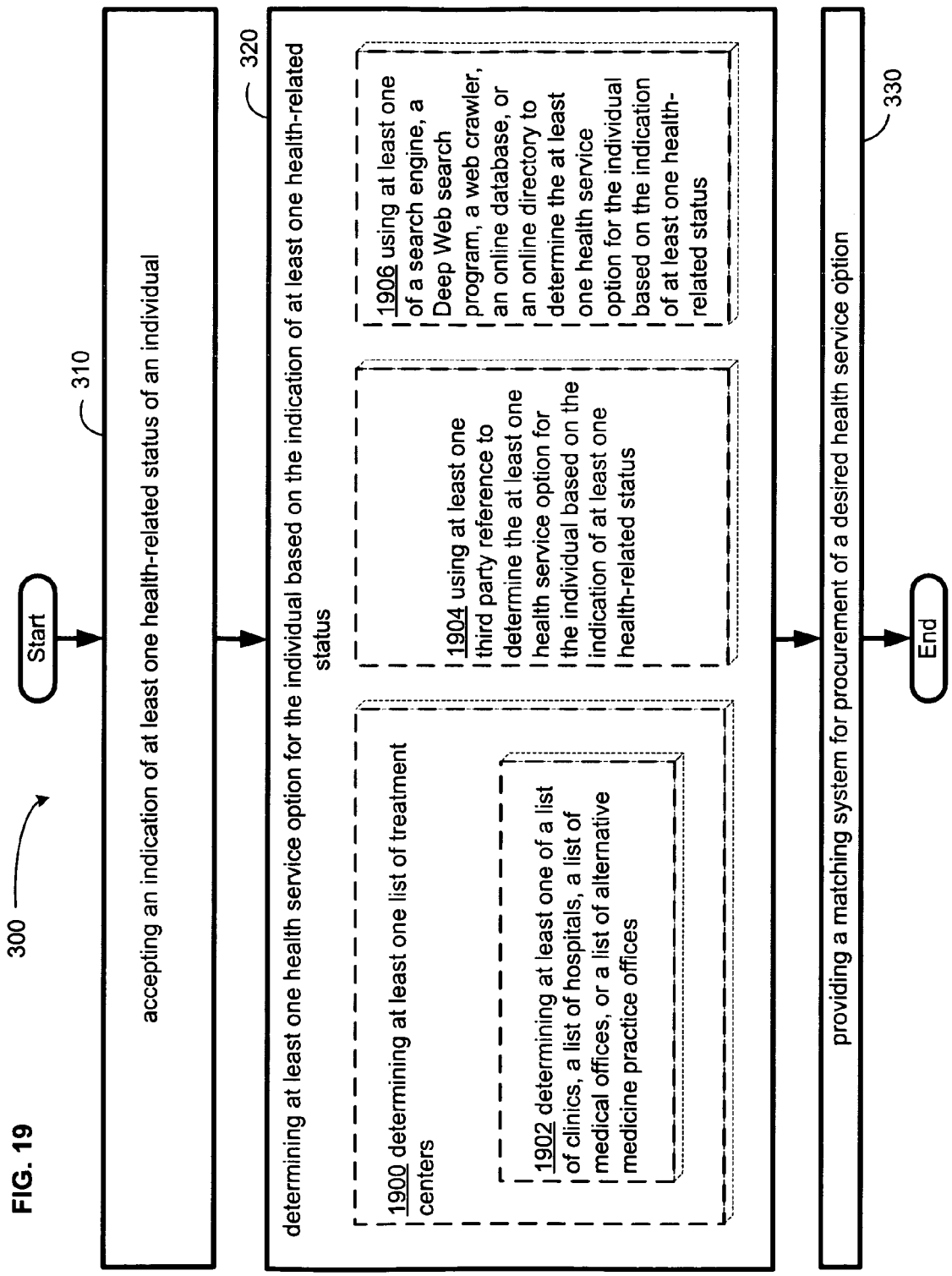
FIG. 19 illustrates an alternative embodiment of the operational flow of FIG. 3.

FIG. 19 illustrates alternative embodiments of the example operational flow 300 of FIG. 3. FIG. 19 illustrates example embodiments in which the determining operation 320 may include at least one additional operation. Additional operations may include operation 1900, 1902, 1904, and/or operation 1906.

Operation 1900 depicts determining at least one list of treatment centers. For example, device 102 and/or treatment planning module 104 may determine at least one list of treatment centers based on an accepted indication of at least one health-related status of an individual. In one embodiment, treatment planning module 104 may determine a list of hospitals that perform a given medical procedure. In another example, treatment planning module 104 may determine a list of recovery centers at which an individual can find services to address "substance abuse" as an indication of at least one health-related status of an individual, for example.

Operation 1902 depicts determining at least one of a list of clinics, a list of hospitals, a list of medical offices, or a list of alternative medicine practice offices. For example, device 102 and/or treatment planning module 104 may determine at least one of a list of clinics, a list of hospitals, a list of medical offices, or a list of alternative medicine practice offices. In one embodiment, treatment planning module 104 may determine a list of diabetes clinics for an individual in need of diabetes health service options. In another example, treatment planning module 104 may determine a list of dental and/or medical offices specializing in oral surgery for an individual with "temporomandibular joint dysfunction" as an indication of at least one health-related status of the individual.

Operation 1904 depicts using at least one third party reference to determine the at least one health service option for the individual based on the indication of at least one health-related status. For example, device 102 and/or treatment planning module 104 may use at least one third party reference to determine the at least one health service option for the individual based on the indication of at least one health-related status. In one embodiment, treatment planning module 104 may use a Physicians' Desk Reference (PDR) database to determine, for example, a set of health-related services options for an individual with "high cholesterol" as an indication of at least one health-related status. In this example, treatment planning module 104 may use a PDR cardiology database to retrieve health-related services options for a patient with high cholesterol.

Operation 1906 depicts using at least one of a search engine, a Deep Web search program, a web crawler, an online database, or an online directory to determine the at least one health service option for the individual based on the indication of at least one health-related status. For example, device 102, treatment planning module 104, and/or Deep Web Search Unit 216 may use at least one of a search engine, a Deep Web search program, a web crawler, an online database, or an online directory to determine the at least one health service option for the individual based on the indication of at least one health-related status. In one embodiment, treatment planning module 104 may use a web crawler to identify a suitable online database, and then a subsequent search function to extract specific data from the online database. For example, if treatment planning module 104 accepts "Crohn's disease" as an indication of at least one health-related status of an individual, it may initiate a search of the web for medical research databases containing Crohn's disease treatment information. A possible result of this search is the medical research database "PubMed." Treatment planning module 104 next may search the PubMed database for "Crohn's disease" in order to determine specific treatment information as the at least one health service option.

In one embodiment, treatment planning module 104 is a system that facilitates searching through content that is accessible though web-based forms. Treatment planning module 104 may accept a query containing keywords, and then analyze the query to create a structured query. Treatment planning module 104 may then perform a lookup based on the structured query in a database containing entries describing the web-based forms. Next, treatment planning module 104 can rank forms returned by the lookup, and use the rankings and associated database entries to facilitate a search through content that is accessible through the forms. Such a federated search system is described in United States patent publication 20060230033, incorporated herein by reference. The federated search paradigm was created and is evolving in response to the vast number of online databases and other web resources that now populate what is known as the deep web, or the invisible Web. With traditional search engines such as Google, only sources that have been indexed by the search engine's crawler technology can be searched, retrieved, and accessed. The large volume of documents that compose the deep Web are not open to traditional Internet search engines because of limitations in crawler technology. Federated searching resolves this issue and makes these deep web documents searchable. Additionally, federated search can provide a singular search interface to numerous underlying deep web data sources. This reduces the burden on the user 140 by not requiring knowledge of each individual search interface or even knowledge of the existence of the individual data sources being searched.

Figure 20:
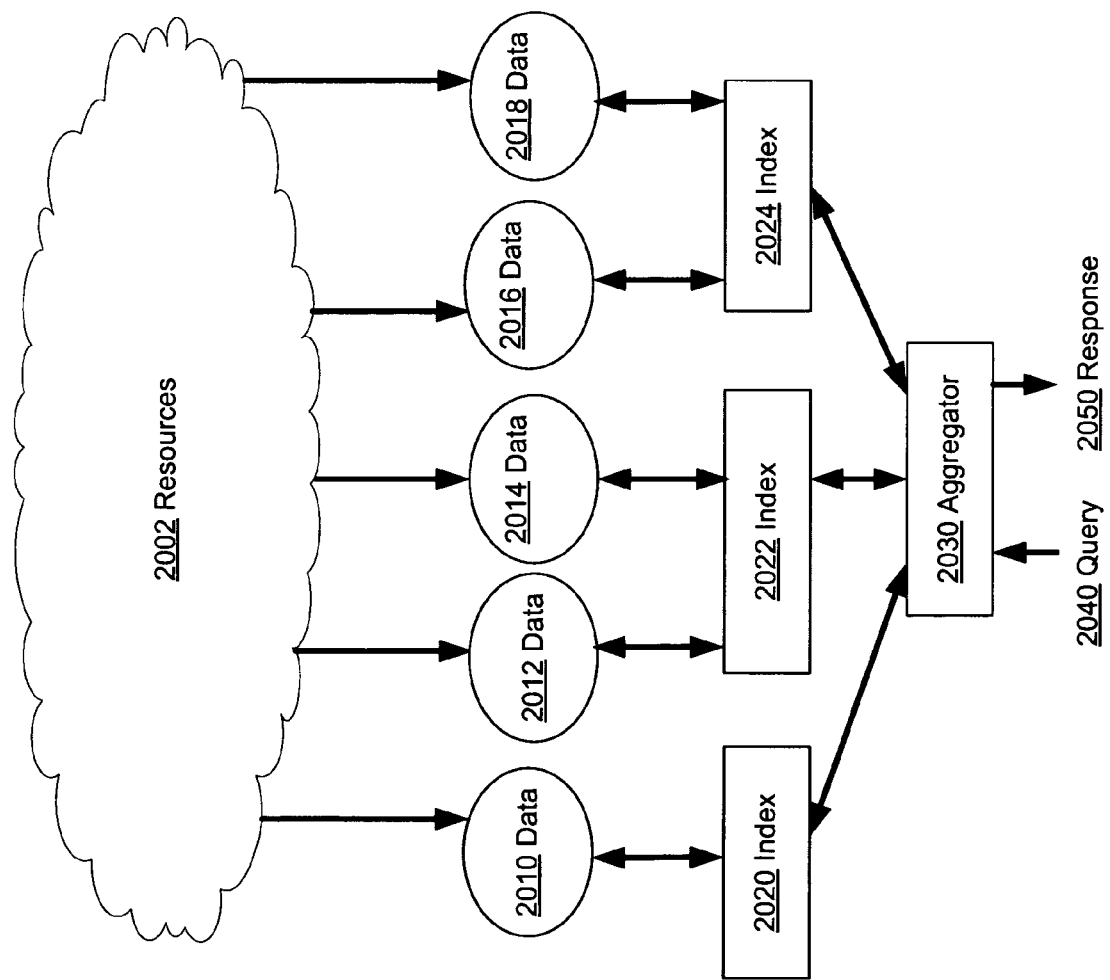
FIG. 20 illustrates an example of a Deep Web search program.

In one embodiment, as shown in FIG. 20, federated searching consists of (1) transforming a query and broadcasting it to a group of disparate databases or other web resources 2002, with the appropriate syntax; (2) merging the results collected from the databases (e.g., data 2010 through data 2018); (3) presenting them in a succinct and unified format with minimal duplication perhaps via index 2020, index 2022, and index 2024, and/or via an aggregator 2030; and (4) providing a means, performed either automatically or by the user 140, to sort the merged result set. Such federated searching may be carried out by, for example, Deep Web search unit 216.

Federated search portals can search public access bibliographic databases, public access Web-based library catalogues (OPACs), Web-based search engines like Google and/or open-access, government-operated or corporate data collections. These individual information sources send back to the portal's interface a list of results from the search query. The user 140 can review this hit list. Some portals will merely screen scrape the actual database results and not directly allow a user 140 to enter the information source's application. More sophisticated ones can de-dupe the results list by merging and removing duplicates. Federated searches can improve the accuracy and relevance of individual searches as well as reduce the amount of time required to search for resources.

They are inherently as current as the individual information sources, because they are searched in real time.

Figure 21:
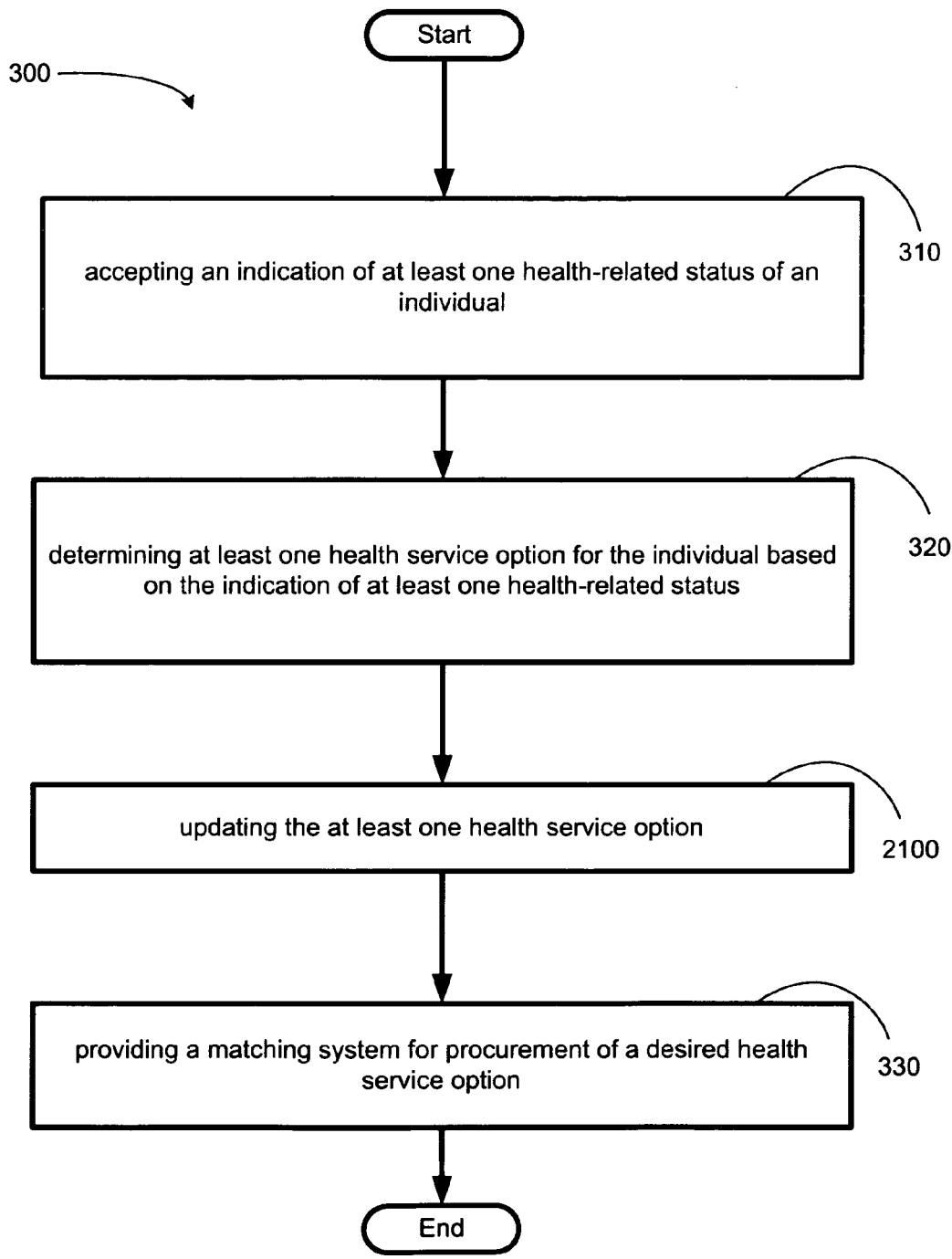
FIG. 21 illustrates an alternative embodiment of the operational flow of FIG. 3.

FIG. 21 illustrates alternative embodiments of the example operational flow 300 of FIG. 3. FIG. 21 illustrates example embodiments in which an updating operation 2100 is included as an additional operation.

Operation 2100 depicts updating the at least one health service option. For example, device 102, treatment planning module 104, and/or Web 2.0 content delivery unit may update the at least one health service option. In one embodiment, treatment planning module 104 may determine an updated health service option after, for example, a period of time has elapsed, so as to keep the health service option up-to-date. For example, where a standard of care is subject to revision by medical authorities, updating a set of health service options is useful in terms of presenting options that reflect the best care possible for an individual. Updating health service options also allows for changes in providers of health services, for example when providers move, change practice areas, or leave a practice area. In one embodiment, Web 2.0 content delivery unit 218 may mediate the updating function.

Figure 22:
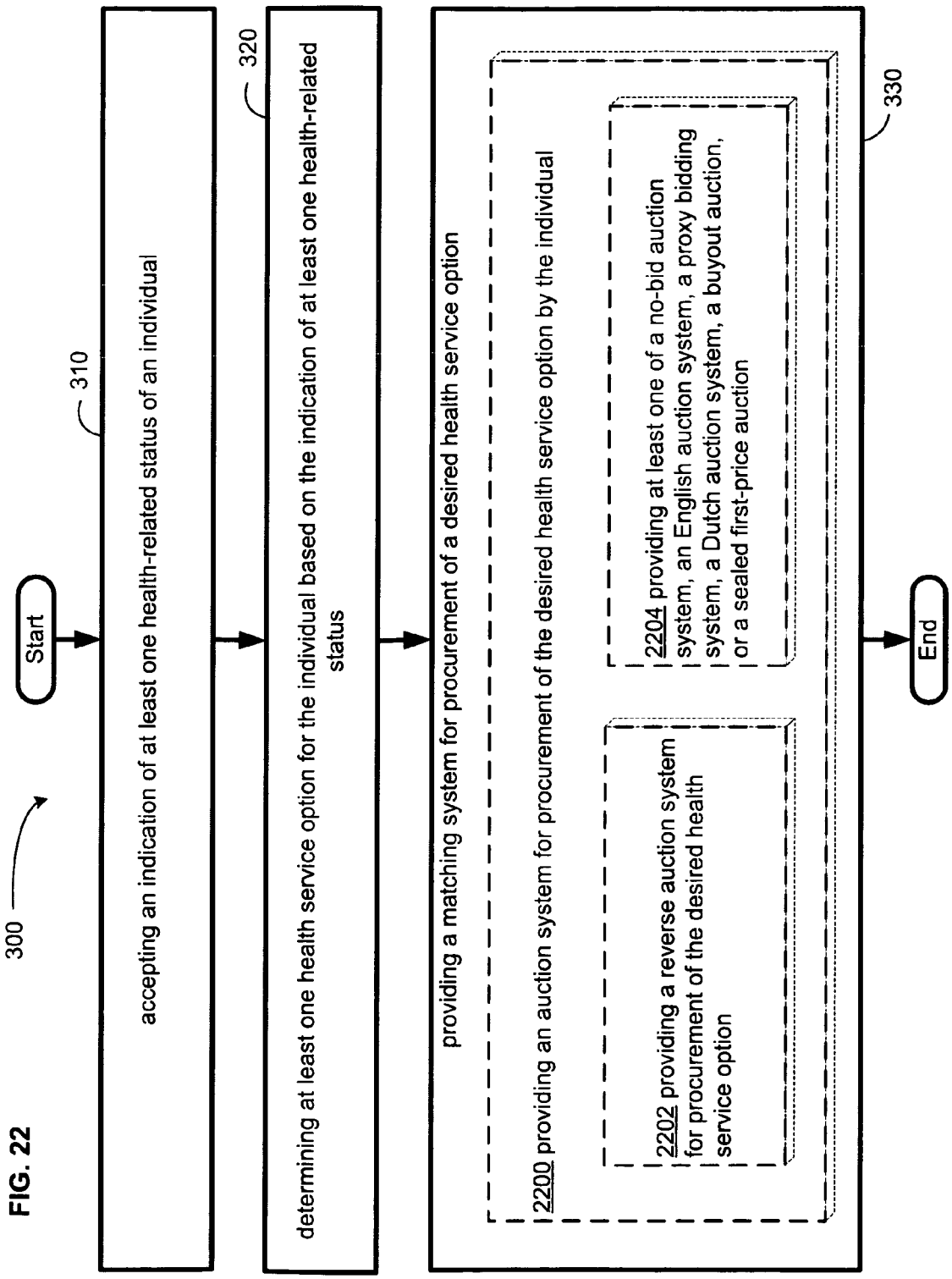
FIG. 22 illustrates an alternative embodiment of the operational flow of FIG. 3.

FIG. 22 illustrates alternative embodiments of the example operational flow 300 of FIG. 3. FIG. 22 illustrates example embodiments in which the providing operation 330 may include at least one additional operation. Additional operations may include operation 2200, 2202, and/or operation 2204.

Operation 2200 depicts providing an auction system for procurement of the desired health service option by the individual. For example, device 102, health care services matching unit 120, and/or auction unit 226 may provide an auction system for procurement of the desired health service option by the individual. In one embodiment, auction unit 226 may match an individual's chosen health-related service with a service provider 160 via a traditional auction. In one example, auction unit 226 may accept a health service option and a zip code, for example "obstetrics" and the 10021 zip code. Auction unit 226 can then access service provider database 222 to generate a list of obstetrics care providers in the 10021 zip code, including physicians 264, hospitals 266, and/or nontraditional service providers such as midwives or birth doulas. Auction unit 226 can then solicit bids from these providers in order to rank them by any of a number of criteria, including cost per unit service, cost per unit time, availability, location, or the like. These criteria may be defined by user 140 and accessed by, for example, auction unit 226 from user preference database 230. Such an auction may run for a defined time period and/or be limited to a defined number of service providers 160.

In one embodiment, appropriate service providers 160 may include those satisfying one or more user preferences, and appropriate service providers may be found, for example, via a federated search carried out by Deep Web search unit 232.

One example of a health care services auction is the model of ZorgVeiling's Care Auction in the Netherlands, which is run through a single web 2.0 application. This is a healthcare purchasing process that uses a dashboard solution for wholesale healthcare purchasers only, including insurance companies. Accordingly, Web 2.0 matching unit 234 may provide an auction system for procurement of the desired health service option by the individual.

An auction may include variations on the basic auction form, including time limits, minimum or maximum limits on bid prices, and special rules for determining the winning bidder(s) and sale price(s). Participants in an auction may or may not know the identities or actions of other participants.

Operation 2202 depicts providing a reverse auction system for procurement of the desired health service option. For example, device 102, health care services matching unit 120, and/or auction unit 226 may provide a reverse auction system for procurement of the desired health service option. In one embodiment, auction unit 226 may match take bids from service providers 160 to drive down the cost of the health service option. A reverse auction, also called a procurement auction, e-auction, sourcing event, e-sourcing, or eRA, is a tool commonly used in industrial business-to-business procurement. It is a type of auction in which the role of the buyer and seller are reversed, with the primary objective to drive purchase prices downward. In an ordinary auction (also known as a forward auction), buyers compete to obtain a good or service. In a reverse auction, sellers compete to obtain business.

In one embodiment of a reverse auction, a user 140 may contract with a market maker to help make the necessary preparations to conduct the reverse auction. This may include finding service providers 160, training new and incumbent service providers 160, organizing the auction, managing the auction event, and providing auction data to user 140 to facilitate decision making. In one embodiment, a market maker, on behalf of the user 140, issues a request for quotation (RFQ) to purchase a particular health service option or group of options (called a "lot"). At the designated day and time, several service providers 160 log on to the auction site and input several quotes over a 30-90 minute period. These quotes reflect the prices at which they are willing to supply the requested health service option.

In one embodiment, quoting performed in real-time via the Internet results in dynamic bidding. This helps achieve rapid downward price pressure that is not normally attainable using traditional static 3-quote paper-based bidding processes. The prices that a user 140 may obtain in the reverse auction reflect the market which is created at the moment in time when the auction is held. The user 140 may award a contract to the service provider 160 who bid the lowest price. Or, a user 140 could award a contract to a service provider 160 who bid higher prices depending upon the preferences of user 140, e.g., specific needs with regards to quality, lead-time, capacity, or other value-adding capabilities.

The use of optimization software has become popular to help users 140 determine which service provider 160 to choose. Such optimization software may include relevant user 140 and service provider 160 business data, including preferences and/or constraints.

Operation 2204 depicts providing at least one of a no-bid auction system, an English auction system, a proxy bidding system, a Dutch auction system, a buyout auction, or a sealed first-price auction. For example, device 102, health care services matching unit 120, and/or auction unit 226 may provide at least one of a no-bid auction system, an English auction system, a proxy bidding system, a Dutch auction system, a buyout auction, or a sealed first-price auction. In one embodiment, auction unit 226 may provide a proxy bidding system wherein service providers 160 may submit bids to an insurance company as proxy holder bidders in a reverse auction for a health service option. In one embodiment, a service provider 160 may tell an auctioneer the absolute minimum fee for a service that they are willing to accept from a user 140, as a bid for providing a desired health service option. An auctioneer such as a dedicated web site or an insurance company may then place a bid on behalf of the service provider 160. The auctioneer or insurance company then continues to bid on behalf of the service provider 160, whenever he or she is outbid by another service provider's bid, until the minimum is exceeded or the auction is won.

A no-bid auction system is one in which a service provider 160 lists a price for a given health service option subject to election or not by a user 140, for example. One example of a no-bid auction is the "buy-it-now" feature of eBay, in which an item may be purchased for an advertised price as an alternative to a traditional auction with competing bids. In one embodiment, a no-bid auction may be mediated by sole source selection unit 224. Sole source selection unit 224 can find a single best service provider 160 for an interested user 160 based on an accepted indication of at least one health-related status and/or user preference data, for example from user preference database 230.

In one embodiment of an English auction, also known as an open ascending price auction, users 140 may bid openly against one another, with each subsequent bid higher than the previous bid. An auctioneer may announce prices, bidders may call out their bids themselves (or have a proxy call out a bid on their behalf), or bids may be submitted electronically with the highest current bid publicly displayed. In some cases a maximum bid might be left with the auctioneer, who may bid on behalf of the bidder according to the bidder's instructions. The auction ends when no participant is willing to bid further, at which point the highest bidder pays their bid. Alternatively, if a service provider 160 has set a minimum sale price in advance (the reserve price) and the final bid does not reach that price then the contract for a desired health service option remains unsold. In some embodiments, the auctioneer may set a minimum amount by which the next bid must exceed the current highest bid. The most significant distinguishing factor of this auction type is that the current highest bid is always available to potential bidders. At least two bidders are required.

Proxy bidding is an implementation of an English second-price auction, in which the winning bidder pays the price of the second-highest bid plus a defined increment. It differs from a Vickrey auction in that bids are not sealed; the "current highest bid" (defined as second-highest bid plus bid increment) is always displayed. In a standard first-price English auction the winner pays the amount of their bid, regardless of competitors' bids, and it is therefore desirable to place a bid that exceeds the current highest bid by the smallest possible increment. Under proxy bidding, however, the price paid is determined only by competitors' bids and not by the amount of the new bid, and so there is no economically rational incentive to place a bid below the amount one is willing to pay, or to place multiple increasing bids. An economically rational bidder will therefore bid the maximum amount they are willing to pay on their first bid, and never raise their bid.

In a Dutch auction, also known as an open descending price auction, the auctioneer begins with a high asking price which is lowered until some participant is willing to accept the auctioneer's price. The winning participant pays the last announced price. The term "Dutch auction" is also sometimes used to describe online auctions where several identical goods are sold simultaneously to an equal number of high bidders.

A buyout auction is an auction with a set price ("buyout price") that any bidder can accept at any time during the auction, thereby immediately ending the auction and winning the service contract. If no bidder elects the buyout option before the end of bidding the highest bidder wins and pays their bid. Buyout options can be either temporary or permanent. In a temporary buyout auction the option to buy out the auction is no longer available after the first bid is placed. In a permanent buyout auction the buyout option remains available throughout the entire auction until the close of bidding. The buyout price can either remain the same throughout the entire auction, or vary throughout according to preset rules or at the discretion of, for example, service provider 160.

In a sealed first-price auction, also known as a first-price sealed-bid auction, all bidders simultaneously submit sealed bids so that no bidder knows the bid of any other participant. The highest bidder pays the price they submitted. This type of auction is distinct from the English auction, in that bidders can only submit one bid each. Furthermore, as bidders cannot see the bids of other participants they cannot adjust their own bids accordingly.

Figure 23:
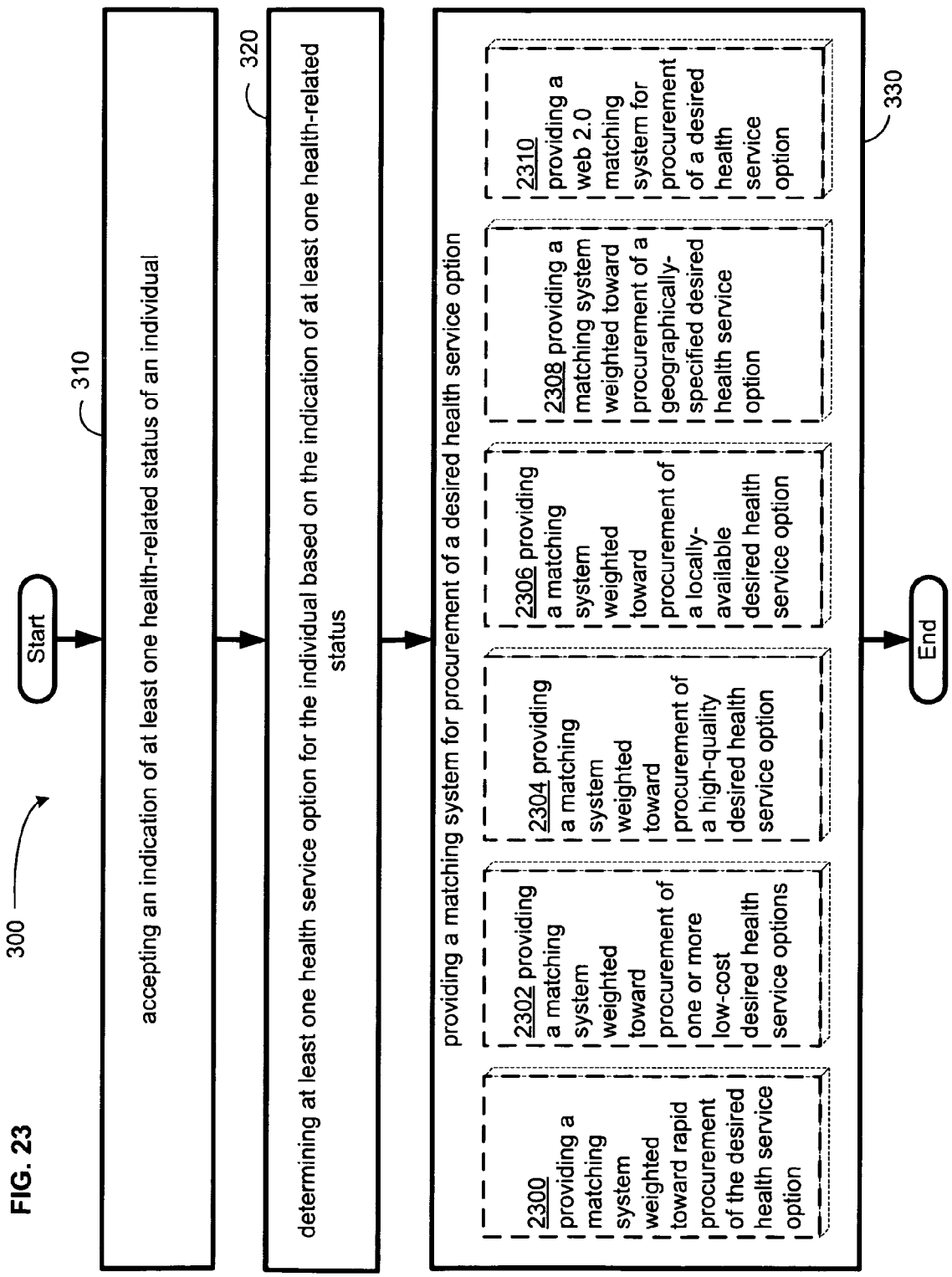
FIG. 23 illustrates an alternative embodiment of the operational flow of FIG. 3.

FIG. 23 illustrates alternative embodiments of the example operational flow 300 of FIG. 3. FIG. 23 illustrates example embodiments in which the providing operation 330 may include at least one additional operation. Additional operations may include operation 2300, 2302, 2304, 2306, 2308, and/or operation 2310.

Operation 2300 depicts providing a matching system weighted toward rapid procurement of the desired health service option. For example, device 102, health care services matching unit 120, and/or auction unit 226 may provide a matching system weighted toward rapid procurement of the desired health service option. In one embodiment, health care services matching unit 120 may accept "canaloplasty" and "cataract surgery" as at least one indication of a health-related status. User preference data 212 may also be accepted such as "immediate availability" and "Johnstown, Pa.". Health care services matching unit 120 may then determine a list of eye surgeons capable of addressing glaucoma and cataract issues for the individual/user 140. In this example, an auction unit 226 weighted toward rapid procurement of the desired health service option may provide an internet auction among determined physicians 264 such that the auction is scheduled to end within, for example, three business days instead of a standard five business days or seven days, for example. In an alternative example, health care services matching unit 120 and/or sole source selection unit 224 may expedite procurement of a desired health service option by providing a no-bid auction or by providing a single best match for an available service provider 160.

Operation 2302 depicts providing a matching system weighted toward procurement of one or more low-cost desired health service options. For example, device 102, health care services matching unit 120, auction unit 226, and/or arbitrage unit 228 may provide a matching system weighted toward procurement of one or more low-cost desired health service options. In one embodiment, arbitrage unit 228 may take advantage of a price differential between two or more markets, striking a combination of matching deals that capitalize upon the imbalance, the profit and/or savings being the difference between the market prices. For example, arbitrage unit 228 may accept bids from, for example, hospitals 266 and health maintenance organizations 268 in various geographic areas or markets, compare the bids, and select a match on the basis of the best cost differential and/or lowest cost for the user 140/individual. In one embodiment, arbitrage unit 228 may take into account travel distance in selecting a low-cost health care services provider 162. For example, while health care costs may vary between large and small markets, a resident of a large market may not want to choose a low-cost health care services provider 162 in a small market for reasons of quality and/or convenience. Therefore, whereas arbitrage unit 228 may identify a spread between bid prices for identical services in each market, arbitrage unit 228 may factor in such factors as distance, number of procedures performed historically, staff expertise, user preference data from user preference database 230, or the like in providing a matching system for procurement of a desired health service option. It should be understood that performing the actual matching function for a user 140/individual is one way of providing a matching system for procurement of a desired health service option.

Operation 2304 depicts providing a matching system weighted toward procurement of a high-quality desired health service option. For example, device 102, health care services matching unit 120, sole source selection unit 224, auction unit 226, and/or arbitrage unit 228 may provide a matching system weighted toward procurement of a high-quality desired health service option. In one embodiment, sole source selection unit 224 may, based on a determined at least one health service option for the individual based on the indication of at least one health-related status, match user 140 with the highest-quality health service option available. For example, where treatment planning module has determined neurosurgery as a health service option for glioblastoma multiforme, sole source selection unit 224 may match the top-ranked Mayo Clinic in Rochester, Minn. with an individual's personal assistant as the user 140.

Operation 2306 depicts providing a matching system weighted toward procurement of a locally-available desired health service option. For example, device 102, health care services matching unit 120, sole source selection unit 224, auction unit 226, and/or arbitrage unit 228 may provide a matching system weighted toward procurement of a locally-available desired health service option. In one embodiment, auction unit 226 may initiate a reverse auction in which health care service providers 162 bid on a given desired health services option. In this example, auction unit 226 may filter a list of physicians, for example, as determined by treatment planning module 104 to include only those within a local area. Alternatively, auction unit 226 may favor bids from local service providers 160 during an auction to match user 140 with a service provider 160, perhaps based on a preference from user preference database 230.

Operation 2308 depicts providing a matching system weighted toward procurement of a geographically-specified desired health service option. For example, device 102, health care services matching unit 120, sole source selection unit 224, auction unit 226, and/or arbitrage unit 228 may provide a matching system weighted toward procurement of a geographically-specified desired health service option. In one embodiment, auction unit 226 may initiate a reverse auction in which health care service providers 162 in a foreign country bid on a given desired health services option. In this example, auction unit 226 may filter a list of service providers 162, for example, as determined by treatment planning module 104 to include only those within a certain geographic area, for example, "India." Accordingly this system can be used to match a user 140 and/or individual in one country with a service provider 160 in another country or region. One example of this kind of specific geographic matching is health care tourism, also known as medical travel, health tourism, or global healthcare, in which an individual in need of health care travels to a foreign country for a lower cost service, a stimulating travel experience, and/or specialist health care, or the like. Alternatively, auction unit 226 may favor bids from service providers 160 in a specified geographic region during an auction to match user 140 with a service provider 160, perhaps based on a preference from user preference database 230.

Operation 2310 depicts providing a web 2.0 matching system for procurement of a desired health service option. For example, device 102, health care services matching unit 120, sole source selection unit 224, auction unit 226, and/or arbitrage unit 228 may provide a web 2.0 matching system for procurement of a desired health service option. In one embodiment, auction unit 226 may conduct an internet auction to match a user 140 with a service provider 160 to provide a desired health services option, such as open heart surgery. In this example, auction progress may be monitored by an auctioneer and/or user 140 by way of a web 2.0 application, such as that used by the ZorgVeiling Care Auction system discussed above. This system manages results with IBM's Dashboard Solutions for WebSphere Portal, in which interactive portlets allow for filtering of data, and big-picture monitoring of bidding progress and results. Such web 2.0 systems provide security in terms of SSL certificates, database encryption, HTTP redirect functionality, firewalls, secure cybercenters, and the like. These systems can also be implemented using readily available hardware from a single supplier, e.g., Microsoft and IBM. Microsoft products provide SQL Server-oriented client environments complete with OLAP viewing, dashboarding, and dynamic data visualization capabilities. Common features of a web 2.0 application include service-oriented architecture and integration with web services, including Web APIs that can be accessed over a network, such as the Internet, and executed on a remote system hosting the requested services.

Figure 24:
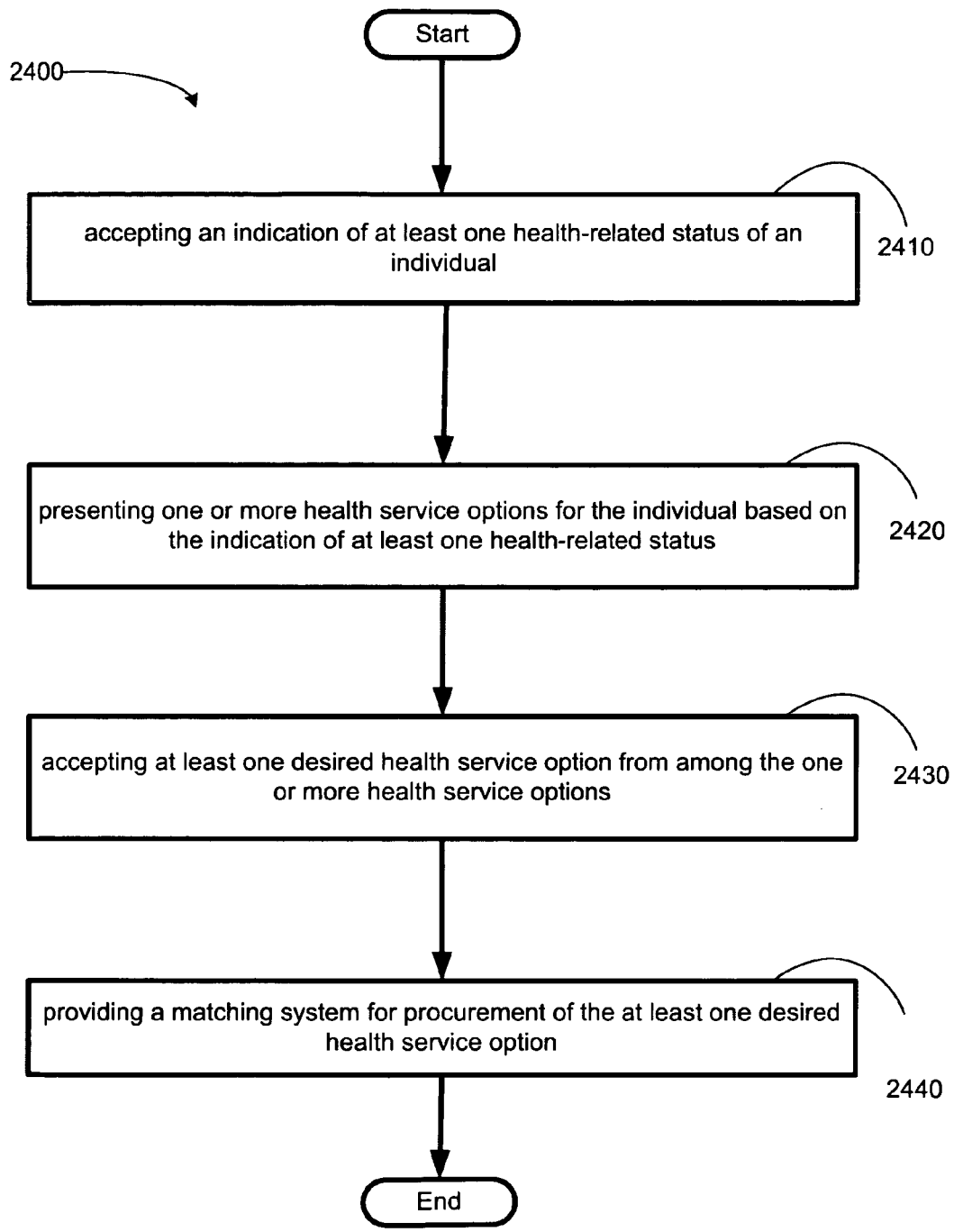
FIG. 24 illustrates an example of an operational flow representing example operations related to health services planning and matching, which may serve as a context for introducing one or more processes and/or devices described herein.

FIG. 24 illustrates an operational flow 2400 representing example operations related to health services planning and matching. In FIG. 24 discussion and explanation may be provided with respect to the above-described system environments of FIGS. 1-2, and/or with respect to other examples and contexts. However, it should be understood that the operational flow may be executed in a number of other environments and contexts including that of FIG. 20, and/or in modified versions of FIGS. 1-2. Also, although the various operational flows are presented in the sequence(s) illustrated, it should be understood that the various operations may be performed in other orders than those which are illustrated, or may be performed concurrently.

After a start operation, operation 2410 depicts accepting an indication of at least one health-related status of an individual. For example, device 102 and/or treatment planning module 104 may accept an indication of at least one health-related status of an individual. In one embodiment, treatment planning module 104 may accept from user 140 "glaucoma treatment" as an indication of at least one health-related status of an individual. Other kinds of health-related status indications may be accepted as discussed above, including a query for testing, a query for achievement of a personal goal, and the like.

Operation 2420 depicts presenting one or more health service options for the individual based on the indication of at least one health-related status. For example, device 102 and/or treatment planning module 104 may present one or more health service options for the individual based on the indication of at least one health-related status. As discussed above, in one embodiment, treatment planning module may access, for example, research data, standard of care data, historical experience data, user preference data, and/or service provider data in determining for presentation one or more health service options for the individual based on the indication of at least one health-related status. For example, accepting "glaucoma treatment" may initiate a search of an experience database 208, including for example, the Dallas Glaucoma Patient Database created by the Southwestern Medical Center, which follows all glaucoma patients treated at University of Texas Southwestern, in order to establish long-term trends and collect demographic data about people with glaucoma. In this example, a search of the Dallas Glaucoma Patient Database by treatment planning module 104 may result in the presentation of several experimental therapies, among other standard and/or approved therapies. Treatment planning module 104 may also present a list of qualified service providers 160, such as hospitals specializing in glaucoma treatment, insurers that cover various glaucoma treatments, and/or government agencies such as Medicare that pay for various glaucoma treatments.

Operation 2430 depicts accepting at least one desired health service option from among the one or more health service options. For example, device 102 and/or health care services matching unit 120 may accept at least one desired health service option from among the one or more health service options. In one embodiment, health care services matching unit 120 may accept from user 140 a selected glaucoma treatment option such as "trabeculectomy" from among a set of presented glaucoma treatments. User 140 may also provide user preference data 212 such as a geographical location and/or a physician preference, such as "in practice for 10-15 years."

Operation 2440 depicts providing a matching system for procurement of the at least one desired health service option. For example, device 102, health care services matching unit 120, sole source selection unit 224, auction unit 226, and/or arbitrage unit 228 may provide a matching system for procurement of the at least one desired health service option. In one embodiment, auction unit 226 can initiate a reverse auction among local eye surgeons having 10-15 years of practice experience. Such an auction may match user 140 with an eye surgeon able to perform a trabeculectomy for user 140 at a competitive price relative to other eye surgeons having similar experience in the specified geographic area.

FIG. 25 illustrates a partial view of an example article of manufacture 2500 that includes a computer program 2504 for executing a computer process on a computing device. An embodiment of the example article of manufacture 2500 is provided using a signal bearing medium 2502, and may include one or more instructions for accepting an indication of at least one health-related status of an individual; determining at least one health service option for the individual based on the indication of at least one health-related status; and providing a matching system for procurement of a desired health service option. The one or more instructions may be, for example, computer executable and/or logic-implemented instructions. In one implementation, the signal-bearing medium 2502 may include a computer-readable medium 2506. In one implementation, the signal bearing medium 2502 may include a recordable medium 2508. In one implementation, the signal bearing medium 2502 may include a communications medium 2510.

FIG. 26 illustrates an example system 2600 in which embodiments may be implemented. The system 2600 includes a computing system environment. The system 2600 also illustrates a user 140 using a device 2604, which is optionally shown as being in communication with a computing device 2602 by way of an optional coupling 2606. The optional coupling 2606 may represent a local, wide-area, or peer-to-peer network, or may represent a bus that is internal to a computing device (e.g., in example embodiments in which the computing device 2602 is contained in whole or in part within the device 2604). A storage medium 2608 may be any computer storage media. In one embodiment, the computing device 2602 may include a virtual machine operating within another computing device. In an alternative embodiment, the computing device 2602 may include a virtual machine operating within a program running on a remote server.

The computing device 2602 includes computer-executable instructions 2610 that when executed on the computing device 2602 cause the computing device 2602 to (a) accept an indication of at least one health-related status of an individual; (b) determine at least one health service option for the individual based on the indication of at least one health-related status; and (c) provide a matching system for procurement of a desired health service option. As referenced above and as shown in FIG. 26, in some examples, the computing device 2602 may optionally be contained in whole or in part within the device 2604.

In FIG. 26, then, the system 2600 includes at least one computing device (e.g., 2602 and/or 2604). The computer-executable instructions 2610 may be executed on one or more of the at least one computing device. For example, the computing device 2602 may implement the computer-executable instructions 2610 and output a result to (and/or receive data from) the computing device 2604. Since the computing device 2602 may be wholly or partially contained within the computing device 2604, the device 2604 also may be said to execute some or all of the computer-executable instructions 2610, in order to be caused to perform or implement, for example, various ones of the techniques described herein, or other techniques.

The device 2604 may include, for example, a portable computing device, workstation, or desktop computing device. In another example embodiment, the computing device 2602 is operable to communicate with the device 2604 associated with the user 140 to receive information about the input from the user 140 for performing data access and data processing, and provide a matching system for procurement of a desired health service option.

Although user 140 is shown/described herein as a single illustrated figure, those skilled in the art will appreciate that user 140 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

Figure 27:
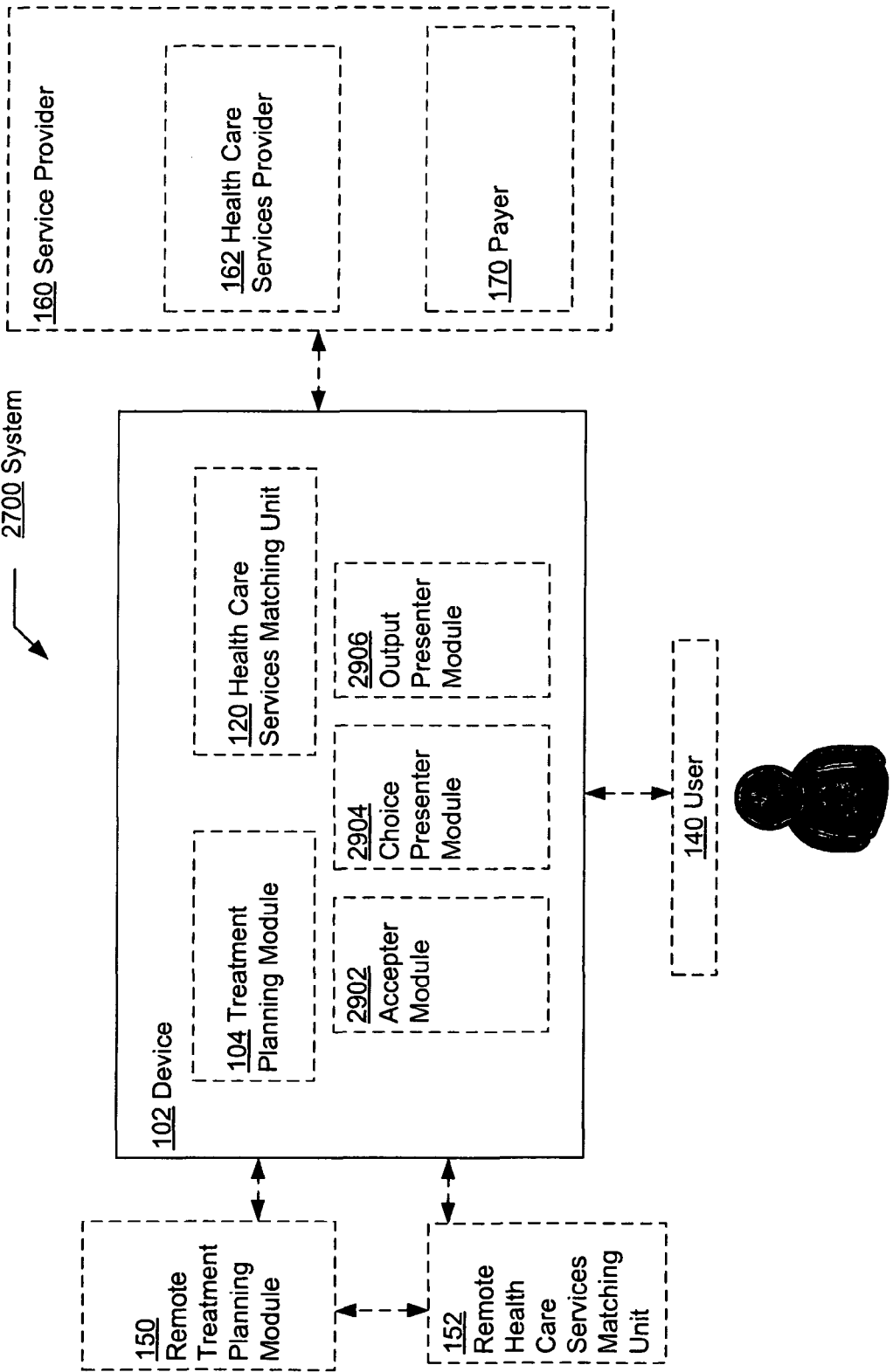
FIG. 27 illustrates an example of a health services planning and matching system in which embodiments may be implemented, perhaps in a device and/or through a network, which may serve as a context for introducing one or more processes and/or devices described herein.

FIG. 27 illustrates an example system 100 in which embodiments may be implemented. The system 100 includes a device 102. The device 102 may contain, for example, treatment planning module 104, health care services matching unit 120, accepter module 2902, choice presenter module 2904, and/or output presenter module 2906. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept user input to provide one or more health services options, for example via treatment planning module 104. Device 102 may accept a selected health service option and match it with an appropriate service provider via, for example health care services matching unit 120. Service provider 160 may include, for example, health care services provider 162 and/or payer 170.

In FIG. 27, health care services matching unit 120 may solicit a health care services option from a service provider 160. Such a solicitation may include an invitation to bid in an auction, a reverse auction, or the like. Results of such a solicitation may include matching a doctor capable of providing a chosen health care services option with the user 140 in need of the chosen health care services option, perhaps according to one or more preferences provided by the user 140.

In FIG. 27, the device 102 is illustrated as possibly being included within a system 2700. Of course, virtually any kind of computing device may be used to implement the special purpose treatment planning module 104, special purpose health care services matching unit 120, special purpose accepter module 2902, special purpose choice presenter module 2904, and/or special purpose output presenter module 2906, such as, for example, a workstation, a desktop computer, a networked computer, a server, a collection of servers and/or databases, a virtual machine running inside a computing device, a mobile computing device, or a tablet PC.

Additionally, not all of the treatment planning module 104, health care services matching unit 120, accepter module 2902, choice presenter module 2904, and/or output presenter module 2906 need be implemented on a single computing device. For example, the treatment planning module 104, health care services matching unit 120, accepter module 2902, choice presenter module 2904, and/or output presenter module 2906 may be implemented and/or operable on a remote computer, while a user interface and/or local instance of the treatment planning module 104, health care services matching unit 120, accepter module 2902, choice presenter module 2904, and/or output presenter module 2906 are implemented and/or occur on a local computer. Further, aspects of the treatment planning module 104, health care services matching unit 120, accepter module 2902, choice presenter module 2904, and/or output presenter module 2906 may be implemented in different combinations and implementations than that shown in FIG. 27. For example, functionality of a user interface may be incorporated into the treatment planning module 104, health care services matching unit 120, accepter module 2902, choice presenter module 2904, and/or output presenter module 2906. The treatment planning module 104, health care services matching unit 120, accepter module 2902, choice presenter module 2904, and/or output presenter module 2906 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, the treatment planning module 104, health care services matching unit 120, accepter module 2902, choice presenter module 2904, and/or output presenter module 2906 may process user input data according to health care options and/or service provider information available as updates through a network.

Treatment planning module 104, health care services matching unit 120, accepter module 2902, choice presenter module 2904, and/or output presenter module 2906 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 28:
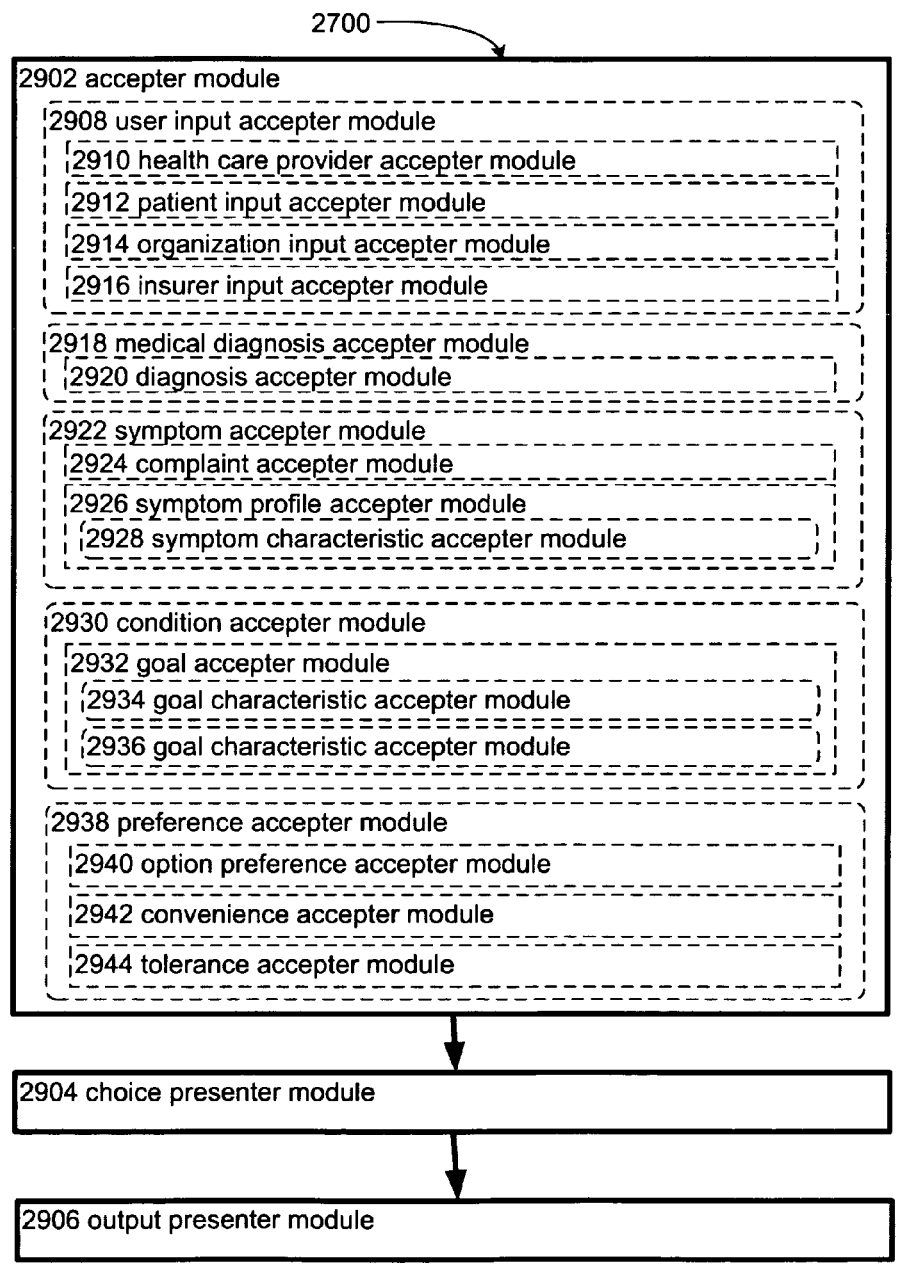
FIG. 28 illustrates certain alternative embodiments of the health services planning and matching system of FIG. 1.

FIG. 28 further illustrates system 2700 including accepter module 2902, choice presenter module 2904, and/or output presenter module 2906. Accepter module 2902 may include user input accepter module 2908, medical diagnosis accepter module 2918, symptom accepter module 2922, condition accepter module 2930, and/or preference accepter module 2938. User input accepter module 2908 may include health care provider accepter module 2910, patient input accepter module 2912, organization input accepter module 2914, and/or insurer input accepter module 2916. Medical diagnosis accepter module 2918 may include diagnosis accepter module 2920. Symptom accepter module 2922 may include complaint accepter module 2924 and/or symptom profile accepter module 2926. Symptom profile accepter module 2926 may include symptom characteristic accepter module 2928. Condition accepter module 2930 may include goal accepter module 2932. Goal accepter module 2932 may include goal characteristic accepter module 2934 and/or goal characteristic accepter module 2936. Preference accepter module 2938 may include option preference accepter module 2940, convenience accepter module 2942, and/or tolerance accepter module 2944.

Figure 29:
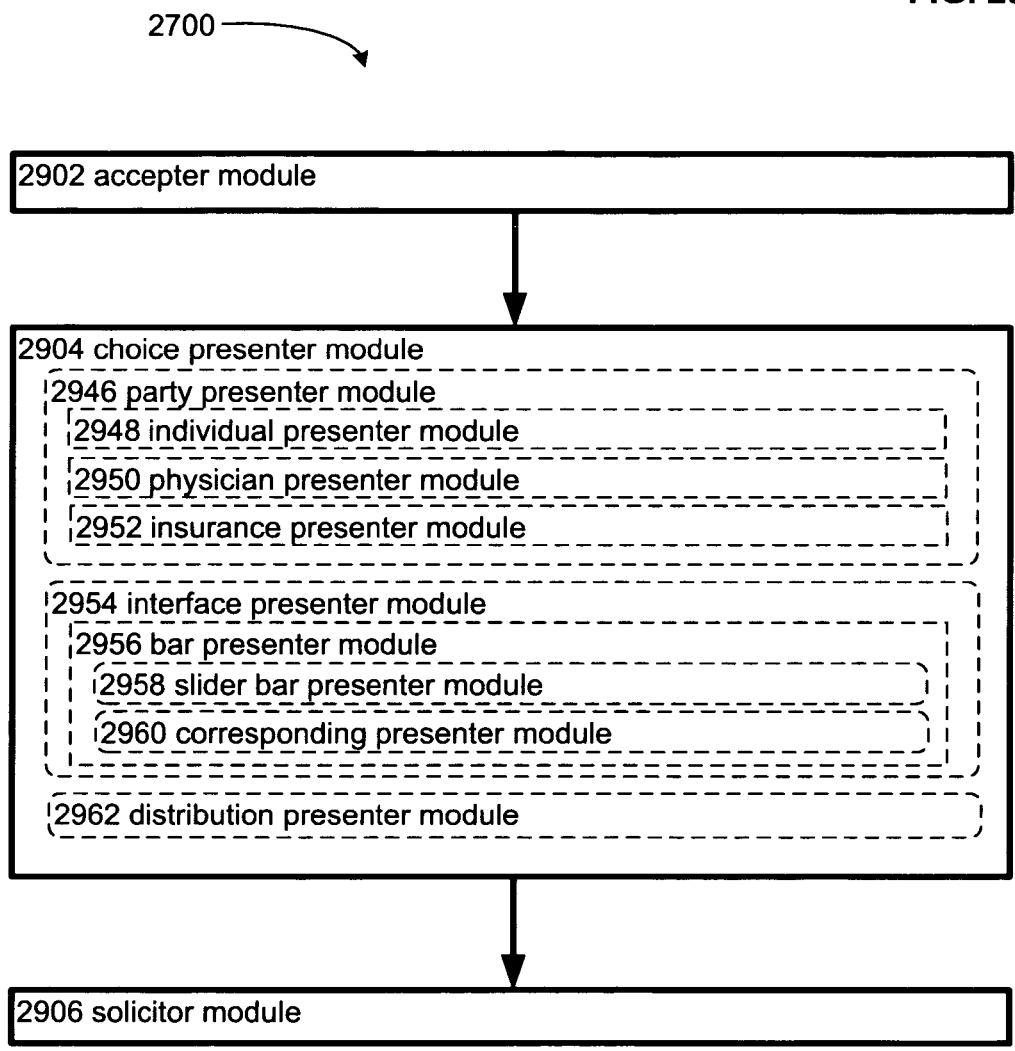
FIG. 29 illustrates certain alternative embodiments of the health services planning and matching system of FIG. 1.

FIG. 29 further illustrates system 2700 including accepter module 2902, choice presenter module 2904, and/or output presenter module 2906. Choice presenter module 2904 may include party presenter module 2946, interface presenter module 2954, and/or distribution presenter module 2962. Party presenter module 2946 may include individual presenter module 2948, physician presenter module 2950, and/or insurance presenter module 2952. Interface presenter module 2954 may include bar presenter module 2956. Bar presenter module 2956 may include slider bar presenter module 2958 and/or corresponding presenter module 2960.

Figure 30:
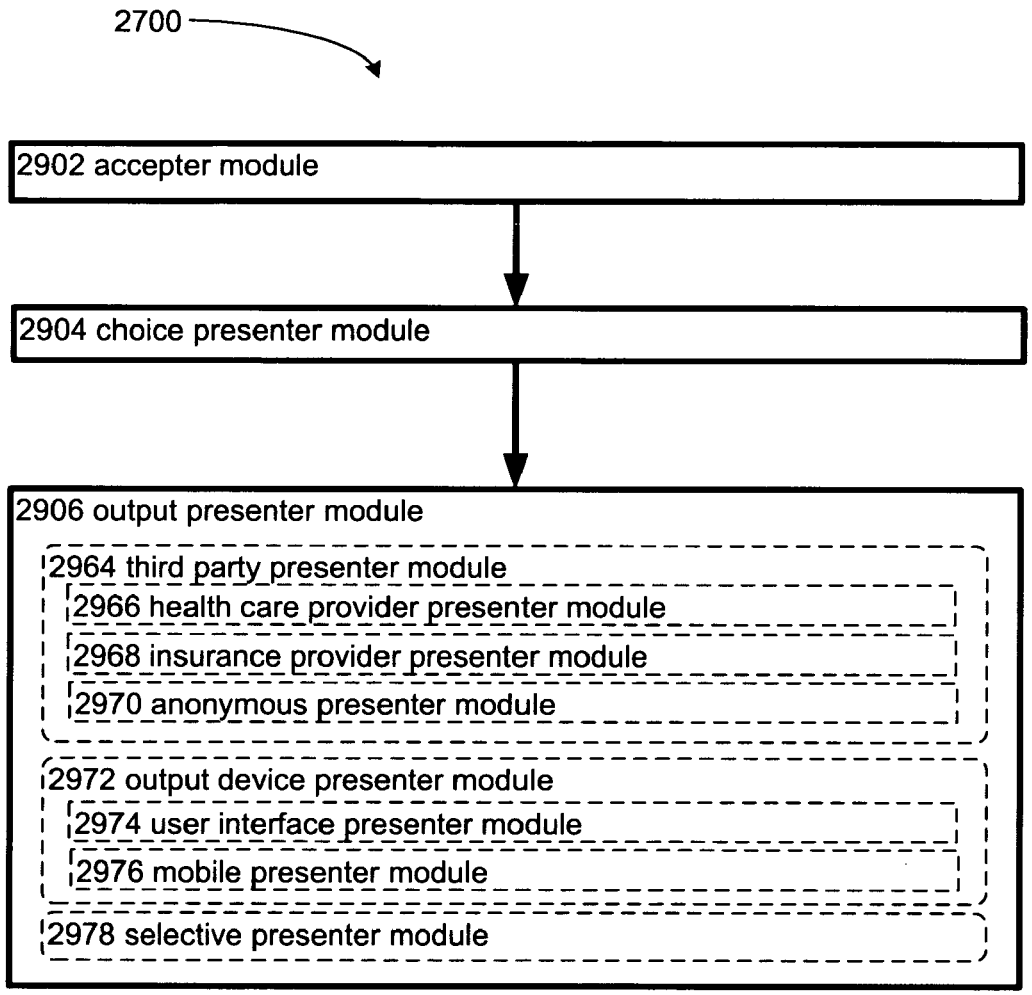
FIG. 30 illustrates certain alternative embodiments of the health services planning and matching system of FIG. 1.

FIG. 30 further illustrates system 2700 including accepter module 2902, choice presenter module 2904, and/or output presenter module 2906. Output presenter module 2906 may include third party presenter module 2964, output device presenter module 2972, and/or selective presenter module 2978. Third party presenter module 2964 may include health care provider presenter module 2966, insurance provider presenter module 2968, and/or anonymous presenter module 2970. Output device presenter module 2972 may include user interface presenter module 2974 and/or mobile presenter module 2976.

Figure 31:
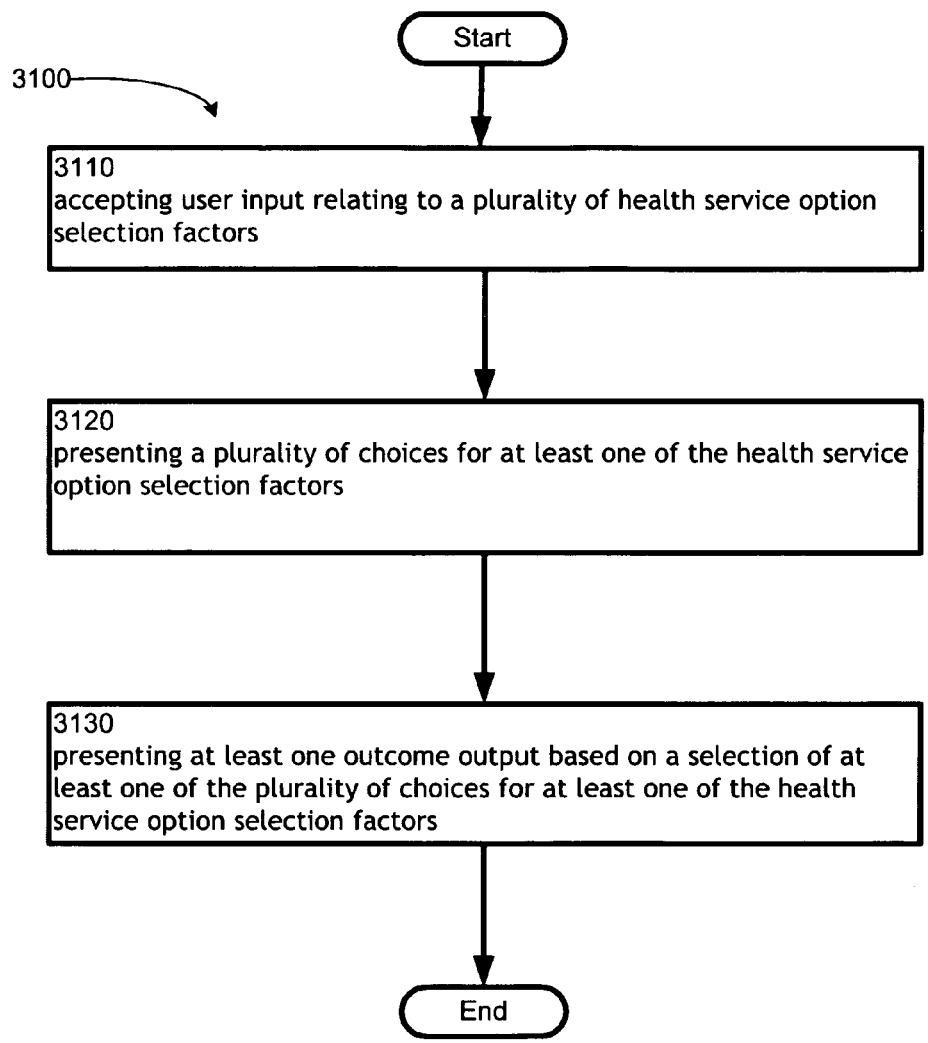
FIG. 31 illustrates an example of an operational flow representing example operations related to health services planning and matching, which may serve as a context for introducing one or more processes and/or devices described herein.

FIG. 31 illustrates an operational flow 3100 representing example operations related to accepting user input relating to a plurality of health service option selection factors, presenting a plurality of choices for at least one of the health service option selection factors, and presenting at least one outcome output based on a selection of at least one of the plurality of choices for at least one of the health service option selection factors. In FIG. 31 and in following figures that include various examples of operational flows, discussion and explanation may be provided with respect to the above-described examples of FIGS. 27 through 30, and/or with respect to other examples and contexts. However, it should be understood that the operational flows may be executed in a number of other environments and contexts, and/or in modified versions of FIGS. 27 through 30. Also, although the various operational flows are presented in the sequence(s) illustrated, it should be understood that the various operations may be performed in other orders than those which are illustrated, or may be performed concurrently.

After a start operation, the operational flow 3100 moves to an operation 3110. Operation 3110 depicts to accepting user input relating to a plurality of health service option selection factors. For example, as shown in FIGS. 27 through 30, accepter module 2902 may accept user input relating to a plurality of health service option selection factors. In an embodiment, accepter module 2902 can accept, for example, an individual's preference regarding a health service option, such as tolerance for at least one side effect. The user 140 may be a patient newly informed of a medical condition, an individual experiencing one or more symptoms, a health care practitioner investigating health care services options for a patient in their care, a health care maintenance organization planning for the care of a patient, or the like. An indication of at least one health-related status of an individual may also include a desire for cosmetic enhancement, pregnancy, or improvement in athletic performance. In some instances, accepter module 2902 may include a computer processor.

Then, operation 3120 depicts presenting a plurality of choices for at least one of the health service option selection factors. For example, as shown in FIGS. 27 through 30, choice presenter module 2904 may present a plurality of choices for at least one of the health service option selection factors. In an embodiment, choice presenter module 2904 can present multiple choices for health service option selection factors including potential embarrassment, distance to the health service option provider, and health service option cost. This presentation may allow the individual and/or user to input a preference for each of the factors. In some instances, choice presenter module 2904 may include a computer processor.

Then, operation 3130 depicts presenting at least one outcome output based on a selection of at least one of the plurality of choices for at least one of the health service option selection factors. For example, as shown in FIGS. 27 through 30, output presenter module 2906 may present at least one outcome output based on a selection of at least one of the plurality of choices for at least one of the health service option selection factors. In an embodiment, output presenter module 2906 can present a recommended health service option (e.g., a certain physician, a medication, and/or a certain procedure) based on the individual's preferences for the health service option. In some instances, output presenter module 2906 may include a computer processor.

Figure 32:
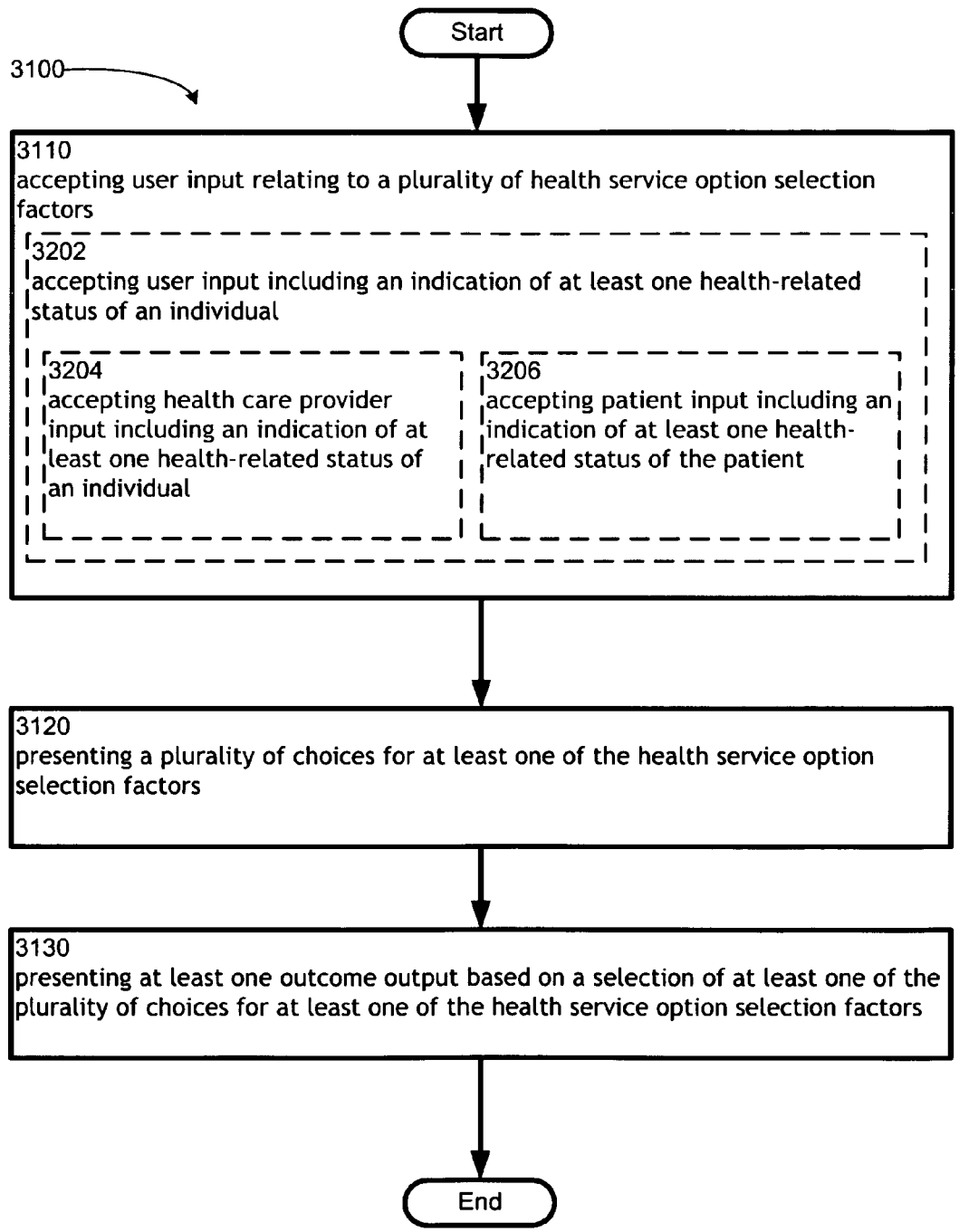
FIG. 32 illustrates an alternative embodiment of the operational flow of FIG. 31.

FIG. 32 illustrates alternative embodiments of the example operational flow 3100 of FIG. 31. FIG. 32 illustrates example embodiments where operation 3110 may include at least one additional operation. Additional operations may include operation 3202, operation 3204, and/or operation 3206.

Operation 3202 illustrates to accepting user input including an indication of at least one health-related status of an individual. For example, as shown in FIGS. 27 through 30, device 102 and/or user input accepter module 2908 may accept user input including an indication of at least one health-related status of an individual. For example, user input accepter module 2908 may accept from user 140 a symptom, a disease name, a diagnosis name, a health service procedure name, or the like. Virtually any health-related term may be accepted; each health-related term will serve as an indication of at least one health-related status of the individual. For example, accepting user input in the form of "facelift" may be an indication of a desire for cosmetic surgery. This may be used to determine health care services options for facelift services including treatment centers. Specific options for service providers including plastic surgeons, hospitals, plastic surgery resorts, or the like may also be determined. Options other than plastic surgery may also be determined based on this user input, such as peels, dermabrasion, or the like. Some examples of user input may include patient input, health maintenance organization input, insurer input, as well as third party input, such as parent input and/or spouse input. In some instances, user input accepter module 2908 may include a computer processor.

Further, operation 3204 illustrates to accepting health care provider input including an indication of at least one health-related status of an individual. For example, as shown in FIGS. 27 through 30, health care provider accepter module 2910 may accept user input including an indication of at least one health-related status of an individual. For example, health care provider accepter module 2910 may accept from user 140 a symptom, a disease name, a diagnosis name, a health service procedure name, or the like. Virtually any health-related term may be accepted; each health-related term will serve as an indication of at least one health-related status of the individual. For example, accepting user input in the form of "facelift" may be an indication of a desire for cosmetic surgery. This may be used to determine health care services options for facelift services including treatment centers. Specific options for service providers including plastic surgeons, hospitals, plastic surgery resorts, or the like may also be determined. Options other than plastic surgery may also be determined based on this user input, such as peels, dermabrasion, or the like. Some examples of user input may include patient input, health maintenance organization input, insurer input, as well as third party input, such as parent input and/or spouse input. In some instances, health care provider accepter module 2910 may include a computer processor.

Further, operation 3206 illustrates to accepting patient input including an indication of at least one health-related status of the patient. For example, as shown in FIGS. 27 through 30, device 102 and/or patient input accepter module 2912 may accept patient input including an indication of at least one health-related status of the patient. For example, a diabetes patient may input "type II diabetes" when looking for an endocrinologist to provide care for her condition. In some embodiments, a set of symptoms may be entered by a patient, and an optional medical expert system function in the patient input accepter module 2912 may be accessed to generate a list of possible diagnoses for the symptom set, and/or health care providers capable of providing an appropriate service. For example, if a patient enters skin rash, fever, and neck stiffness, device 102 and/or patient input accepter module 2912 may list meningitis as one possible diagnosis for the patient. Such a patient may be merely experiencing symptoms and not yet under the care of a health care provider. In some instances, patient input accepter module 2912 may include a computer processor.

Figure 33:
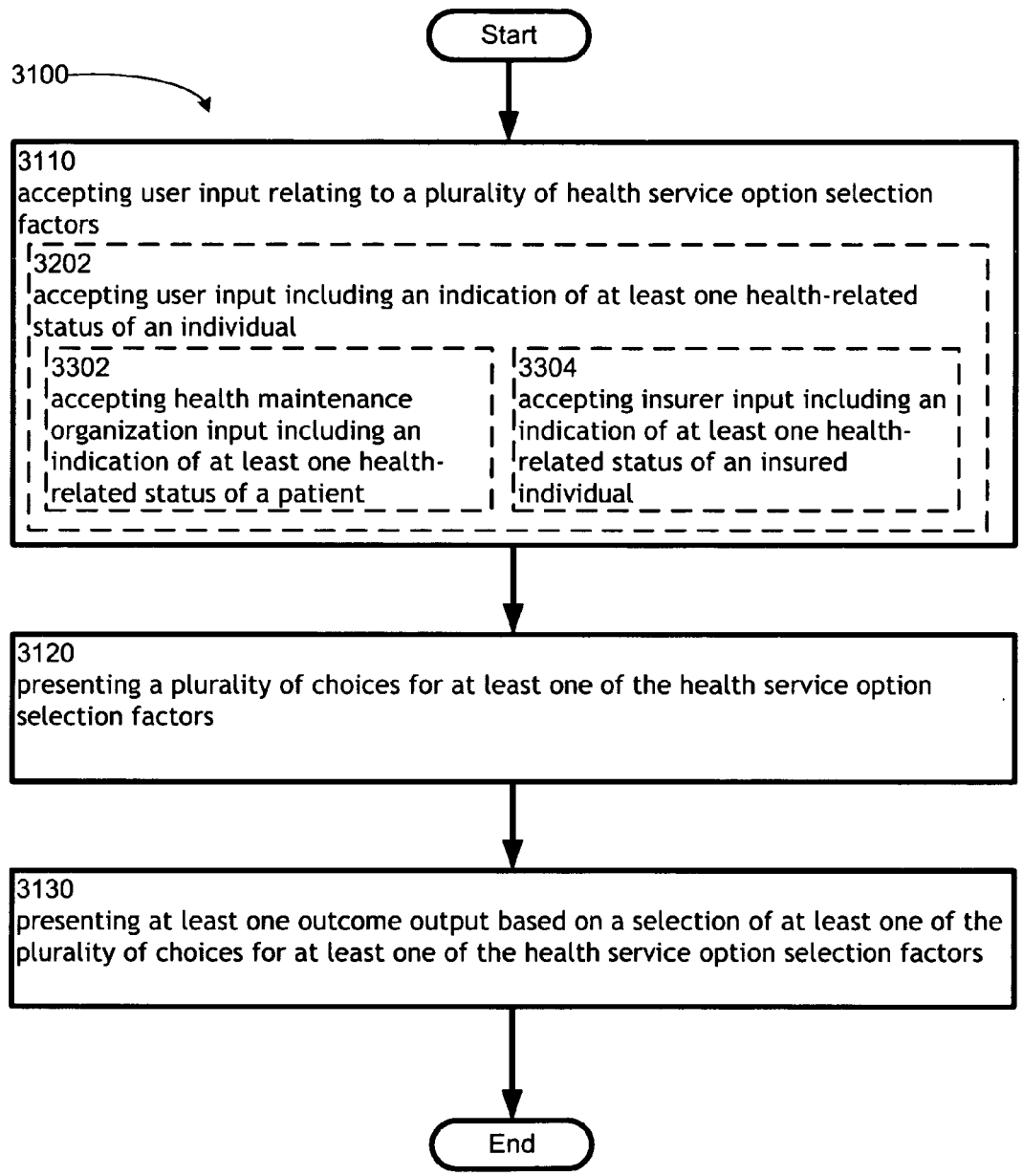
FIG. 33 illustrates an alternative embodiment of the operational flow of FIG. 31.

FIG. 33 illustrates alternative embodiments of the example operational flow 3100 of FIG. 31. FIG. 33 illustrates example embodiments where operation 3110 may include at least one additional operation. Additional operations may include operation 3302, and/or operation 3304.

Further, operation 3302 illustrates to accepting health maintenance organization input including an indication of at least one health-related status of a patient. For example, as shown in FIGS. 27 through 30, device 102 and/or organization input accepter module 2914 may accept health maintenance organization input including an indication of at least one health-related status of a patient. For example, a health maintenance organization may input "carpal tunnel syndrome" to find physical therapists providing services for patients with this condition. If the health care maintenance organization then chooses a particular determined health service option, such as stretching exercises and application of a wrist brace, a geographical preference may be entered such that the device 102 and/or organization input accepter module 2914 can find one or more appropriate health care providers of carpal tunnel therapy in the desired geographic area. In some instances, organization input accepter module 2914 may include a computer processor.

Further, operation 3304 illustrates to accepting insurer input including an indication of at least one health-related status of an insured individual. For example, as shown in FIGS. 27 through 30, device 102 and/or insurer input accepter module 2916 may accept insurer input including an indication of at least one health-related status of an insured individual. For example, an insurer may input "congestive heart failure" to identify risk factors for congestive heart failure among individuals in a general population or a subpopulation. In one embodiment, insurer input accepter module 2916 may accept and/or determine that coronary artery disease, smoking, diabetes, hypertension, and high cholesterol are significant risk factors for congestive heart failure among individuals aged 55 to 85 in the United States. Stress-test monitoring of coronary artery disease may be identified as one of the options for congestive heart failure prevention, and upon selection of this option by insurer 272, local cardiologists may be invited to provide competitive rates for providing stress tests to insured individuals. In some instances, insurer input accepter module 2916 may include a computer processor.

Figure 34:
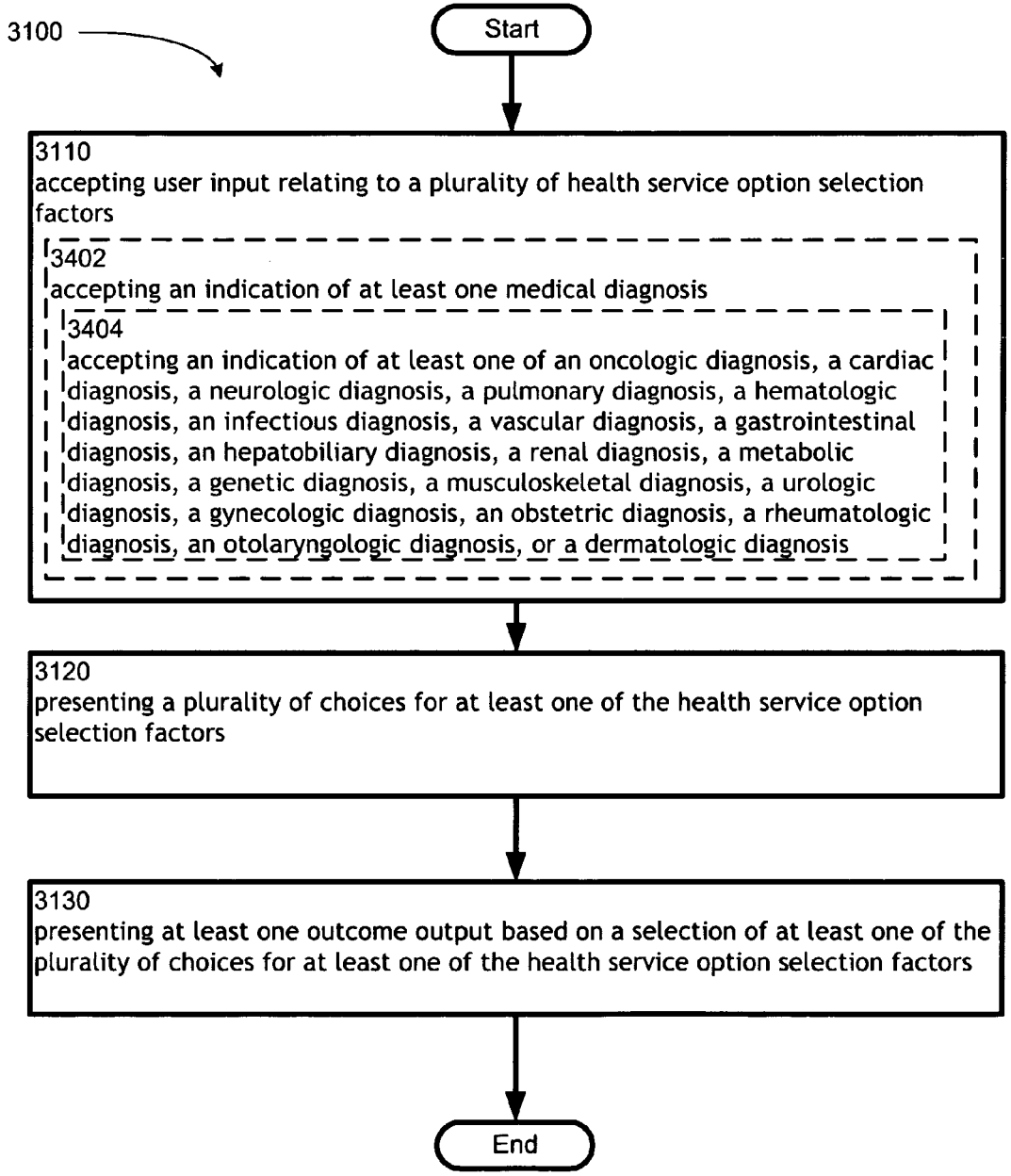
FIG. 34 illustrates an alternative embodiment of the operational flow of FIG. 31.

FIG. 34 illustrates alternative embodiments of the example operational flow 3100 of FIG. 31. FIG. 34 illustrates example embodiments where operation 3110 may include at least one additional operation. Additional operations may include operation 3402, and/or operation 3404.

Operation 3402 illustrates to accepting an indication of at least one medical diagnosis. For example, as shown in FIGS. 27 through 30, device 102 and/or medical diagnosis accepter module 2918 may accept an indication of at least one medical diagnosis. For example, an individual may input "glaucoma" to determine treatment steps to take once a diagnosis is received. Often a physician will recommend a course of treatment upon making a diagnosis, but a patient may also want to know about alternative treatments, including alternatives to Western medical treatment. In this example of a glaucoma diagnosis, medical diagnosis accepter module 2918 may accept and/or determine medical treatment options including beta blockers, prostaglandin analogs, alpha-adrenergic agonists, carbonic anhydrase inhibitors, as well as alternative treatment options including aerobic exercise, marijuana therapy and/or acupuncture therapy. In some instances, medical diagnosis accepter module 2918 may include a computer processor.

Further, operation 3404 illustrates to accepting an indication of at least one of an oncologic diagnosis, a cardiac diagnosis, a neurologic diagnosis, a pulmonary diagnosis, a hematologic diagnosis, an infectious diagnosis, a vascular diagnosis, a gastrointestinal diagnosis, an hepatobiliary diagnosis, a renal diagnosis, a metabolic diagnosis, a genetic diagnosis, a musculoskeletal diagnosis, a urologic diagnosis, a gynecologic diagnosis, an obstetric diagnosis, a rheumatologic diagnosis, an otolaryngologic diagnosis, or a dermatologic diagnosis. For example, as shown in FIGS. 27 through 30, device 102 and/or diagnosis accepter module 2920 may accept an indication of at least one of an oncologic diagnosis, a cardiac diagnosis, a neurologic diagnosis, a pulmonary diagnosis, a hematologic diagnosis, an infectious diagnosis, a vascular diagnosis, a gastrointestinal diagnosis, an hepatobiliary diagnosis, a renal diagnosis, a metabolic diagnosis, a genetic diagnosis, a musculoskeletal diagnosis, a urologic diagnosis, a gynecologic diagnosis, an obstetric diagnosis, a rheumatologic diagnosis, an otolaryngologic diagnosis, or a dermatologic diagnosis. For example, a caretaker may input "Alzheimer's disease" as a neurologic diagnosis to determine treatment steps to take once an Alzheimer's diagnosis is received. Often a person caring for an individual with Alzheimer's will not know what to do or where to turn for help in caring for the affected individual. Inputting "Alzheimer's disease" into the diagnosis accepter module 2920, for example, may result in a determination of treatment options including drug therapy, e.g., including memantine, glantamine, rivastigmine, doenpezil, and/or tacrine; and/or non-pharmacological behavioral-management approaches such as playing music of the person's choosing, one-on-one interaction, playing videotapes of family members, walking and light exercise, and pet therapy. In some instances, diagnosis accepter module 2920 may include a computer processor.

Figure 35:
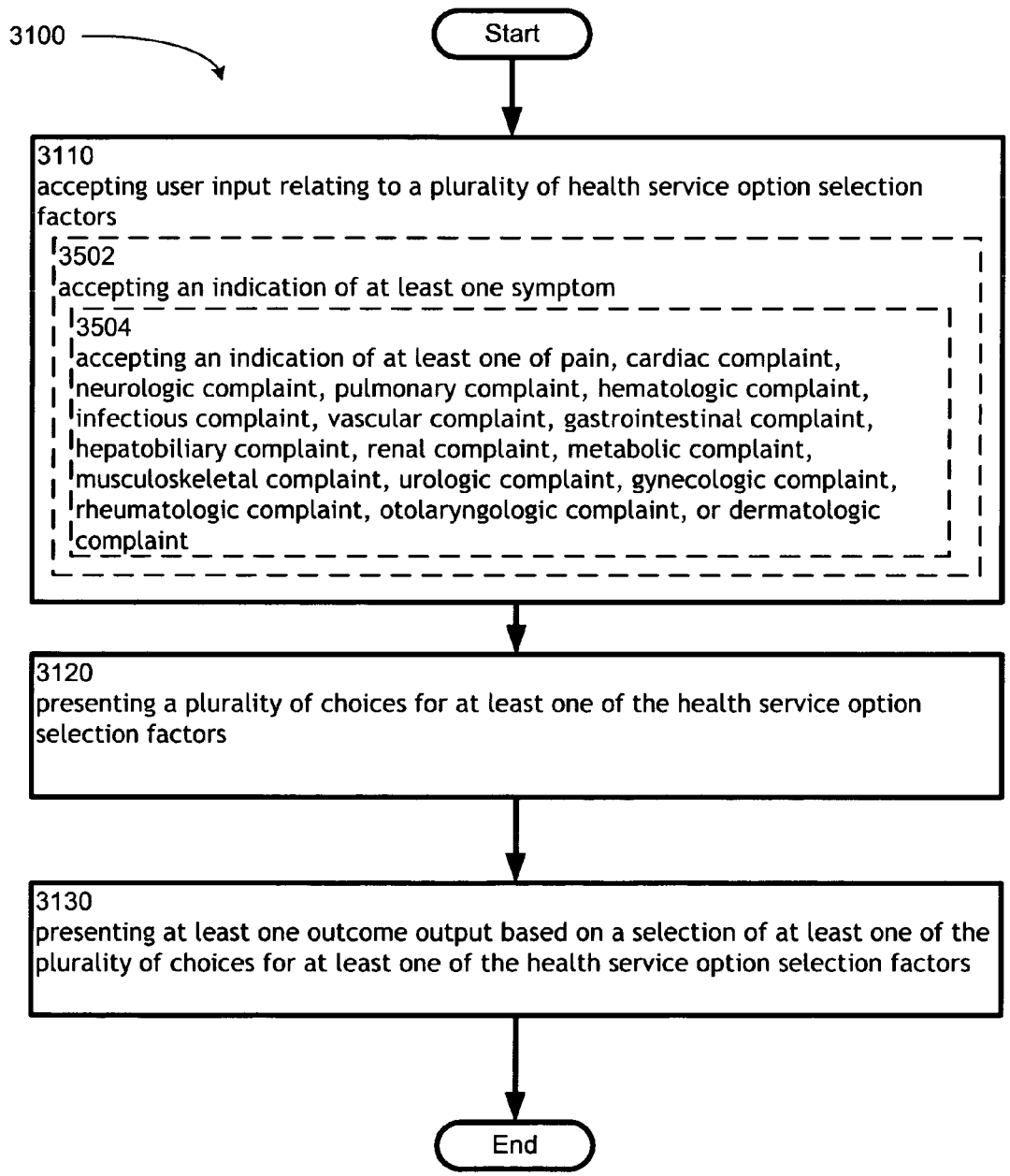
FIG. 35 illustrates an alternative embodiment of the operational flow of FIG. 31.

FIG. 35 illustrates alternative embodiments of the example operational flow 3100 of FIG. 31. FIG. 35 illustrates example embodiments where operation 3110 may include at least one additional operation. Additional operations may include operation 3502, and/or operation 3504.

Operation 3502 illustrates to accepting an indication of at least one symptom. For example, as shown in FIGS. 27 through 30, device 102 and/or symptom accepter module 2922 may accept an indication of at least one symptom. In one embodiment, symptom accepter module 2922 may accept a symptom such as "decreased night vision." Symptom accepter module 2922 may then determine a set of testing and treatment steps. For example, one testing step may be to look at decreased night vision as a side effect of various medicines. Another testing step may include cataract testing, such as a refraction test, a slitlamp exam, a contrast sensitivity test, a glare disability test, a potential acuity test, a dilated fundus exam, or the like. Treatment options for cataracts may also be determined at this time. Alternatively, user 140 may opt to defer listing of treatment options until a diagnosis is obtained based on the testing options presented. In this scenario, if the user 140 discovers that she has cataracts, treatment options including surgery may be determined and presented to user 140. In some instances, symptom accepter module 2922 may include a computer processor.

Further, operation 3504 illustrates to accepting an indication of at least one of pain, cardiac complaint, neurologic complaint, pulmonary complaint, hematologic complaint, infectious complaint, vascular complaint, gastrointestinal complaint, hepatobiliary complaint, renal complaint, metabolic complaint, musculoskeletal complaint, urologic complaint, gynecologic complaint, rheumatologic complaint, otolaryngologic complaint, or dermatologic complaint. For example, as shown in FIGS. 27 through 30, device 102 and/or complaint accepter module 2924 may accept an indication of at least one of pain, cardiac complaint, neurologic complaint, pulmonary complaint, hematologic complaint, infectious complaint, vascular complaint, gastrointestinal complaint, hepatobiliary complaint, renal complaint, metabolic complaint, musculoskeletal complaint, urologic complaint, gynecologic complaint, rheumatologic complaint, otolaryngologic complaint, or dermatologic complaint. In one embodiment, complaint accepter module 2924 may accept "earache" as an otolaryngologic complaint. In this example, treatment planning module may determine an otoscope examination to diagnose infection of the outer or middle ear (e.g., otitis externa or otitis media), and treatment steps including antibiotic ear drops in the case of otitis externa, and/or oral antibiotics in the case of otitis media. Upon selection of a desired determined examination and/or treatment, health care services matching unit 120 may search a health care services provider database 222 for a list of those providers with expertise in the ear/nose/throat specialty and with offices in the geographic area near the user 140. The resulting subset of local ear/nose/throat specialists may then be invited to bid on the cost of services for examination and/or treatment of user 140, thereby providing a matching system for procurement of the desired health service option. In some instances, complaint accepter module 2924 may include a computer processor.

Figure 36:
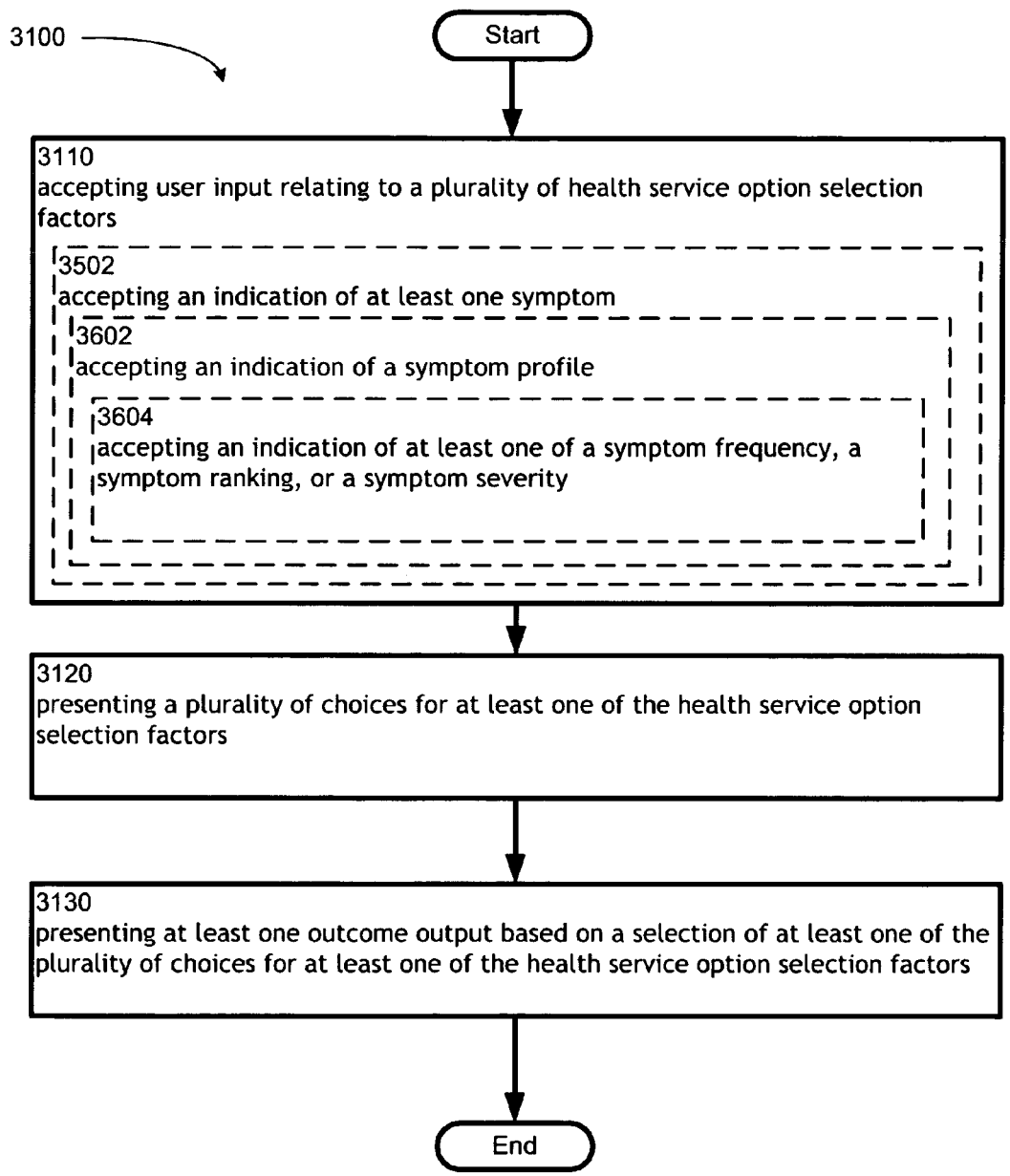
FIG. 36 illustrates an alternative embodiment of the operational flow of FIG. 31.

FIG. 36 illustrates alternative embodiments of the example operational flow 3100 of FIG. 31. FIG. 36 illustrates example embodiments where operation 3110 may include at least one additional operation. Additional operations may include operation 3602, and/or operation 3604.

Further, operation 3602 illustrates to accepting an indication of a symptom profile. For example, as shown in FIGS. 27 through 30, device 102 and/or symptom profile accepter module 2926 may accept an indication of a symptom profile. In one embodiment, symptom profile accepter module 2926 may accept a constellation of symptoms that suggests a diagnosis, such as a set of typical symptoms of a known disease. See, e.g., U.S. patent publication 2008/0091086. For example, symptom profile accepter module 2926 may accept a set of one or more of the following symptoms: bull's-eye rash, fever, stiff neck, headache, body aches, fatigue, or redness and swelling in the joints. Based on such a constellation of symptoms, testing and/or treatment for Lyme disease may be determined. In some instances, symptom profile accepter module 2926 may include a computer processor.

Further, operation 3604 illustrates to accepting an indication of at least one of a symptom frequency, a symptom ranking, or a symptom severity. For example, as shown in FIGS. 27 through 30, device 102 and/or symptom characteristic accepter module 2928 may accept an indication of at least one of a symptom frequency, a symptom ranking, or a symptom frequency and severity. In one embodiment, symptom characteristic accepter module 2928 may accept an indication of asthma symptom severity. The National Asthma Education Program, which produces the U.S.-based asthma treatment guidelines, classifies asthma by its severity, a scheme commonly used by most health professionals. This approach also guides asthma treatment. In some instances, symptom characteristic accepter module 2928 may include a computer processor.

Classification of asthma by severity is based on frequency and severity of asthma symptoms, along with peak flow readings. Levels are referred to as steps, as follows: Step 1: Mild Intermittent; at this level, asthma symptoms occur less than 2 times a week during waking hours and less than twice a month during the night. In between asthma attacks, no symptoms occur at all, and the attacks themselves are generally brief, though their intensity can vary. Peak flow variability is less than 20 percent. Step 2: Mild Persistent; at this level, asthma symptoms occur more than twice a week, but not as often as daily. They may occasionally wake one up at night, but that happens less than 2 times a month. Asthma attacks may interfere with activity temporarily. Peak flow tends to be between 20 and 30 percent. Step 3: Moderate Persistent; at this level, asthma begins to interfere more with daily living. Symptoms are seen every single day, and use of a quick-relief inhaler daily may be required. Asthma attacks occur at least twice a week and often interfere with activity. They may last for days at a time. Individuals may wake up 1 or more times a week with symptoms. Peak flow rate varies by more than 30 percent. Step 4: Severe Persistent; this is the most severe form of asthma and at this level, symptoms are basically continuous. Activity is severely limited and asthma attacks and night symptoms are frequent. Peak flow varies by more than 30 percent.

The National Asthma Education Program advocates a stepwise approach to treating asthma in adults and children older than age 5, based on the types of asthma severity described above. For instance, mild intermittent asthma is usually treated only with quick-relief medicines, while severe persistent asthma is treated with one or more daily controller medicines and frequent use of quick-relief medicines. Accordingly, symptom characteristic accepter module 2928 may present appropriate treatment options for each type of asthma.

Symptom ranking may include priority rankings of symptoms, such as those experienced with gastrointestinal reflux disease (GERD). Heartburn, regurgitation, and dysphagia are considered typical symptoms of GERD. For example, it has been shown that high priority ranking of the symptom dysphagia is predictive of the presence of an esophageal stricture, but has a negative association with abnormal manometric and pH studies. In contrast, high priority ranking of the symptom heartburn and regurgitation are positively associated with abnormal manometric and pH results. See Martinez-Serna et al., "Symptom Priority Ranking in the Care of Gastroesophageal Reflux: A Review of 1,850 Cases," Dig Dis, 17:219-224 (1999).

Figure 37:
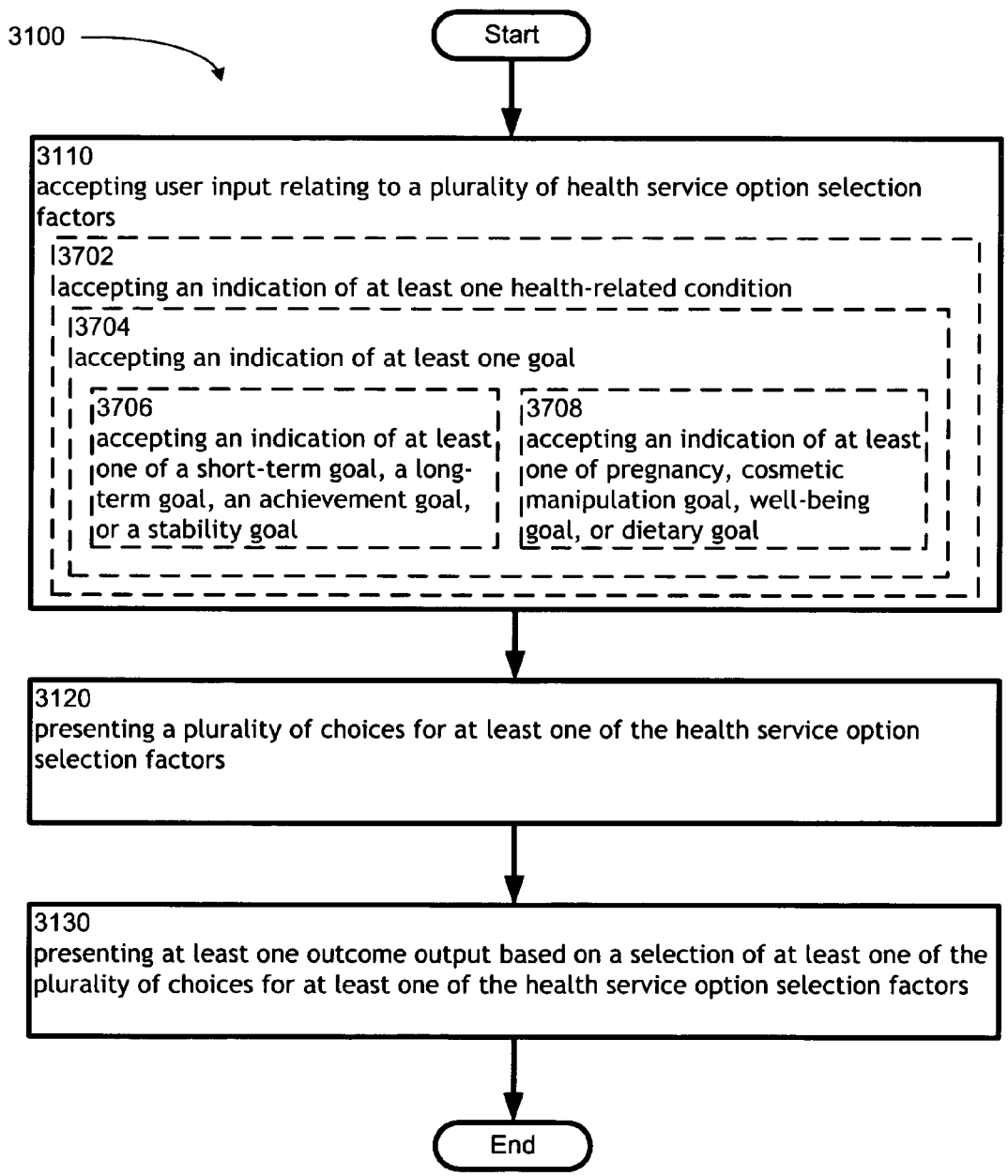
FIG. 37 illustrates an alternative embodiment of the operational flow of FIG. 31.

FIG. 37 illustrates alternative embodiments of the example operational flow 3100 of FIG. 31. FIG. 37 illustrates example embodiments where operation 3110 may include at least one additional operation. Additional operations may include operation 3702, operation 3704, operation 3706, and/or operation 3708.

Operation 3702 illustrates to accepting an indication of at least one health-related condition. For example, as shown in FIGS. 27 through 30, device 102 and/or condition accepter module 2930 may accept an indication of at least one health-related condition. In one embodiment, treatment planning module 104 may accept an indication of a health-related condition such as "weight-loss." In such a case, condition accepter module 2930 and/or determiner module 2908 may determine evaluative and treatment services such as nutritionist services or dietetics services. Nutraceutical options may also be determined. In some instances, condition accepter module 2930 may include a computer processor.

Further, operation 3704 illustrates to accepting an indication of at least one goal. For example, as shown in FIGS. 27 through 30, device 102 and/or goal accepter module 2932 may accept an indication of at least one goal. In one embodiment, device 102 and/or goal accepter module 2932 may accept an indication of an athletic performance goal, such as increased aerobic conditioning. Determined health service options for this goal may include exercise training services, nutrition services, sports psychology services, or the like. In some instances, goal accepter module 2932 may include a computer processor.

Further, operation 3706 illustrates to accepting an indication of at least one of a short-term goal, a long-term goal, an achievement goal, or a stability goal. For example, as shown in FIGS. 27 through 30, device 102 and/or goal characteristic accepter module 2934 may accept an indication of at least one of a short-term goal, a long-term goal, an achievement goal, or a stability goal. In one embodiment, goal characteristic accepter module 2934 may accept an achievement goal, such as stopping smoking cigarettes. In this example, goal characteristic accepter module 2934 may determine nicotine replacement therapy, such as over-the-counter anti-smoking aids such as nicotine gum. Another nicotine replacement therapy is the nicotine patch. Other alternatives to combat the urge to smoke include support and counseling services, hypnosis, acupuncture, or the like. In some instances, goal characteristic accepter module 2934 may include a computer processor.

A stability goal may include maintenance programs whereby an individual is able to achieve a goal with a degree of consistency over time. For example, a stability goal for a diabetic may include maintaining her blood sugar within a recommended range for a given period of months or years.

Another example of a stability goal is maintaining one's LDL cholesterol at a low level over a certain period of time.

Further, operation 3708 illustrates accepting an indication of at least one of pregnancy, cosmetic manipulation goal, well-being goal, or dietary goal. For example, device 102 and/or goal characteristic accepter module 2936 may accept an indication of at least one of pregnancy, cosmetic manipulation goal, well-being goal, or dietary goal. In one embodiment, goal characteristic accepter module 2936 may accept an indication of "rhinoplasty" as the cosmetic manipulation goal. In this embodiment, goal characteristic accepter module 2936 may determine various rhinoplasty options, including, for example, open rhinoplasty, closed rhinoplasty, or non-surgical rhinoplasty. In some situations, a patient/health care provider/user 140 may not be aware of the range of options available for addressing a given health-related status or health-related condition. Accordingly, the system 100, device 102, and/or goal characteristic accepter module 2936 may be useful to the user 140 in terms of discovering a range of options available to pursue. In some instances, goal characteristic accepter module 2936 may include a computer processor.

Examples of a pregnancy goal include a goal for becoming pregnant within a certain time frame, a goal for overcoming male or female infertility, a goal for ending a pregnancy, or the like. Examples of a well-being goal include a goal for stress management, a goal for depression management, a goal for sleeplessness management, a goal for anxiety management, or the like. Examples of a dietary goal include a goal for weight loss, a goal for a lower body mass index, a goal for increased muscle mass, a goal for lower dietary cholesterol intake, a goal for a diabetes-compatible diet, or the like.

Figure 38:
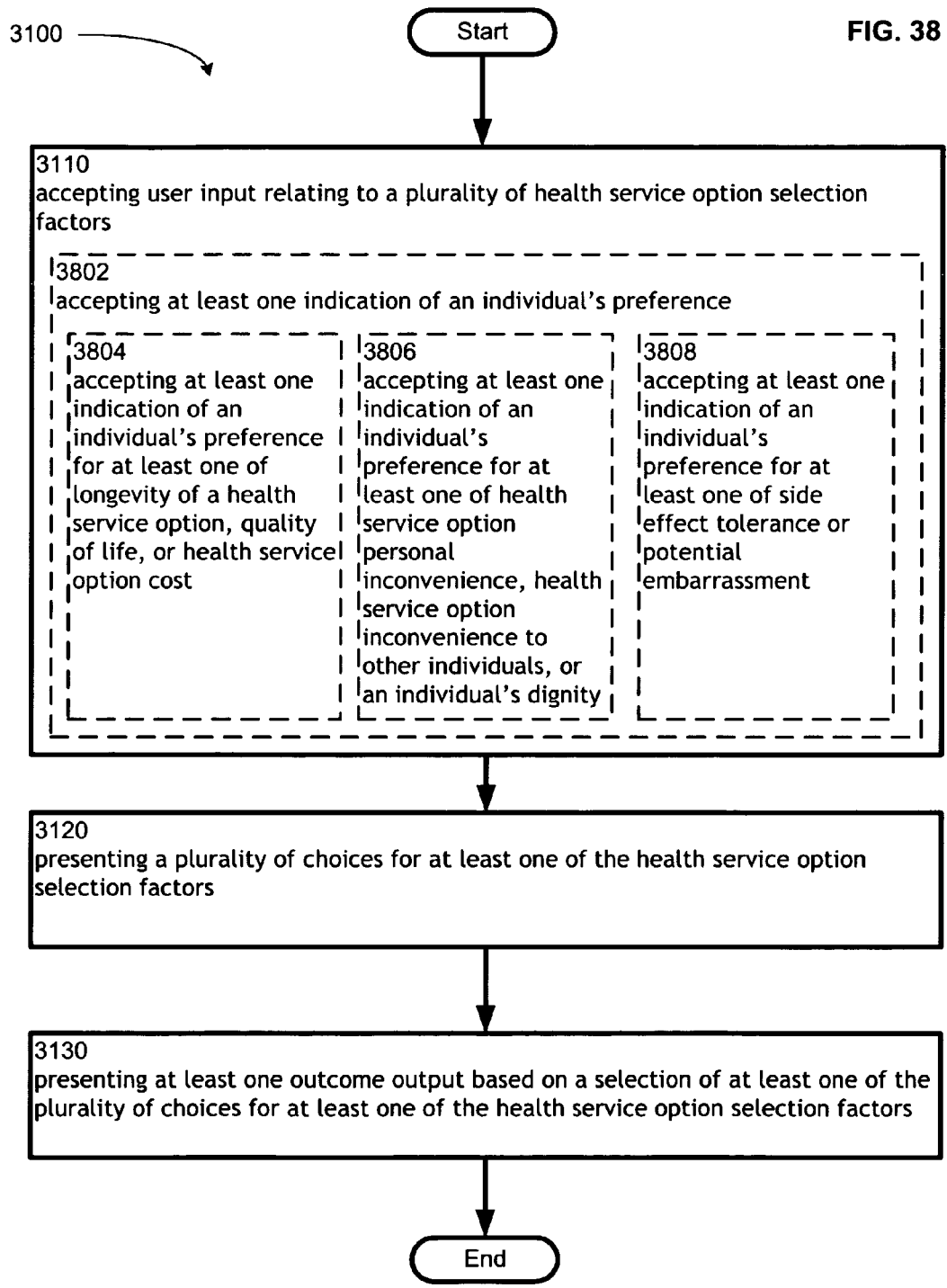
FIG. 38 illustrates an alternative embodiment of the operational flow of FIG. 31.

FIG. 38 illustrates alternative embodiments of the example operational flow 3100 of FIG. 31. FIG. 38 illustrates example embodiments where operation 3110 may include at least one additional operation. Additional operations may include operation 3802, operation 3804, operation 3806, and/or operation 3808.

Operation 3802 illustrates accepting at least one indication of an individual's preference. For example, as shown in FIGS. 27 through 30, preference accepter module 2938 can accept at least one indication of an individual's preference. In an embodiment, preference accepter module 2938 may accept an indication of an individual's preference for a low cost health service option. In some instances, preference accepter module 2938 may include a computer processor.

Further, operation 3804 illustrates accepting at least one indication of an individual's preference for at least one of longevity of a health service option, quality of life, or health service option cost. For example, as shown in FIGS. 27 through 30, option preference accepter module 2940 can accept at least one indication of an individual's preference for at least one of longevity of a health service option, quality of life, or health service option cost. In an embodiment, option preference accepter module 2940 may accept an indication of an individual's preference for a health service option cost. In this embodiment, the individual may input a preference for a health service option below a certain cost threshold based on the individual's ability to pay, for example, by utilizing the individual's medical insurance coverage. In another embodiment, option preference accepter module 2940 may accept an indication of an individual's preference for longevity of a health service option. In this embodiment, the individual may input a preference for a health service option that may be a matter of days as opposed to a matter of months. For example, the individual may indicate that a surgery and recovery taking one week is preferable to a medication regiment that may take six months. In some instances, option preference accepter module 2940 may include a computer processor.

Further, operation 3806 illustrates accepting at least one indication of an individual's preference for at least one of health service option personal inconvenience, health service option inconvenience to other individuals, or an individual's dignity. For example, as shown in FIGS. 27 through 30, convenience accepter module 2942 may accept at least one indication of an individual's preference for at least one of health service option personal inconvenience, health service option inconvenience to other individuals, or an individual's dignity. In an embodiment, convenience accepter module 2942 can accept an indication of an individual's preference for health service option personal inconvenience. In this embodiment, the individual may indicate that the individual is willing to tolerate a high inconvenience due to, for example, a high likelihood of success after experiencing a certain health service option. In some instances, convenience accepter module 2942 may include a computer processor.

Further, operation 3808 illustrates accepting at least one indication of an individual's preference for at least one of side effect tolerance or potential embarrassment. For example, as shown in FIGS. 27 through 30, tolerance accepter module 2944 may accept at least one indication of an individual's preference for at least one of side effect tolerance or potential embarrassment. In an embodiment, tolerance accepter module 2944 can accept an indication of an individual's preference for side effect tolerance. In this embodiment, the individual may indicate a medium tolerance for a side effect (e.g., as long as the side effects are not severe). In some instances, tolerance accepter module 2944 may include a computer processor.

Figure 39:
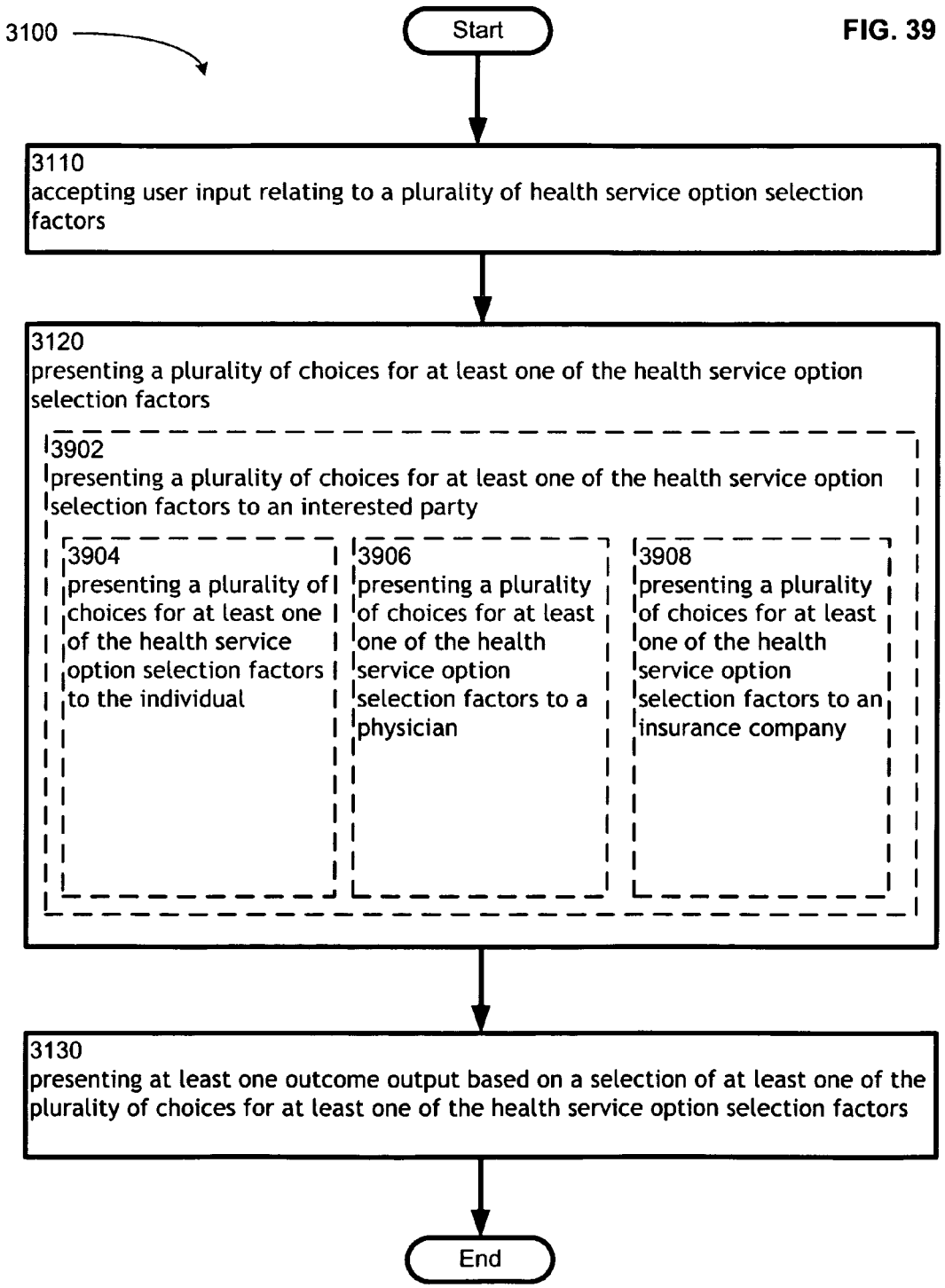
FIG. 39 illustrates an alternative embodiment of the operational flow of FIG. 31.

FIG. 39 illustrates alternative embodiments of the example operational flow 3100 of FIG. 31. FIG. 39 illustrates example embodiments where operation 3120 may include at least one additional operation. Additional operations may include operation 3902, operation 3904, operation 3906, and/or operation 3908.

Operation 3902 illustrates presenting a plurality of choices for at least one of the health service option selection factors to an interested party. For example, as shown in FIGS. 27 through 30, party presenter module 2946 may present a plurality of choices for at least one of the health service option selection factors to an interested party. In an embodiment, party presenter module 2946 can present a plurality of choices, such as individual preferences regarding cost and side effects of a potential health service option. Some examples of health service option selection factors may include health service option costs, amount of pain associated with the health service option, potential side effects, and/or location of a health service option. In some instances, party presenter module 2946 may include a computer processor.

Further, operation 3904 illustrates presenting a plurality of choices for at least one of the health service option selection factors to the individual. For example, as shown in FIGS. 27 through 30, individual presenter module 2948 may present a plurality of choices for at least one of the health service option selection factors to the individual. In an embodiment, individual presenter module 2948 can present a choice for personal preference for pain and discomfort associated with at least one of the health service option selection factors to the individual needing the health service option. In some instances, individual presenter module 2948 may include a computer processor.

Further, operation 3906 illustrates presenting a plurality of choices for at least one of the health service option selection factors to a physician. For example, as shown in FIGS. 27 through 30, physician presenter module 2950 may present a plurality of choices for at least one of the health service option selection factors to a physician. In an embodiment, physician presenter module 2950 can present a plurality of choices for an individual's personal preference for side effects and discomfort associated with at least one of the health service option selection factors to a physician. Presenting the plurality of choices to a physician may serve to educate the physician in counseling and/or advising the individual regarding the health service option possibilities. In some instances, physician presenter module 2950 may include a computer processor.

Further, operation 3908 illustrates presenting a plurality of choices for at least one of the health service option selection factors to an insurance company. For example, as shown in FIGS. 27 through 30, insurance presenter module 2952 may present a plurality of choices for at least one of the health service option selection factors to an insurance company. In an embodiment, insurance presenter module 2952 can present a plurality of choices for an individual's personal preference for side effects and health service option location associated with at least one of the health service option selection factors to an insurance company. Presenting the plurality of choices to an insurance company may serve to help the insurance company determine the proper amount of health service option coverage. In some instances, physician presenter module 2950 may include a computer processor.

Figure 40:
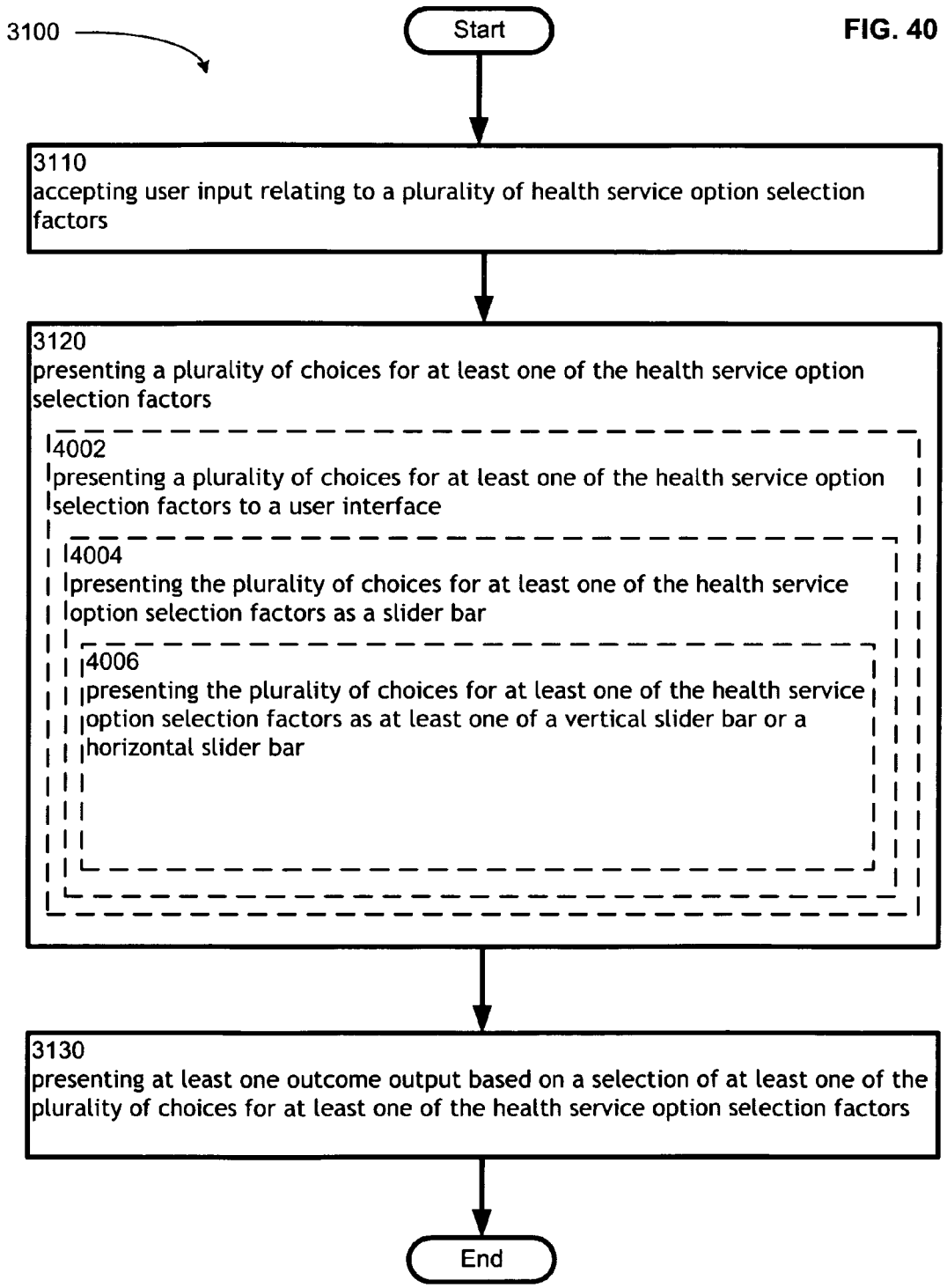
FIG. 40 illustrates an alternative embodiment of the operational flow of FIG. 31.

FIG. 40 illustrates alternative embodiments of the example operational flow 3100 of FIG. 31. FIG. 40 illustrates example embodiments where operation 3120 may include at least one additional operation. Additional operations may include operation 4002, operation 4004, and/or operation 4006.

Operation 4002 illustrates presenting a plurality of choices for at least one of the health service option selection factors to a user interface. For example, as shown in FIGS. 27 through 30, interface presenter module 2954 may present a plurality of choices for at least one of the health service option selection factors to a user interface. A user interface may include means by which an individual may interact with a system. Some examples of a user interface may include a touchscreen, a graphical user interface, a tactile interface, and/or a live user interface. In an embodiment, interface presenter module 2954 may present a plurality of choices for at least one of the health service option selection factors to a touchscreen device. In some instances, interface presenter module 2954 may include a computer processor.

Further, operation 4004 illustrates presenting the plurality of choices for at least one of the health service option selection factors as a slider bar. For example, as shown in FIGS. 27 through 30, bar presenter module 2956 may present the plurality of choices for at least one of the health service option selection factors as a slider bar. A slider bar may include an object in a graphical user interface with which a user may set a value by moving an indicator. A slider bar may be used to adjust a value without changing a display format and/or other information on a screen. In an embodiment, bar presenter module 2956 can present a health service option selection factor choice for an individual's preferred cost for a health service option as a slider bar (or a slider widget). In this embodiment, one end of the slider bar may indicate a low cost while the opposite end of the slider bar may indicate a high cost. Presenting the choices as a slider bar may serve to allow the individual to compare how a factor may affect a health service option (e.g., cost). In some instances, bar presenter module 2956 may include a computer processor.

Further, operation 4006 illustrates presenting the plurality of choices for at least one of the health service option selection factors as at least one of a vertical slider bar or a horizontal slider bar. For example, as shown in FIGS. 27 through 30, slider bar presenter module 2958 may present the plurality of choices for at least one of the health service option selection factors as at least one of a vertical slider bar or a horizontal slider bar. In an embodiment, slider bar presenter module 2958 can present a plurality of choices as a series of horizontal slider bars. In this embodiment, each slider bar may represent one health service option factor where each factor may be adjusted to assist in selecting a health service option for an individual. In some instances, slider bar presenter module 2958 may include a computer processor.

Figure 41:
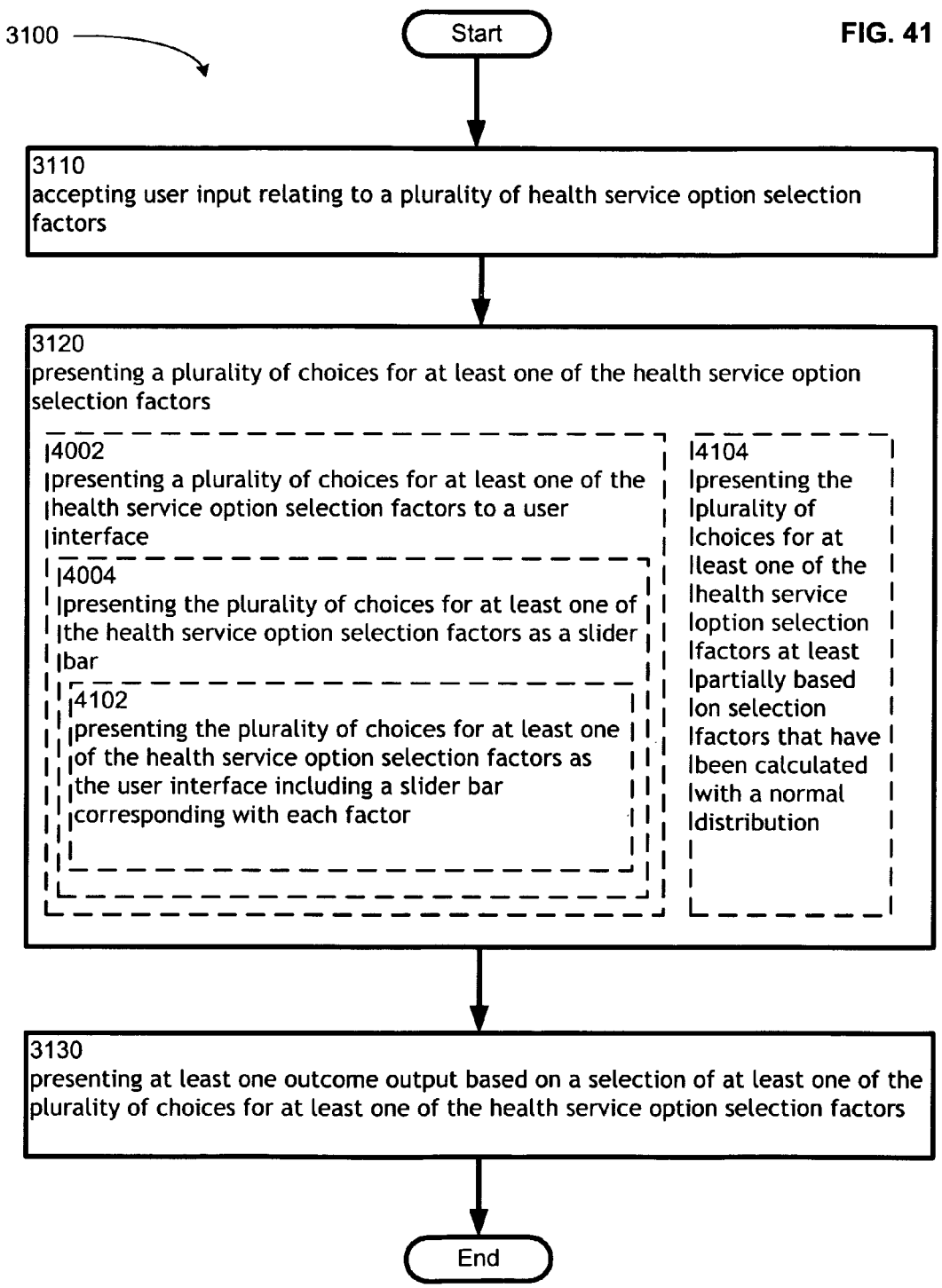
FIG. 41 illustrates an alternative embodiment of the operational flow of FIG. 31.

FIG. 41 illustrates alternative embodiments of the example operational flow 3100 of FIG. 31. FIG. 41 illustrates example embodiments where operation 3120 may include at least one additional operation. Additional operations may include operation 4102, and/or operation 4104.

Further, operation 4102 illustrates presenting the plurality of choices for at least one of the health service option selection factors as the user interface including a slider bar corresponding with each factor. For example, as shown in FIGS. 27 through 30, corresponding presenter module 2960 may present the plurality of choices for at least one of the health service option selection factors as the user interface including a slider bar corresponding with each factor. In an embodiment, corresponding presenter module 2960 can present a plurality of choices as a series of horizontal slider bars. In this embodiment, each slider bar may correspond with one health service option factor where each factor may be adjusted to assist in selecting a health service option for an individual. Additionally, using multiple slider bars may serve to allow for experimenting by the individual by varying one slider bar while holding the result and/or the other slider bars constant in order to see the effect. In some instances, corresponding presenter module 2960 may include a computer processor.

Operation 4104 illustrates presenting the plurality of choices for at least one of the health service option selection factors at least partially based on selection factors that have been calculated with a normal distribution. For example, as shown in FIGS. 27 through 30, distribution presenter module 2962 can present the plurality of choices for at least one of the health service option selection factors at least partially based on selection factors that have been calculated with a normal distribution. A normal distribution may include a continuous probability distribution describing data that clusters around a mean or average. A graph of data with a normal distribution may be bell-shaped with a peak at the mean value. In an embodiment, distribution presenter module 2962 may present a plurality of choices for a group of health service option selection factors where slider bar configurability may allow an individual to find a "sweet spot" (e.g., "I am willing to spend this much money, endure this much inconvenience, and sustain only this much loss of dignity in order to achieve a 90% probability [calculated in, for example, a normal distribution with a standard deviation of X] of living 10 or more years"). In some instances, distribution presenter module 2962 may include a computer processor.

Figure 42:
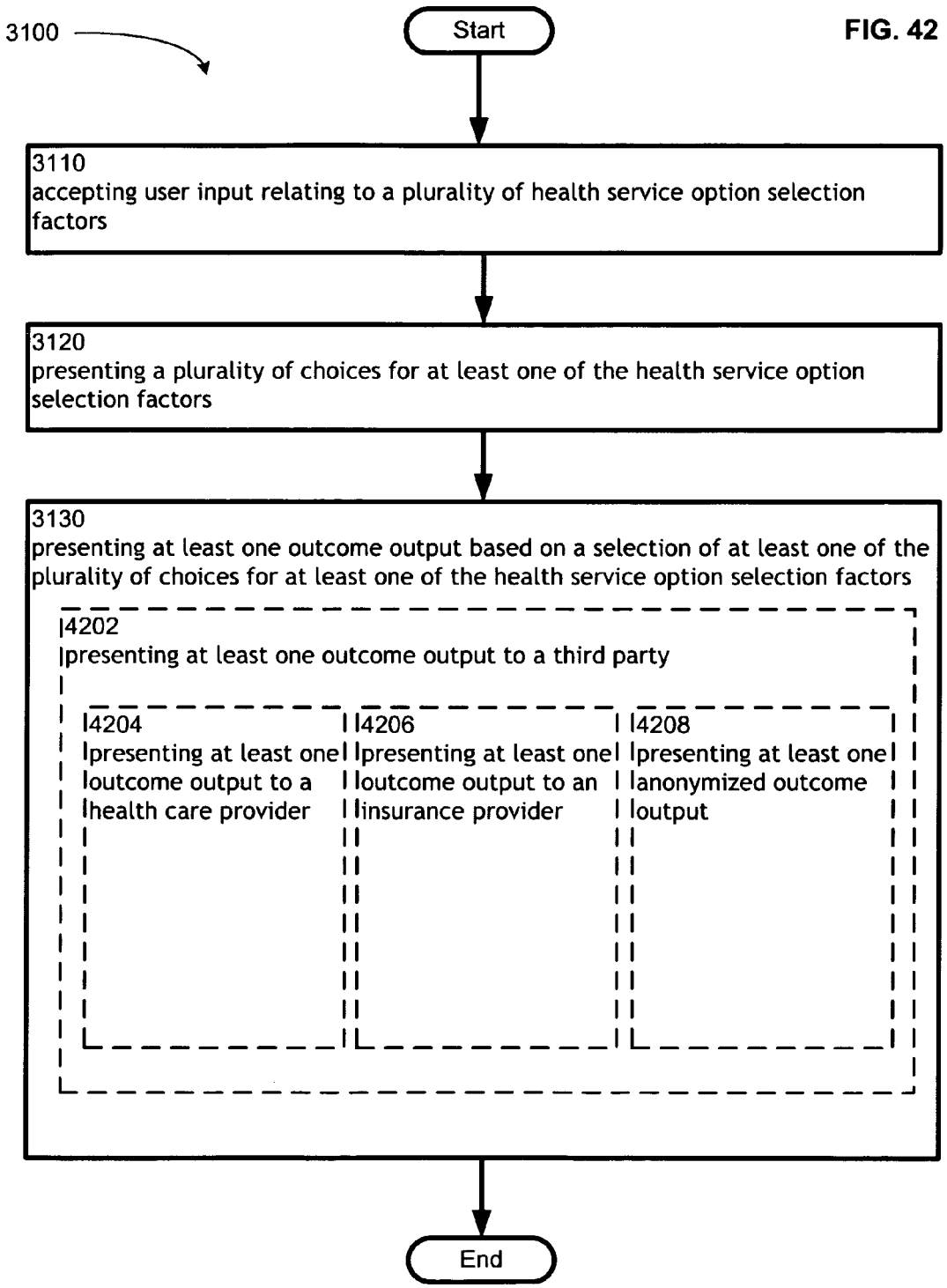
FIG. 42 illustrates an alternative embodiment of the operational flow of FIG. 31.

FIG. 42 illustrates alternative embodiments of the example operational flow 3100 of FIG. 31. FIG. 42 illustrates example embodiments where operation 3130 may include at least one additional operation. Additional operations may include operation 4202, operation 4204, operation 4206, and/or operation 4208.

Operation 4202 illustrates presenting at least one outcome output to a third party. For example, as shown in FIGS. 27 through 30, third party presenter module 2964 may present at least one outcome output to a third party. A third party may include a party that is an independent party, person, and/or entity. Some examples of a third party may include a physician, a medical database, a hospital, a law enforcement agency, and/or a pharmacy.

In one embodiment, third party presenter module 2964 may present an indication to an insurance company. Another example of reporting to a third party may include creating displays and reports for aggregating data from results, further discussed in Bair et al., U.S. Pat. No. 6,067,523, which is incorporated herein by reference. In some instances, third party presenter module 2964 may include a computer processor and/or a communications device, such as a monitor and network link.

Further, operation 4204 illustrates presenting at least one outcome output to a health care provider. For example, as shown in FIGS. 27 through 30, health care provider presenter module 2966 may present at least one outcome output to a health care provider. A health care provider may include a pharmacy, a pharmaceutical company, a medical device company, a research institution, a computer software and/or computer hardware company, a website, a nurse and/or a physician. In one embodiment, health care provider presenter module 2966 may present to a physician an outcome output via a secured website. In some instances, health care provider presenter module 2966 may include a computer processor.

Further, operation 4206 illustrates presenting at least one outcome output to an insurance provider. For example, as shown in FIGS. 27 through 30, insurance provider presenter module 2968 may present at least one outcome to an insurance provider. In an embodiment, insurance provider presenter module 2968 can present an outcome output to a medical insurance provider based on an individual's personal preferences. This may serve to provide information to an insurer that may allow the insurer to better predict future coverage and may allow the individual to comply with an agreement, for example to provide certain medical information to the insurance company. In some instances, insurance provider presenter module 2968 may include a computer processor.

Further, operation 4208 illustrates presenting at least one anonymized outcome output. For example, as shown in FIGS. 27 through 30, anonymous presenter module 2970 may present at least one anonymized outcome output. In an embodiment, anonymous presenter module 2970 can present anonymized outcome output to an insurance company. Presenting anonymized information may serve to protect the identity of the individual. Another example of presenting at least one anonymized outcome output may be found in Mayaud, U.S. Pat. No. 7,519,540, which is incorporated herein by reference. In some instances, anonymous presenter module 2970 may include a computer processor.

Figure 43:
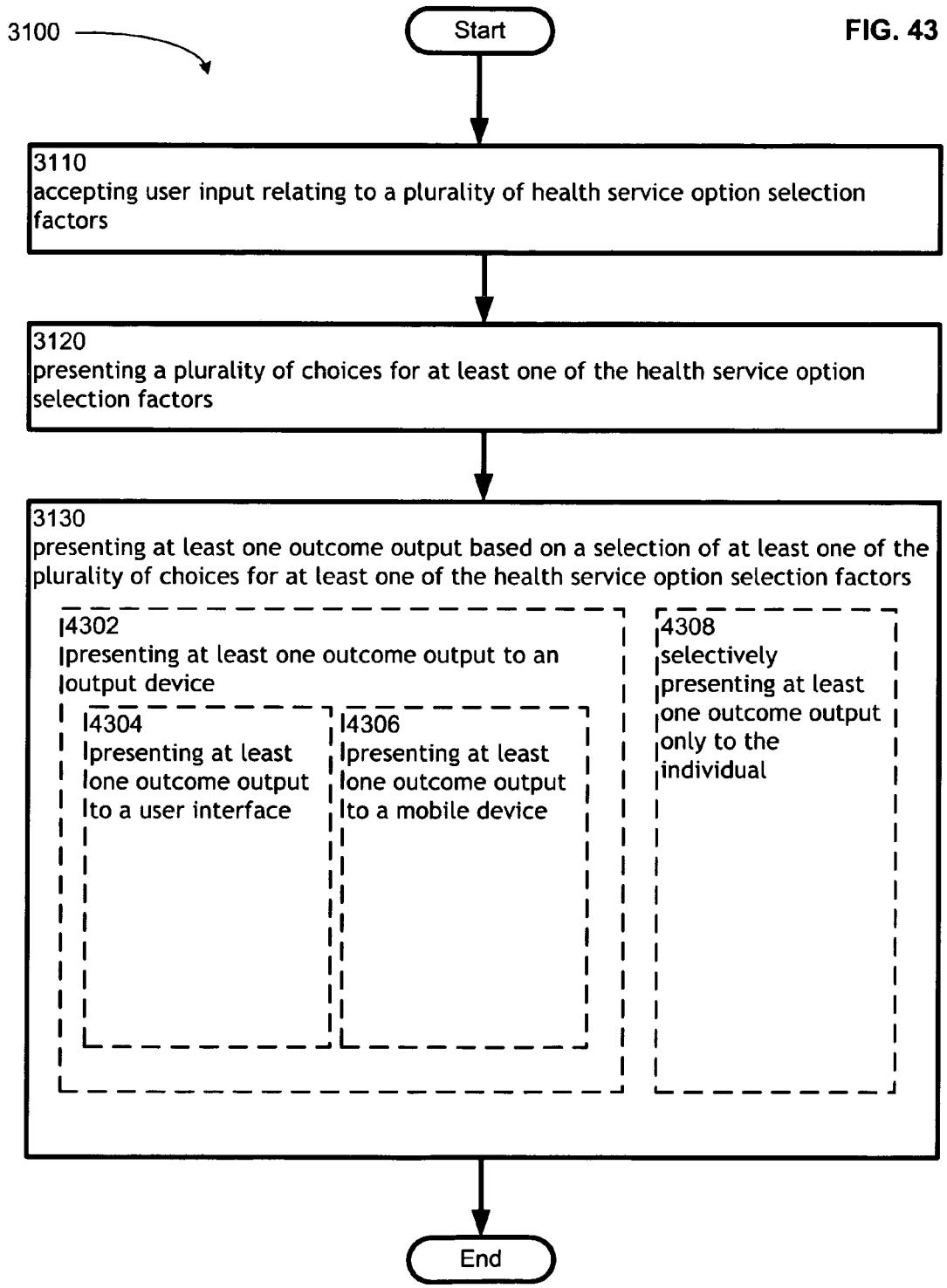
FIG. 43 illustrates an alternative embodiment of the operational flow of FIG. 31.

FIG. 43 illustrates alternative embodiments of the example operational flow 3100 of FIG. 31. FIG. 43 illustrates example embodiments where operation 3130 may include at least one additional operation. Additional operations may include operation 4302, operation 4304, operation 4306, and/or operation 4308.

Operation 4302 illustrates presenting at least one outcome output to an output device. For example, as shown in FIGS. 27 through 30, output device presenter module 2972 may present at least one outcome output to an output device. In one example, output device presenter module 2972 may present an indication of at least one recommended health service option to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134 and/or user 118. In some instances, output device presenter module 2972 may include a computer processor.

Further, operation 4304 illustrates presenting at least one outcome output to a user interface. For example, as shown in FIGS. 27 through 30, user interface presenter module 2974 may present at least one outcome output to a user interface. In one embodiment, user interface presenter module 2974 may present to a touchscreen device. A user interface may include means by which an individual may interact with a system. Some examples of a user interface may include a touchscreen, a graphical user interface, a tactile interface, and/or a live user interface. In some instances, user interface presenter module 2974 may include a computer processor.

Further, operation 4306 illustrates presenting at least one outcome output to a mobile device. For example, as shown in FIGS. 27 through 30, mobile presenter module 2976 may present at least one outcome output to a mobile device. In one embodiment, mobile presenter module 2976 may present to a mobile phone. A mobile device may include a portable computing device and may have wireless connection capability. Some examples of a mobile device may include a laptop or notebook computer, a personal digital assistant (PDA), an iPod, a smartphone, an Enterprise digital assistant (EDA), and/or a pager. In some instances, mobile presenter module 2976 may include a computer processor.

Operation 4308 illustrates selectively presenting at least one outcome output only to the individual. For example, as shown in FIGS. 27 through 30, selective presenter module 2978 may selectively present at least one outcome output only to the individual. Selective presenting may include limiting and/or blocking access of an individual's compliance results and/or a recommended therapy, such as a prescribed artificial sensory experience and/or bioactive agent to a specific party. For example, selective presenter module 2978 may present only to individual 134 and may keep results of a certain recommended combination therapy confidential. In one embodiment, an encryption key may be employed to protect selected information. In some instances, selective presenter module 2978 may include a computer processor.

Figure 44:
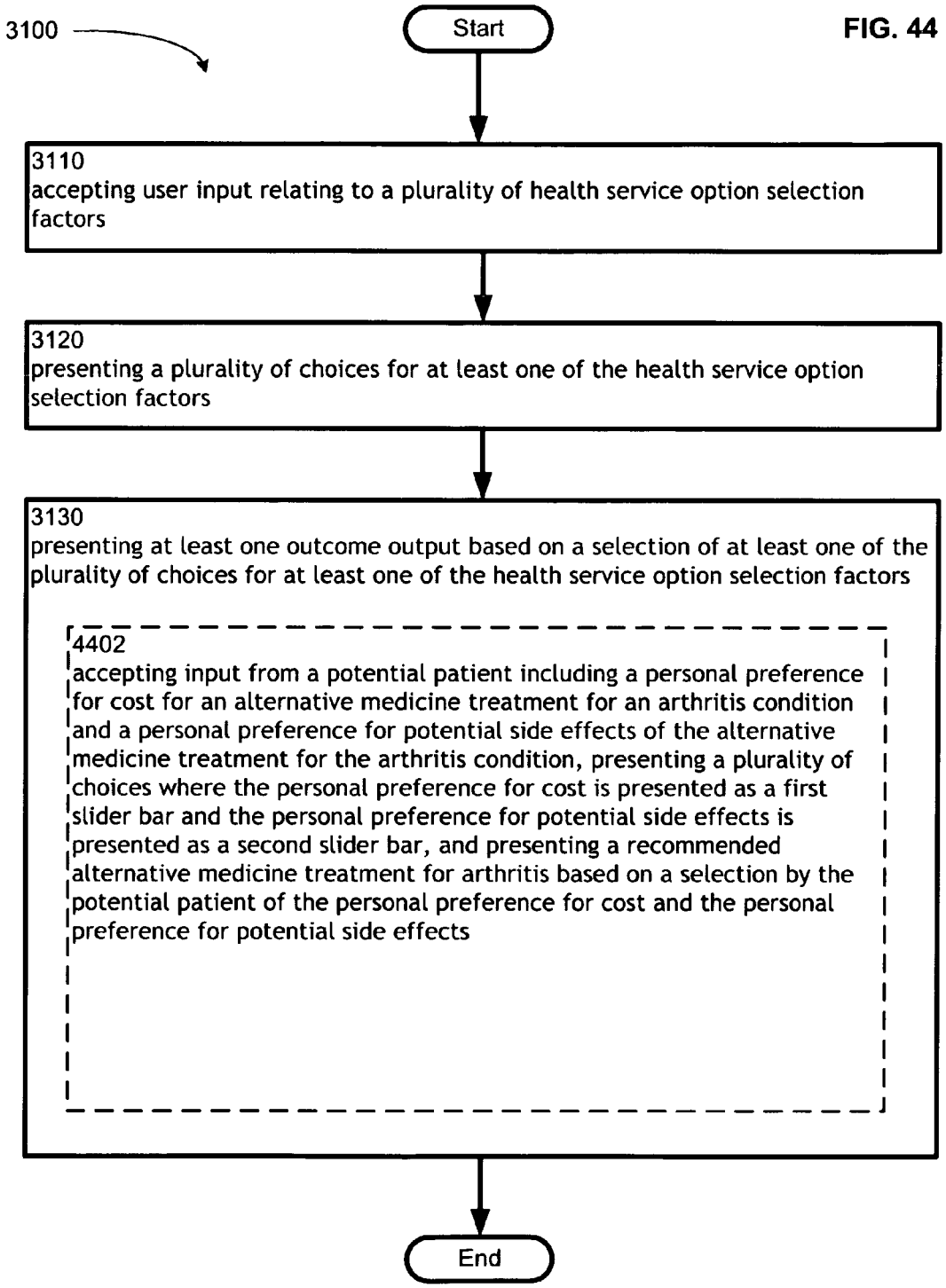
FIG. 44 illustrates an alternative embodiment of the operational flow of FIG. 31.

FIG. 44 illustrates alternative embodiments of the example operational flow 3100 of FIG. 31. FIG. 44 illustrates example embodiments where operation 3130 may include at least one additional operation. Additional operations may include operation 4402.

Operation 4402 illustrates accepting input from a potential patient including a personal preference for cost for an alternative medicine treatment for an arthritis condition and a personal preference for potential side effects of the alternative medicine treatment for the arthritis condition, presenting a plurality of choices where the personal preference for cost is presented as a first slider bar and the personal preference for potential side effects is presented as a second slider bar, and presenting a recommended alternative medicine treatment for arthritis based on a selection by the potential patient of the personal preference for cost and the personal preference for potential side effects. For example, as shown in FIGS. 27 through 30, accepter module 2902, choice presenter module 2904, and output presenter module 2906 may accept input from a potential patient including a personal preference for cost for an alternative medicine treatment for an arthritis condition and a personal preference for potential side effects of the alternative medicine treatment for the arthritis condition, present a plurality of choices where the personal preference for cost is presented as a first slider bar and the personal preference for potential side effects is presented as a second slider bar, and present a recommended alternative medicine treatment for arthritis based on a selection by the potential patient of the personal preference for cost and the personal preference for potential side effects. In some instances, accepter module 2902 may include a computer processor. In some instances, choice presenter module 2904 may include a computer processor. In some instances, output presenter module 2906 may include a computer processor.

Figure 45:
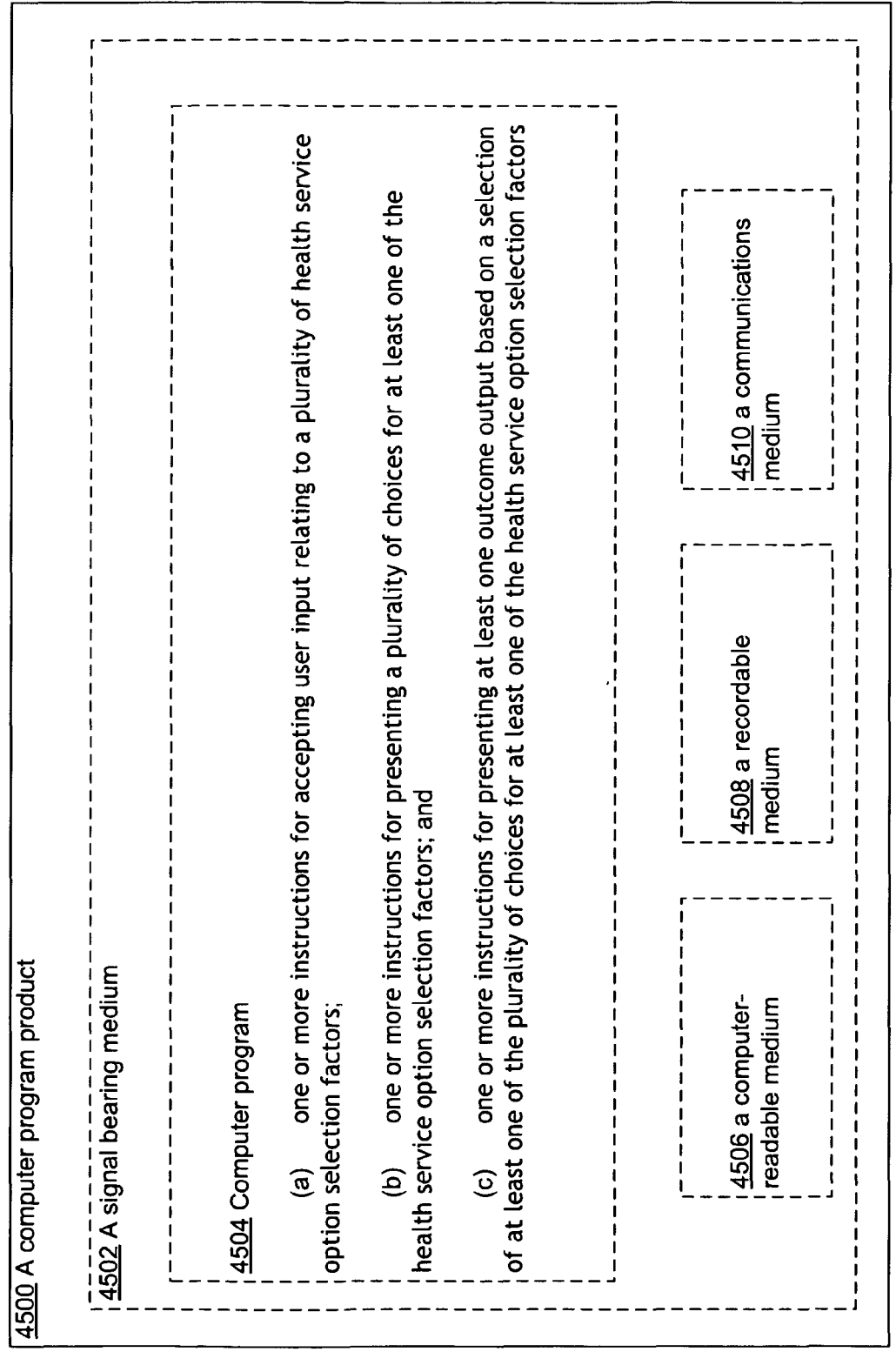
FIG. 45 illustrates a partial view of an example article of manufacture including a computer program product that includes a computer program for executing a computer process on a computing device related to health services planning and matching, which may serve as a context for introducing one or more processes and/or devices described herein.

FIG. 45 illustrates a partial view of an example computer program product 4500 that includes a computer program 4504 for executing a computer process on a computing device. An embodiment of the example computer program product 4500 is provided using a signal-bearing medium 4502, and may include one or more instructions for accepting user input relating to a plurality of health service option selection factors, one or more instructions for presenting a plurality of choices for at least one of the health service option selection factors, and one or more instructions for presenting at least one outcome output based on a selection of at least one of the plurality of choices for at least one of the health service option selection factors. The one or more instructions may be, for example, computer executable and/or logic-implemented instructions. In one implementation, the signal-bearing medium 4502 may include a computer-readable medium 4506. In one implementation, the signal bearing medium 4502 may include a recordable medium 4508. In one implementation, the signal bearing medium 4502 may include a communications medium 4510.

Figure 46:
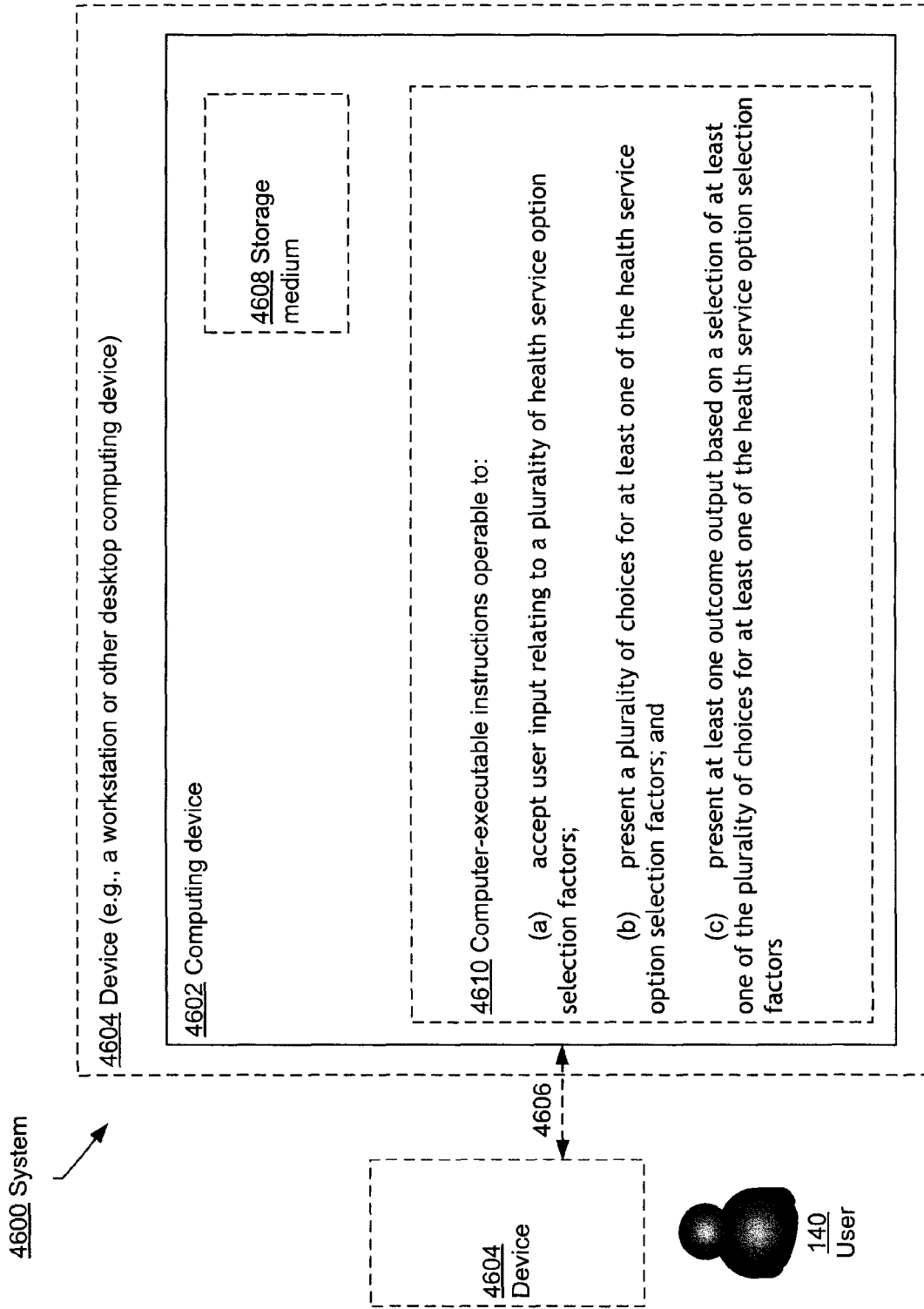
FIG. 46 illustrates an example device in which embodiments may be implemented related to health services planning and matching, which may serve as a context for introducing one or more processes and/or devices described herein.

FIG. 46 illustrates an example system 4600 in which embodiments may be implemented. The system 4600 includes a computing system environment. The system 4600 also illustrates the user 118 using a device 4604, which is optionally shown as being in communication with a computing device 4602 by way of an optional coupling 4606. The optional coupling 4606 may represent a local, wide-area, or peer-to-peer network, or may represent a bus that is internal to a computing device (e.g., in example embodiments in which the computing device 4602 is contained in whole or in part within the device 4604). A storage medium 4608 may be any computer storage media.

The computing device 4602 includes computer-executable instructions 4610 that when executed on the computing device 4602 cause the computing device 4602 to accept user input relating to a plurality of health service option selection factors, present a plurality of choices for at least one of the health service option selection factors, and present at least one outcome output based on a selection of at least one of the plurality of choices for at least one of the health service option selection factors. As referenced above and as shown in FIG. 46, in some examples, the computing device 4602 may optionally be contained in whole or in part within the device 4604.

In FIG. 46, then, the system 4600 includes at least one computing device (e.g., 4602 and/or 4604). The computer-executable instructions 4610 may be executed on one or more of the at least one computing device. For example, the computing device 4602 may implement the computer-executable instructions 4610 and output a result to (and/or receive data from) the computing device 4604. Since the computing device 4602 may be wholly or partially contained within the computing device 4604, the device 4604 also may be said to execute some or all of the computer-executable instructions 4610, in order to be caused to perform or implement, for example, various ones of the techniques described herein, or other techniques.

The device 4604 may include, for example, a portable computing device, workstation, or desktop computing device. In another example embodiment, the computing device 4602 is operable to communicate with the device 4604 associated with the user 118 to receive information about the input from the user 118 for performing data access and data processing and presenting an output of the user-health test function at least partly based on the user data.

Although a user 140 is shown/described herein as a single illustrated figure, those skilled in the art will appreciate that a user 140 may be representative of a human user, a robotic user (e.g., computational entity), and/or substantially any combination thereof (e.g., a user may be assisted by one or more robotic agents). In addition, a user 140, as set forth herein, although shown as a single entity may in fact be composed of two or more entities. Those skilled in the art will appreciate that, in general, the same may be said of "sender" and/or other entity-oriented terms as such terms are used herein.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   means for accepting user input relating to a plurality of health service option selection factors including a personal preference for cost for an alternative medicine treatment for an arthritis condition and a personal preference for potential side effects of the alternative medicine treatment for the arthritis condition,
   means for presenting a plurality of choices for at least one of the health service option selection factors where the personal preference for cost is presented as a first slider bar and the personal preference for potential side effects is presented as a second slider bar; and
   means for presenting at least one outcome output based on a selection of at least one of the plurality of choices for at least one of the health service option selection factors including recommended alternative medicine treatment for arthritis based on the selection by the user for cost and the personal preference for potential side effects.

2. The system of claim 1 wherein the means for accepting user input relating to a plurality of health service option selection factors including a personal preference for cost for an alternative medicine treatment for an arthritis condition and a personal preference for potential side effects of the alternative medicine treatment for the arthritis condition comprises:
   means for accepting user input including an indication of at least one health-related status of an individual.

3. The system of claim 2 wherein the means for accepting user input including an indication of at least one health-related status of an individual comprises: means for accepting health care provider input including an indication of at least one health-related status of an individual.

4. The system of claim 2 wherein the means for accepting user input including an indication of at least one health-related status of an individual comprises:
   means for accepting patient input including an indication of at least one health-related status of the patient.

5. The system of claim 2 wherein the means for accepting user input including an indication of at least one health-related status of an individual comprises:
   means for accepting health maintenance organization input including an indication of at least one health-related status of a patient.

6. The system of claim 2 wherein the means for accepting user input including an indication of at least one health-related status of an individual comprises:
   means for accepting insurer input including an indication of at least one health-related status of an insured individual.

7. The system of claim 1 wherein the means for accepting user input relating to a plurality of health service option selection factors including a personal preference for cost for an alternative medicine treatment for an arthritis condition and a personal preference for potential side effects of the alternative medicine treatment for the arthritis condition comprises:
   means for accepting an indication of at least one medical diagnosis.

8. The system of claim 1 wherein the means for accepting user input relating to a plurality of health service option selection factors including a personal preference for cost for an alternative medicine treatment for an arthritis condition and a personal preference for potential side effects of the alternative medicine treatment for the arthritis condition comprises:
   means for accepting an indication of at least one symptom.

9. The system of claim 8 wherein the means for accepting an indication of at least one symptom comprises:
   means for accepting an indication of at least one of pain, cardiac complaint, neurologic complaint, pulmonary complaint, hematologic complaint, infectious complaint, vascular complaint, gastrointestinal complaint, hepatobiliary complaint, renal complaint, metabolic complaint, musculoskeletal complaint, urologic complaint, gynecologic complaint, rheumatologic complaint, otolaryngologic complaint, or dermatologic complaint.

10. The system of claim 8 wherein the means for accepting an indication of at least one symptom comprises:
    means for accepting an indication of a symptom profile.

11. The system of claim 1 wherein the means for presenting a plurality of choices for at least one of the health service option selection factors where the personal preference for cost is presented as a first slider bar and the personal preference for potential side effects is presented as a second slider bar comprises:

means for presenting a plurality of choices for at least one of the health service option selection factors to an interested party.

12. The system of claim 11 wherein the means for presenting a plurality of choices for at least one of the health service option selection factors to an interested party comprises:

means for presenting a plurality of choices for at least one of the health service option selection factors to the individual.

13. The system of claim 11 wherein the means for presenting a plurality of choices for at least one of the health service option selection factors to an interested party comprises:

means for presenting a plurality of choices for at least one of the health service option selection factors to a physician.

14. The system of claim 11 wherein the means for presenting a plurality of choices for at least one of the health service option selection factors to an interested party comprises:

means for presenting a plurality of choices for at least one of the health service option selection factors to an insurance company.

15. The system of claim 1 wherein the means for presenting a plurality of choices for at least one of the health service option selection factors where the personal preference for cost is presented as a first slider bar and the personal preference for potential side effects is presented as a second slider bar comprises:

means for presenting a plurality of choices for at least one of the health service option selection factors to a user interface.

16. The system of claim 1 wherein the means for presenting a plurality of choices for at least one of the health service option selection factors where the personal preference for cost is presented as a first slider bar and the personal preference for potential side effects is presented as a second slider bar comprises:

means for presenting the plurality of choices for at least one of the health service option selection factors at least partially based on selection factors that have been calculated with a normal distribution.

17. The system of claim 1 wherein the means for presenting at least one outcome output based on a selection of at least one of the plurality of choices for at least one of the health service option selection factors including a recommended alternative medicine treatment for arthritis based on the selection by the user for cost and the personal preference for potential side effects comprises:

means for presenting at least one outcome output to a third party.

18. The system of claim 17 wherein the means for presenting at least one outcome output to a third party comprises:

means for presenting at least one outcome output to a health care provider.

19. The system of claim 17 wherein the means for presenting at least one outcome output to a third party comprises:

means for presenting at least one outcome output to an insurance provider.

20. The system of claim 17 wherein the means for presenting at least one outcome output to a third party comprises:

means for presenting at least one anonymized outcome output.

21. The system of claim 1 wherein the means for presenting at least one outcome output based on a selection of at least one of the plurality of choices for at least one of the health service option selection factors including a recommended alternative medicine treatment for arthritis based on the selection by the user for cost and the personal preference for potential side effects comprises:

means for presenting at least one outcome output to an output device.

22. The system of claim 21 wherein the means for presenting at least one outcome output to an output device comprises:

means for presenting at least one outcome output to a user interface.

23. The system of claim 21 wherein the means for presenting at least one outcome output to an output device comprises:

means for presenting at least one outcome output to a mobile device.

24. A method comprising:

accepting user input relating to a plurality of health service option selection factors including a personal preference for cost for an alternative medicine treatment for an arthritis condition and a personal preference for potential side effects of the alternative medicine treatment for the arthritis condition, presenting a plurality of choices for at least one of the health service option selection factors where the personal preference for cost is presented as a first slider bar and the personal preference for potential side effects is presented as a second slider bar; and presenting at least one outcome output based on a selection of at least one of the plurality of choices for at least one of the health service option selection factors including a recommended alternative medicine treatment for arthritis based on the selection by the user for cost and the personal preference for potential side effects, where each step is performed using a microprocessor.

25. The system of claim 24 wherein the accepting user input relating to a plurality of health service option selection factors including a personal preference for cost for an alternative medicine treatment for an arthritis condition and a personal preference for potential side effects of the alternative medicine treatment for the arthritis condition comprises:

accepting user input including an indication of at least one health-related status of an individual.

26. The system of claim 25 wherein the accepting user input including an indication of at least one health-related status of an individual comprises:

accepting health care provider input including an indication of at least one health-related status of an individual.

27. The system of claim 25 wherein the accepting user input including an indication of at least one health-related status of an individual comprises:

accepting patient input including an indication of at least one health-related status of the patient.

28. The system of claim 25 wherein the accepting user input including an indication of at least one health-related status of an individual comprises:

accepting health maintenance organization input including an indication of at least one health-related status of a patient.

29. The system of claim 25 wherein the accepting user input including an indication of at least one health-related status of an individual comprises:

accepting insurer input including an indication of at least one health-related status of an insured individual.

30. The system of claim 24 wherein the accepting user input relating to a plurality of health service option selection factors including a personal preference for cost for an alternative medicine treatment for an arthritis condition and a personal preference for potential side effects of the alternative medicine treatment for the arthritis condition comprises:

accepting an indication of at least one medical diagnosis.

31. The system of claim 24 wherein the accepting user input relating to a plurality of health service option selection factors including a personal preference for cost for an alternative medicine treatment for an arthritis condition and a personal preference for potential side effects of the alternative medicine treatment for the arthritis condition comprises:

accepting an indication of at least one symptom.

32. The system of claim 31 wherein the accepting an indication of at least one symptom comprises:

accepting an indication of at least one of pain, cardiac complaint, neurologic complaint, pulmonary complaint, hematologic complaint, infectious complaint, vascular complaint, gastrointestinal complaint, hepatobiliary complaint, renal complaint, metabolic complaint, musculoskeletal complaint, urologic complaint, gynecologic complaint, rheumatologic complaint, otolaryngologic complaint, or dermatologic complaint.

33. The system of claim 31 wherein the accepting an indication of at least one symptom comprises:

accepting an indication of a symptom profile.

34. The system of claim 24 wherein the presenting a plurality of choices for at least one of the health service option selection factors where the personal preference for cost is presented as a first slider bar and the personal preference for potential side effects is presented as a second slider bar comprises:

presenting a plurality of choices for at least one of the health service option selection factors to an interested party.

35. The system of claim 34 wherein the presenting a plurality of choices for at least one of the health service option selection factors to an interested party comprises:

presenting a plurality of choices for at least one of the health service option selection factors to the individual.

36. The system of claim 34 wherein the presenting a plurality of choices for at least one of the health service option selection factors to an interested party comprises:

presenting a plurality of choices for at least one of the health service option selection factors to a physician.

37. The system of claim 34 wherein the presenting a plurality of choices for at least one of the health service option selection factors to an interested party comprises:

presenting a plurality of choices for at least one of the health service option selection factors to an insurance company.

38. The system of claim 24 wherein the presenting a plurality of choices for at least one of the health service option selection factors where the personal preference for cost is presented as a first slider bar and the personal preference for potential side effects is presented as a second slider bar comprises:

presenting a plurality of choices for at least one of the health service option selection factors to a user interface.

39. The system of claim 24 wherein the presenting a plurality of choices for at least one of the health service option selection factors where the personal preference for cost is presented as a first slider bar and the personal preference for potential side effects is presented as a second slider bar comprises:

presenting the plurality of choices for at least one of the health service option selection factors at least partially based on selection factors that have been calculated with a normal distribution.

40. The system of claim 24 wherein the presenting at least one outcome output based on a selection of at least one of the plurality of choices for at least one of the health service option selection factors including a recommended alternative medicine treatment for arthritis based on the selection by the user for cost and the personal preference for potential side effects comprises:

presenting at least one outcome output to a third party.

41. The system of claim 40 wherein the presenting at least one outcome output to a third party comprises:

presenting at least one outcome output to a health care provider.

42. The system of claim 40 wherein the presenting at least one outcome output to a third party comprises:

presenting at least one outcome output to an insurance provider.

43. The system of claim 40 wherein the presenting at least one outcome output to a third party comprises:

presenting at least one anonymized outcome output.

44. The system of claim 24 wherein the presenting at least one outcome output based on a selection of at least one of the plurality of choices for at least one of the health service option selection factors including a recommended alternative medicine treatment for arthritis based on the selection by the user for cost and the personal preference for potential side effects comprises:

presenting at least one outcome output to an output device.

45. The system of claim 44 wherein the presenting at least one outcome output to an output device comprises:

presenting at least one outcome output to a user interface.

46. The system of claim 44 wherein the presenting at least one outcome output to an output device comprises:

presenting at least one outcome output to a mobile device.

47. A computer program product comprising:

a non-transitory computer-readable medium bearing one or more instructions for accepting user input relating to a plurality of health service option selection factors including a personal preference for cost for an alternative medicine treatment for an arthritis condition and a personal preference for potential side effects of the alternative medicine treatment for the arthritis condition;

one or more instructions for presenting a plurality of choices for at least one of the health service option selection factors where the personal preference for cost is presented as a first slider bar and the personal preference for potential side effects is presented as a second slider bar; and one or more instructions for presenting at least one outcome output based on a selection of at least one of the plurality of choices for at least one of the health service option selection factors including a recommended alternative medicine treatment for arthritis based on the selection by the user for cost and the personal preference for potential side effects.

48. The computer program product of claim 47, wherein the computer-readable medium includes a recordable medium.

49. The computer program product of claim 47, wherein the computer-readable medium includes a communications medium.

* * * * *